United States Patent
Paz-Ares Rodríguez et al.

(10) Patent No.: US 11,408,038 B2
(45) Date of Patent: Aug. 9, 2022

(54) N-CADHERIN AND FGFR1 AND/OR FGFR4 FOR USE IN PREDICTING THE RESPONSE OF PATIENTS TO A LUNG CANCER TREATMENT AND METHOD AND KIT BASED ON SAID USE

(71) Applicants: FUNDACIÓN DE INVESTIGACIÓN HOSPITAL 12 DE OCTUBRE, Madrid (ES); SERVICIO ANDALUZ DE SALUD, Seville (ES); CONSE-JO SUPERIOR DE INVESTIGACIONES CIENTÍFI-CAS (CSIC), Seville (ES)

(72) Inventors: Luis Paz-Ares Rodríguez, Madrid (ES); Álvaro Quintanal Villalonga, Seville (ES); Irene Ferrer Sánchez, Madrid (ES); Sonia Molina Pinelo, Seville (ES); Amancio Carnero Moya, Seville (ES)

(73) Assignee: FUNDACIÓN DE INVESTIGACIÓN HOSPITAL 12 DE OCTUBRE

( * ) Notice: Subject to any disclaimer, the term of this patent is extended or adjusted under 35 U.S.C. 154(b) by 0 days.

(21) Appl. No.: 16/630,021

(22) PCT Filed: Jul. 13, 2018

(86) PCT No.: PCT/ES2018/070501
§ 371 (c)(1),
(2) Date: Jan. 10, 2020

(87) PCT Pub. No.: WO2019/016422
PCT Pub. Date: Jan. 24, 2019

(65) Prior Publication Data
US 2021/0164053 A1 Jun. 3, 2021

(30) Foreign Application Priority Data
Jul. 13, 2017 (ES) .............................. ESP201730929

(51) Int. Cl.
C12Q 1/6886 (2018.01)
G01N 33/574 (2006.01)

(52) U.S. Cl.
CPC ..... *C12Q 1/6886* (2013.01); *G01N 33/57423* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,709,718 B1 | 4/2014 | Thomas et al. | |
| 2013/0210026 A1* | 8/2013 | Haley | A61P 1/18 435/7.1 |
| 2015/0335643 A1* | 11/2015 | Thomas | A61K 31/4025 514/275 |

FOREIGN PATENT DOCUMENTS

EP 2695950 A1 2/2014

OTHER PUBLICATIONS

Enard et al. (Science 2002 vol. 296 p. 340) (Year: 2002).*
Cobb et al. (Crit Care Med 2002 vol. 30 p. 2711) (Year: 2002).*
Supplemental European Search Report, dated Jan. 20, 2021.
Thompson, Karol L., et al.; "Cp,[arospm pf tje doagmpstoc [erfpr,amce pf ji,am wjp;e gemp,e ,ocrparrays using mixed-tissue RNA reference samples," Toxicology Letters, 2009, vol. 186, pp. 58-61.
Hazan, Rachel B., et al.; "Cadherin Switch in Tumor Progression," Ann. N.Y. Acad. Sci., 2004, pp. 155-163; doi: 10.1196/annals.1294.016.
Ezzat, Shereen, et al.; "Targeting N-Cadherin through Fibroblast Growth Factor Receptor-4: Distinct Pathogenetic and Therapeutic Implications,"Molecular Endocrinology, 2006, vol. 20, pp. 2965-2975, doi 10.1210/me.2006-0223.
Quintanal-Villalonga, Álvaro, et al.; "FGFR1 and FGFR4 oncogenicity depends on n-cadherin and their co-expression may redict FGFR-targeted therapy efficacy," Ebiomedicine, 2020, vol. 53, p. 102683; doi 10.1016/j. ebiom.2020.102683.
International Search Report, dated Nov. 13, 2018.
Quintanal, A, et al.; (2018) Novel predictor of FGFR1 inhibition efficacy in non-small cell lunch cancer. Proceedings: AACR Annual Meeting 2018; Apr. 14-18, 2018; Chicago, IL. Cancer Res; 78 (13 Suppl): Abstract No. 2589; URL: http://cancerres.aacrjournals.org/content/78/13 Supplement/2589.short; DOIL 10.1158/1538-7445. AM2018-2589.
Quintanal, A, et al.; (2017) "Determining the role of FGFR1 and FGFR4 in lung cancer," Thesis. Univ. of Sevilla, 2017; https://idus.us.es/xmlui/handle/11441/69697; In Spanish.
Quintanal, A, et al.; (2016) The ocogenic role of FGFR1 depends on the molecular context. Annals of Oncology, Oct. 1, 2016, vol. 27(Suppl 6), 1563P; http://academic.oup.com/annonc/article/27/suppl_6/1563P/2800460; DOI: 10.1093/annonc/mdw392.44.
Quintanal, A, et al.; (2016) FGFR4 exerts differential roles in tumorigenesis through a mechanism of cooperation Annals of Oncology, vol. 27(Suppl 6), 1564P, Oct. 1, 2016, https://academic.oup.com/annonc/article/27/suppl_6/1564P/2800461, DOI: 10.1093/annonc/mdw392.45.

(Continued)

*Primary Examiner* — Katherine D Salmon
(74) *Attorney, Agent, or Firm* — Tristan A. Fuierer; Casimir Jones, S.C.

(57) ABSTRACT

The present invention describes a method for predicting the response of a subject suffering from lung cancer to treatment with FGFR inhibitors. The relationship between the expression of the biomarkers and the treatment response allows the subjects to be classified as responsive or unresponsive to the treatment, which facilitates the therapeutic decision-making of the attending clinician. The present invention also describes the biomarkers N-cadherin, FGFR1 and FGFR4, how to analyse them and how to interpret the results obtained, in order to administer FGFR inhibitors only to the subjects that are responsive to the treatment, thereby optimising the same, which allows the unresponsive subjects to be treated with alternative therapies to the FGFR inhibitors.

7 Claims, 24 Drawing Sheets
Specification includes a Sequence Listing.

(56) References Cited

OTHER PUBLICATIONS

Suyama K. et al.; (2002) "A signaling pathway leading to metastasis is cotrolled by N-cadherin and the FGF receptor," Cancer Cell, Sep. 30, 2002, vol. 2, pp. 301-314.

Altschul, S.F. et al. (1990). "Basic local alignment search tool," J. Mol. Biol., vol. 215(3), pp. 403-410.

Blanco, R. et al. (2009). "A gene-alteration profile of human lung cancer cell lines," Human mutation, vol. 30, pp. 1199-1206.

Dutt A, et al. (2011) "Inhibitor-Sensitive FGFR1 Amplification in Human Non-Small Cell Lung Cancer," PLoS ONE 6(6): e20351. doi: 10.1371/journal.pone.0020351.

Gheldof, A. et al. (2013). "Cadherins and epithelial-to-mesenchymal transition," Prog. Mol. Biol. Transl. Sci., vol. 116, pp. 317-336.

Hanze, J. et al. (2013). "Epithelial mesenchymal transition status is associated with anti-cancer responses toward receptor tyrosine-kinase inhibition by dovitinib in human bladder cancer cells," BMC Cancer, vol. 11(13), 589.

Helfrich, B.A. et al. (2006). "Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels," Clin. Cancer Res., vol. 12(23), pp. 7117-7125.

Huang, H.P. et al. (2015). "The prognostic significance of fibroblast growth factor receptor 4 in non-small-cell lung cancer," Onco Targets Ther., vol. 8, pp. 1157-1164.

Jiang, T. et al. (2015). "FGFR1 amplification in lung squamous cell carcinoma: a systematic review with meta-analysis," Lung Cancer, vol. 87(1), pp. 1-7.

Lim, S.H. et al. (2016). "Efficacy and safety of dovitinib in pretreated patients with advanced squamous non-small cell lung cancer with FGFR1 amplification: A single-arm, phase 2 study," Cancer, vol. 122(19), pp. 3024-3031.

Nguyen, T. et al. (2016). "N-cadherin and Fibroblast Growth Factor Receptors crosstalk in the control of developmental and cancer cell migrations," Eur J. Cell Biol., vol. 95(11), vol. 415-426.

Qian, X. et al. (2014). "N-cadherin/FGFR promotes metastasis through epithelial-to-mesenchymal transition and stem/progenitor cell-like properties," Oncogene, vol. 33(26), 3411-21.

Quintanal-Villalonga, A. et al. (2016). "Tyrosine Kinase Receptor Landscape in Lung Cancer: Therapeutical Implications," Disease markers, vol. 2016, Article ID 9214056, 14 pages http://dx.doi.org/10.1155/2016/9214056.

Wesche, J. et al. (2011). "Fibroblast growth factors and their receptors in cancer," Biochem. J., vol. 437, pp. 199-213.

\* cited by examiner

FIGURE 4C
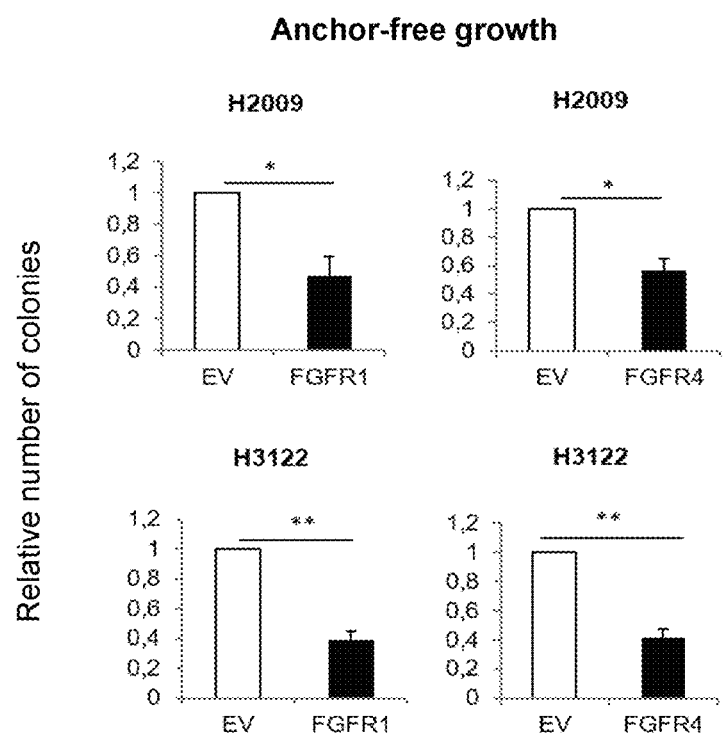
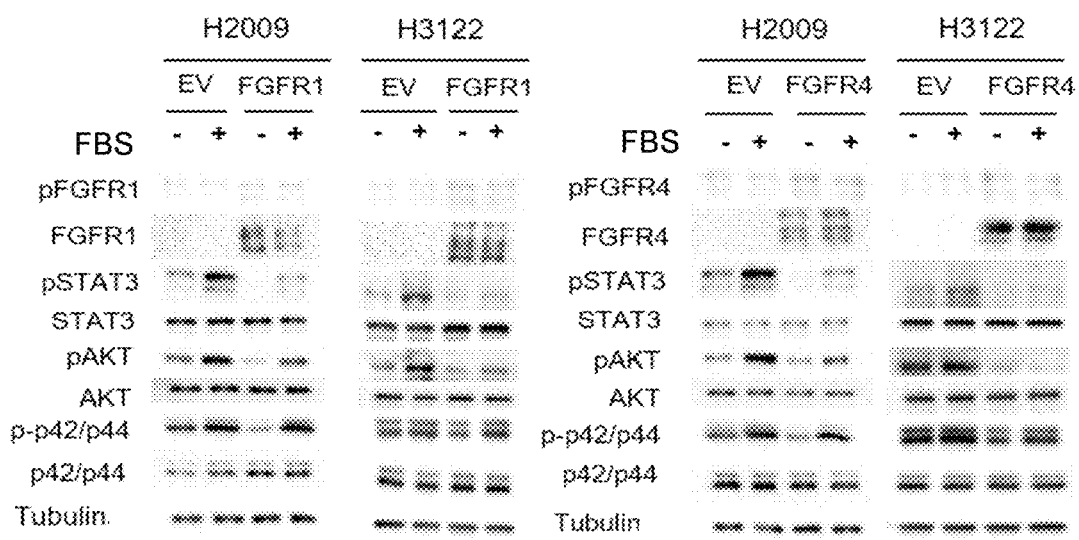
FIGURE 4D

N-CADHERIN AND FGFR1 AND/OR FGFR4 FOR USE IN PREDICTING THE RESPONSE OF PATIENTS TO A LUNG CANCER TREATMENT AND METHOD AND KIT BASED ON SAID USE

CROSS-REFERENCE TO RELATED APPLICATIONS

This application is filed under the provisions of 35 U.S.C. § 371 and claims the priority of International Patent Application No. PCT/ES2018/070501, filed on 13 Jul. 2018 entitled "N-CADHERIN AND FGFR1 AND/OR FGFR4 FOR USE IN PREDICTING THE RESPONSE OF PATIENTS TO A LUNG CANCER TREATMENT AND METHOD AND KIT BASED ON SAID USE" in the name of Luis PAZ-ARES RODRÍGUEZ, et al., which claims priority to Spanish Patent Application No. P201730929 filed on 13 Jul. 2017, both of which are hereby incorporated by reference herein in their entirety.

TECHNICAL FIELD

The present invention pertains to the clinical medicine field and, more specifically, to treatment of lung cancer with anti-FGFR drugs.

The principal object of the present invention is the use of N-cadherin and FGFR1 and/or FGFR4 biomarkers in the prognosis and prediction of the response of a subject suffering lung cancer to treatment with FGFR inhibitors.

BACKGROUND OF THE INVENTION

Lung cancer is a group of diseases resulting from the malignant growth of cells of the respiratory tract, in particular in lung tissue, and is one of the most common types of cancer on a worldwide level. Due to the fact that most patients are diagnosed at advanced stages of the disease, the survival rate is very low. Lung cancer usually originates from epithelial cells and can lead to metastasis and infiltration to other tissues of the body. Although in clinical trials FGFR inhibitors have been used in the treatment of lung cancer, many patients do not respond to these therapies.

The ability to determine whether a treatment will be effective or not for a particular patient prior to its administration will benefit the patient himself, as this will prevent the unnecessary suffering of the side-effects of an ineffective treatment, rapidly prioritising the search for alternative treatments, saving treatment costs and in addition, improving the expectations of an effective response.

The identification of new biomarkers that enable the prediction of the response of a patient to a treatment is decisive in the clinical treatment of any pathology. The application of high-performance technologies in lung cancer has identified numerous disruptions in genes with a potential role in this type of cancer. Many of these disruptions occur in proteins with tyrosine kinase activity (Quintanal-Villalonga 2016).

Fibroblast growth factor receptors (FGFRs) are membrane receptors with tyrosine kinase activity that bind to members of the fibroblast growth factor family. The activation of FGFRs is related to the regulation of cell survival, proliferation, migration and differentiation. It has been disclosed that the dysregulation of the FGFR signalling pathways is associated with cancer in humans (Wesche 2011); they therefore represent a significant therapeutic target in cancer. Five members of the FGFR receptor family have been identified (FGFR1, FGFR2, FGFR3, FGFR4 and FGFRL1).

FGFR inhibitors have been used successfully in preclinical models of different types of cancer. However, at a clinical level these inhibitors do not present efficacy in all patients, even though the latter were selected beforehand in accordance with the current predictive criteria regarding sensitivity to these inhibitors. The patient selection criteria for participation in clinical trials with FGFR inhibitors have generally been directed toward the detection of the amplification of certain FGFRs, but unfortunately these criteria have revealed that their capacity of prediction of response to treatment is not totally reliable, representing a problem in the treatment of patients with cancer. Preliminary results of clinical trials have revealed that many of the tumours where the FGFR1 gene is amplified do not respond to therapy directed toward the FGFR receptor, this suggesting that other biomarkers are necessary to correctly stratify the patients and to predict their response to this type of therapy. The object of the present invention is to determine whether a patient suffering from lung cancer will respond to treatment with FGFR inhibitors.

It has been observed that in lung cancer, approximately 20% of squamous cell carcinomas and 1-3% of adenocarcinomas has amplification of the FGFR1 gene. On the other hand, it is known that the FGFR4 gene presents mutations in some patients with adenocarcinoma, and furthermore, that expression of the FGFR4 receptor has been related to a worse prognosis in non-small-cell lung cancer. These data, together with various clinical trials on this pathology, suggest that both these genes may have great relevance in lung cancer (Dutt, 2011; Jiang, 2015; Huang, 2015; Lim, 2016).

The use of FGFR inhibitors in the treatment of lung cancer in patients with high levels of FGFR1 expression has also been disclosed (US2015335643A1 and U.S. Pat. No. 8,709,718B1).

Neural cadherin (NCAD), N-cadherin or Cadherin-2 (CDH2) is a transmembrane glycoprotein responsible for the cell-cell binding encoded by the CDH2 gene. It plays an important role during development, in CNS cells, those of the cardiac muscle, but also in the metastasis of cancer. It also plays an important role in the mediation of neural signals. N-cadherin positively regulates FGFR activation in tumour cells, increasing the invasive activity of the tumour cells and enhancing the progression of metastasis in preclinical models of some types of cancer (Qian 2014; Nguyen 2016).

It has been verified that in bladder cancer the mRNA levels of epithelial-mesenchymal transition markers, such as E-cadherin, and N-cadherin, can be used jointly to predict the response to treatment with an FGFR inhibitor (TI-258), due to the fact that mesenchymal bladder cancer cell lines are more responsive than those of the epithelial type (Hänze 2013).

However, what has not been disclosed in the state of the art nor has been suggested by any document is the relationship between the level of expression of N-cadherin on the one hand and the level of expression of FGFR1 and/or FGFR4 on the other, as biomarkers, to determine whether treatment with FGFR inhibitors is effective in a patient suffering lung cancer. The present invention reveals for the first time the relevance at a therapeutic level of N-cadherin in the tumourigenic role of FGFR1 and FGFR4 in lung cancer.

DESCRIPTION OF THE INVENTION

Brief Description of the Invention

In one embodiment, the present invention relates to an in vitro method for predicting the response of a subject suffering from lung cancer to a treatment with at least one FGFR inhibitor, comprising:
  a) detecting in a biological sample obtained from said subject the levels of the biomarker N-cadherin in combination with the expression of at least one of the biomarkers FGFR1 and/or FGFR4.
  b) comparing the expression level of the biomarkers determined in (a) with a reference sample, wherein high levels of the markers detected indicates that the subject will respond to the treatment.

In a more preferred embodiment, the determination of the level of expression of the biomarkers in the in vitro method is performed by measuring the amount of N-cadherin protein and the amount of FGFR1 and/or FGFR4 protein in the sample, or by measuring the amount of mRNA of the CDH2 gene and the amount of mRNA of the FGFR1 and/or FGFR4 genes in the sample.

In another preferred embodiment, the lung cancer is non-small-cell lung cancer (NSCLC). In a still more preferred embodiment, the NSCLC is selected from adenocarcinoma and epidermoid or squamous cell carcinoma.

In another embodiment of the invention, the biological sample analysed in step (a) of the in vitro method, in accordance with any of the previous embodiments, is selected from the group comprising: whole blood, serum, plasma, sputum, sweat, urine, bronchoalveolar lavage, or biopsy of the primary or metastatic tumoural tissue. In a still more preferred embodiment, the biological sample is a biopsy of the primary tumour of the subject.

In a preferred embodiment of the in vitro method in accordance with any of the previous embodiments, the detection of the amount of the biomarkers is performed by means of at least one of the methods selected from: HPLC (high performance liquid chromatography), LC/MS (liquid chromatography coupled to mass spectrometry), ELISA, DAS ELISA, protein immunoprecipitation, immunoelectrophoresis, Western Blot, protein immunostaining, Northern Blot, reverse transcription PCR (RT-PCR), quantitative PCR (q-PCR), RIA (radioimmunoassay), in situ hybridisation, nuclease protection assay, massive sequencing, immunocytochemical or immunohistochemical techniques, genomic DNA microarrays, protein microarrays, messenger RNA microarrays, cDNA microarrays, peptide microarrays, tissue microarrays, cellular or transfection microarrays, antibody microarrays, lysate or serum microarrays, reverse phase protein microarrays, peptide microarrays or genotyping microarrays, among others. In a more preferred embodiment, the detection of the biomarker mRNA is carried out by reverse transcription PCR (RT-PCR) or quantitative PCR (q-PCR).

In a preferred embodiment of the in vitro method in accordance with any of the preceding embodiments, high levels of the biomarkers detected correspond to a level at least two times higher than the level of the same marker in a reference sample.

In another embodiment of the method, the at least one FGFR inhibitor is selected from the group comprising BGJ398, AZD4547, Debio-1347, Dovitinib, BLU9931, FIIN-2, JNJ-42756493, LY2874455, Ponatinib, BIBF1120, PD173074, PD166866, BLU554, S49076, NSC12, PHA-739358, TSU-68, BMS-540215, TKI-258, MK-2461, BMS-582664, AG 1296, SSR128129E, LY2874455 and SU5402.

Another embodiment of the invention relates to the combination of the biomarker N-cadherin and at least one second biomarker selected from FGFR1 and/or FGFR4, for use in the prognosis and/or prediction of the response of a subject suffering from lung cancer to treatment with FGFR inhibitors.

In a more preferred embodiment of this use, the level of expression of each biomarker is determined by measuring the level of mRNA of the genes CDH2 and FGFR1 and/or FGFR4, and/or the level of N-cadherin and FGFR1 and/or FGFR4 protein.

In a preferred embodiment of the combination of the biomarkers for use, in accordance with either of the two immediately preceding embodiments, the lung cancer is a non-small-cell lung cancer selected from adenocarcinoma or squamous cell carcinoma.

In another embodiment, the at least one FGFR inhibitor of the combination of biomarkers for use in accordance with any of the above embodiments of use is selected from the group comprising: BGJ398, AZD4547, Debio-1347, Dovitinib, BLU9931, FIIN-2, JNJ-42756493, LY2874455, Ponatinib, BIBF1120, PD173074, PD166866, BLU554, S49076, NSC12, PHA-739358, TSU-68, BMS-540215, TKI-258, MK-2461, BMS-582664, AG 1296, SSR128129E, LY2874455 and SU5402.

Another embodiment of the invention relates to a kit for the prognosis and/or prediction of the response of a subject suffering from lung cancer to a treatment with FGFR inhibitors comprising:
  (a) means for detecting in a biological sample obtained from the subject the levels of the biomarker N-cadherin on the one hand, and the expression of at least one of the biomarkers FGFR1 and/or FGFR4 on the other,
  (b) means for comparing the expression level of the biomarkers determined in (a) with a reference sample,
  (c) instructions for a medical professional to administer the treatment with FGFR inhibitors solely to those subjects showing high expression of N-cadherin and also high expression of FGFR1 and/or FGFR4.

In a preferred embodiment, the determination of the levels of the biomarkers in the kit is carried out by measuring the amount of protein of the biomarker N-cadherin and the amount of protein of at least one of the biomarkers FGFR1 or FGFR4 in the sample, or by measuring the amount of mRNA of the CDH2 gene and the amount of mRNA of at least one of the genes FGFR1 or FGFR4 in the sample.

In another preferred embodiment, the lung cancer sample to be analysed in the kit is a non-small-cell lung cancer sample. In a still more preferred embodiment, the NSCLC is selected from adenocarcinoma and epidermoid or squamous cell carcinoma.

In a preferred embodiment of the kit, in accordance with any of the above embodiments of said kit, the means for detecting the levels of the biomarkers comprise antibodies that specifically recognize the N-cadherin proteins and antibodies that specifically recognize the FGFR1 and/or FGFR4 proteins, or primers and/or probes that specifically detect the presence of CDH2 mRNA and also primers and/or probes that specifically detect the presence of FGFR1 and/or FGFR4 mRNA.

In another preferred embodiment of the kit, in accordance with any of the above embodiments of said kit, the biological sample is selected from the group comprising: whole blood, serum, plasma, sputum, sweat, urine, bronchoalveolar lavage, or biopsy of primary or metastatic tumour tissue.

In an additional embodiment of the kit, in accordance with any of the previous embodiments of said kit, the detection of the biomarkers is performed by means of at least one of the methods selected from: HPLC (high performance liquid chromatography), LC/MS (liquid chromatography coupled to mass spectrometry), ELISA, DAS ELISA, protein immunoprecipitation, immunoelectrophoresis, Western Blot, protein immunostaining, Northern Blot, reverse transcription PCR (RT-PCR), quantitative PCR (q-PCR), RIA (radioimmunoassay), in situ hybridization, nuclease protection assay, massive sequencing, immunocytochemical or immunohistochemical techniques, genomic DNA microarrays, protein microarrays, messenger RNA microarrays, cDNA microarrays, peptide microarrays, tissue microarrays, cellular or transfection microarrays, antibody microarrays, lysate or serum microarrays, reverse phase protein microarrays, peptide microarrays or genotyping microarrays, among others. In a more preferred embodiment, the detection of the biomarker mRNA is carried out by means of reverse transcription PCR (RT-PCR) or quantitative PCR (q-PCR).

DETAILED DESCRIPTION OF THE INVENTION

Figure 1:
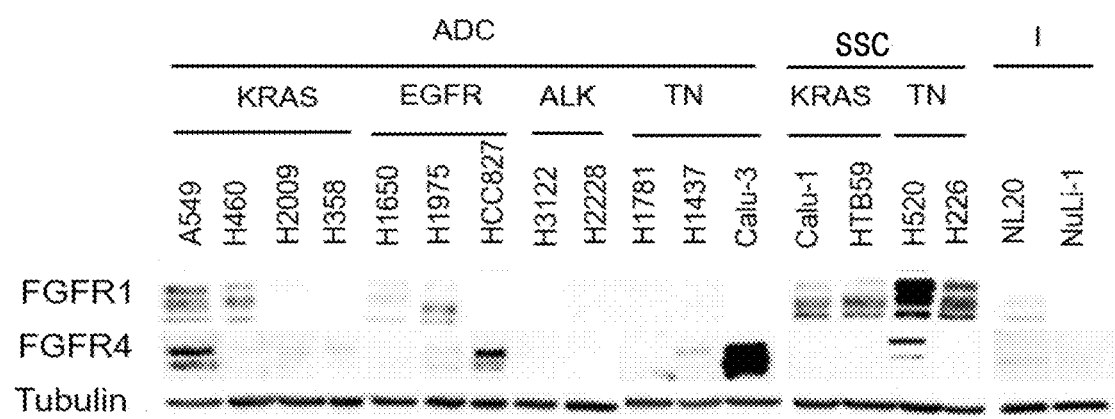
FIG. 1. Expression of FGFR1 and FGFR4 protein in lung cancer cell lines. ADC=Adenocarcinoma, SCC=Squamous cell carcinoma, I=Immortalized, KRAS=mutated KRAS, EGFR=mutated EGFR, ALK=Carriers of EML4-ALK translocations, TN=Triple negative. Tubulin is used as a load control.
Figure 2A:
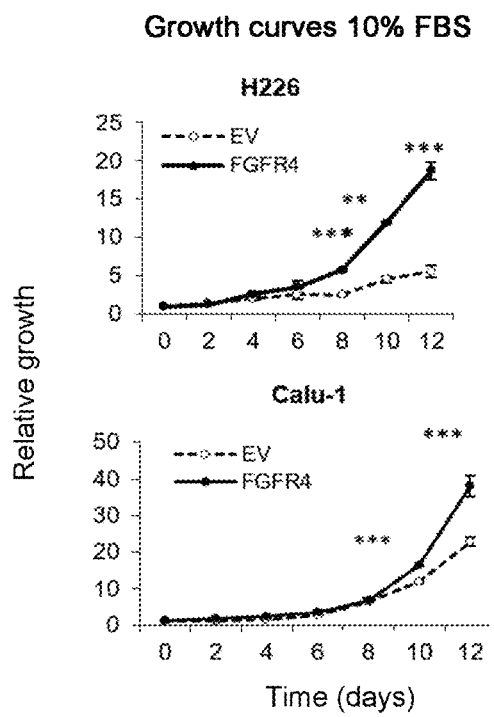
FIG. 2. Effect of FGFR4 overexpression on epidermoid carcinoma lines. Growth curves with 10% foetal bovine serum (A), clonability assay (B) and anchor-free growth assay (C). Determination of the activation of oncogenic signalling pathways (D) in the presence or absence of FBS, in squamous cell carcinoma lines under conditions of FGFR4 overexpression. EV=empty vector, FGFR4=overexpression of FGFR4, FBS=foetal bovine serum. The p-values are represented by asterisks (*, p<0.05; , p<0.01; *, p<0.001).
Figure 2B:
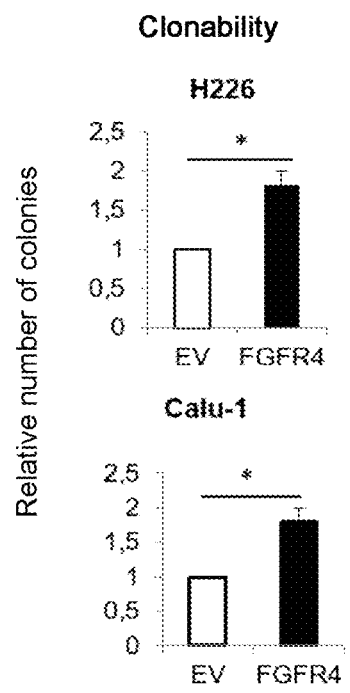
Figure 2C:
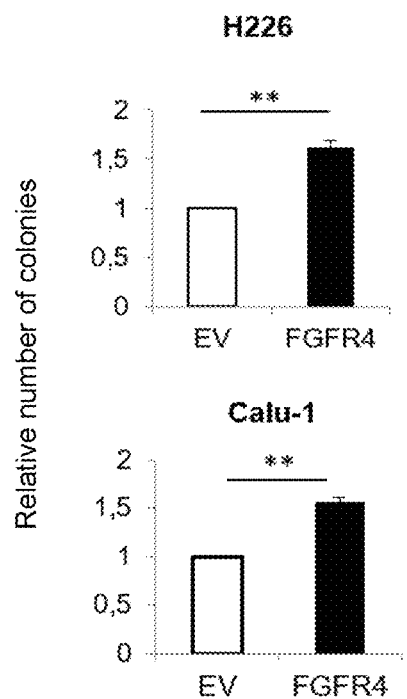
Figure 2D:
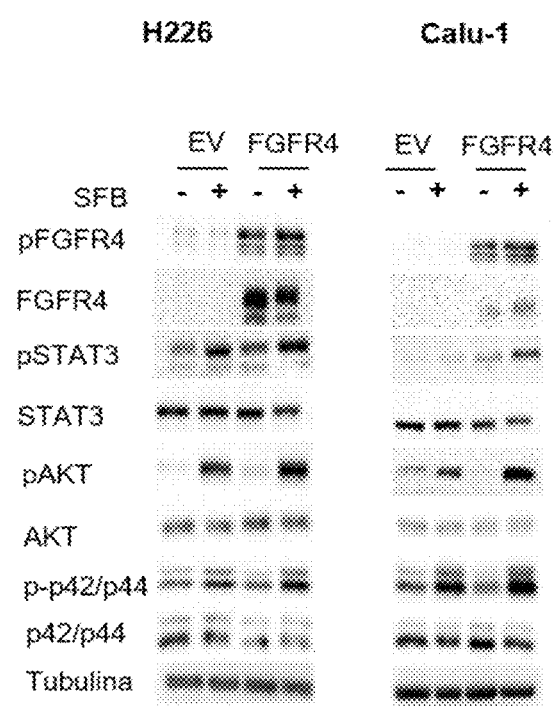

The present invention shows that the determination of the level of expression of N-cadherin and the determination of the level of expression of at least one of the biomarkers FGFR1 and/or FGFR4 improves the selection of patients for an anti-FGFR therapy in the treatment of lung cancer. The invention shows how this model predicts the response to the treatment with FGFR inhibitors in the patients, in accordance with a high expression of N-cadherin and also a high expression of at least one of the FGFRs selected from FGFR1 and/or FGFR4. The high expression of the biomarkers FGFR1 and/or FGFR4 may be due to different events occurring in the cell such as, for example, but not limited to: amplification, induction of expression at a transcriptional or translational level, gene translocations, etc.

The criteria currently employed when including patients in clinical trials with FGFR inhibitors are the amplification of a specific FGFR, or the presence of mutations or translocations in a particular FGFR. However, the only disruptions associated with a good response to these inhibitors are activating mutations or translocations, which constitute a very low percentage of patients. FGFR1 amplification has been the most widespread criterion for the inclusion of lung cancer patients in clinical trials with FGFR inhibitors. In spite of the initial description of the prevalence of this disruption being approximately 20% of epidermoid carcinomas, in practice only 5-10% of these patients present this disruption, reducing the number of patients to be included in clinical trials with these inhibitors. Furthermore, this criterion has been widely criticised due to the poor results obtained in these trials, with a very low percentage of partial responses. The results disclosed in the present invention reveal that although a tumour may have amplification and/or high expression of FGFR1 and/or FGFR4, if it does not have high expression of N-cadherin it will not respond to FGFR inhibitors. Thus, determining the expression of N-cadherin in patients with high expression of FGFR1 and/or FGFR4 will define the group of patients that will benefit from a therapy with FGFR inhibitors, thus avoiding the unnecessary treatment of patients who will not respond to the therapy, identifying the group of patients that will respond to the therapy and which, with the current criteria of patient selection (FGFR1 amplification) are not candidates for the treatment.

Definitions:

Biomarker: Any biological parameter that enables the objective measurement of the presence of a biological activity. For example, it enables the determination of whether a pharmacological treatment will be effective, or the evaluation of tolerance to a drug.

Lung cancer: A group of diseases resulting from the malignant growth of cells of the respiratory tract, in particular lung tissue. Lung cancer usually originates from epithelial cells and can lead to metastasis and infiltration to other tissues of the body. The types of lung cancer are divided into two types:

Small-cell carcinomas: These correspond to approximately 20% of lung cancers. These are located preferably in the central area of the lungs, and may compress vessels or organs located at that level. They are characterised by their high aggressiveness and rapid growth.

Non-small-cell (NSC) carcinomas: these represent the remaining 80% of lung cancers. The most frequent types are:
a) Squamous cell or epidermoid carcinoma: This is the most frequent type of bronchopulmonary cancer in Spain, representing 40% of non-small-cell carcinomas.
b) Adenocarcinoma: This represents 30% of non-small-cell carcinomas. It is the least related to tobacco use, but even so, it is more frequent in smokers.
c) Large cell carcinoma: Its name is due to the size of the cells of which it is formed. It is the least frequent type of bronchopulmonary carcinomas, representing 10% thereof.

Expression (or level of expression): For the purposes of the present invention, expression is understood to be the presence, detectable by standard techniques known in the state of the art, of a protein or a messenger RNA.

High expression: For the purposes of the present invention, high expression is understood to be the presence, detectable by standard techniques known in the state of the art, of a protein or a messenger RNA, above a reference value compared with a reference sample or in relation to the median of a reference population. To be considered that there is high expression of a biomarker, this must be at least 2 times higher than the expression of said marker in the reference sample.

Reference sample: For the purposes of this invention, it is considered that the reference sample with which the amount of protein or messenger RNA of a biomarker under analysis is compared is that which has low or no expression of said biomarker. In the present invention, but without limiting the scope thereof, the reference sample of a particular biomarker consists of the arithmetic mean of the quantification of the expression of said biomarker in at least three cell lines previously described in the state of the art because they do not express said biomarker, or because they do so at a level that has no effect on the cell. The reference sample can also be obtained from samples from one or more individuals with non-small-cell lung cancer and who do not respond to treatment with FGFR inhibitors, these may be cell lines, a cell pool, may be obtained commercially from a biobank of tissues or blood, from clinical studies published for a cohort of individuals or from reference samples recognized in the field, such as those of the TCGA cohort (The Cancer Genome Atlas of the National Cancer Institute and National Human Genome Research Institute). In this case, instead of the arithmetic mean, the median would be used. The "reference value" is considered to be the level of expression of a biomarker of the invention in the reference sample.

Overexpression: For the purposes of this invention, overexpression is understood to be the induced expression of a gene in a cell line by means of transfection with a plasmid expressing the gene of interest. Overexpression can be determined as an increase in the mRNA that encodes a given protein or an increase in the amount of protein.

Activation of a receptor: For the purposes of this invention, it is understood that a receptor is activated when it is capable of exerting its tyrosine kinase activity, triggering the specific cell signalling cascades. Activation occurs under physiological conditions when a ligand or agonist binds to the receptor. Conditions such as mutations in the receptor or the overexpression thereof, but not limited to these, can lead to a ligand-independent constitutive activation, resulting in the activation of cell signalling cascades downstream of the receptor, increasing the effect of the pathways in the cell. The constitutive activation of receptors is related to the appearance of diseases. The inhibitors of a receptor reduce or eliminate its activation, so they are commonly used as drugs in the treatment of diseases. Activating mutations have been described in the FGFR1 and FGFR4 genes, which might be involved in the tumourigenesis of lung cancer. However, it has been verified that patients who carry said mutations do not necessarily respond to a treatment with FGFR inhibitors.

For the purpose of this invention, the terms "anti-FGFR" and "FGFR inhibitor" are considered equivalent due to their concerning therapies whose effect is to reduce or eliminate the activation of FGFR receptors.

For the purposes of this invention, the terms "individuals" and "subjects" are considered synonymous and refer to any animal living being. In a preferred embodiment, the "individuals" or "subjects" in the present invention relate to human beings.

In one embodiment, the present document discloses an in vitro method for predicting the response of a subject suffering from lung cancer to a treatment with at least one FGFR inhibitor, comprising:
  a) detectiing in a biological sample obtained from said subject the expression of the N-cadherin biomarker and also the expression of at least one of the FGFR-1 and/or FGFR-4 biomarkers,
  b) comparing the level of expression of the biomarkers determined in (a) with a reference sample,
  c) administering at least one FGFR inhibitor to subjects having an expression of the biomarkers detected higher than the expression of the same biomarkers in the reference sample.

In a still more preferred embodiment, the level of expression of the N-cadherin and FGFR1 and/or FGFR4 biomarkers is determined by measuring the amount of protein of each, or by measuring the amount of mRNA of the genes respectively encoding said proteins in the sample. In a more preferred embodiment, the sequences of the biomarkers can be found in public databases with which a person skilled in the art is familiar. By way of an example and without thereby limiting the scope of the present invention, the sequence of the N-cadherin protein, also known as Cadherin-2, corresponds to UniProtKB code P19022 or NCBI reference sequence NP_001783.2 (National Centre for Biotechnology Information, US National Library of Medicine). By way of an example, and without thereby limiting the invention, the sequence of the messenger RNA of N-cadherin corresponds to the NCBI reference sequence NM_001792.4, the sequence SEQ ID NO:1 or any other that has a degree of identity therewith of at least 80%, preferably of at least 85%, more preferably of at least 90%, 95%, 96%, 97%, 98% or 99% relative to said sequence. By way of an example and without thereby limiting the scope of the present invention, the sequence of the FGFR1 protein corresponds to UniProtKB code P11362 or the NCBI reference sequence NP_075598.2. By way of an example, and without thereby limiting the invention, the sequence of the messenger RNA of FGFR1 corresponds to the NCBI reference sequence NM_023110.2, the sequence SEQ ID NO:2 or any other that has a degree of identity therewith of at least 80%, preferably of at least 85%, more preferably of at least 90%, 95%, 96%, 97%, 98% or 99% relative to said sequence. By way of an example and without thereby limiting the scope of this invention, the sequence of the FGFR4 protein corresponds to UniProtKB code P22455 or to the NCBI reference sequence NP_002002.3. By way of an example, and without thereby limiting the invention, the sequence of the messenger RNA of FGFR4 corresponds to the NCBI reference sequence NM_002011.3, the sequence SEQ ID NO:3 or any other that has a degree of identity therewith of at least 80%, preferably of at least 85%, more preferably of at least 90%, 95%, 96%, 97%, 98% or 99% relative to said sequence. The degree of identity between two sequences may be determined by conventional methods, such as, for example, BLAST (Altschul SF 1999).

In one embodiment of the invention, the lung cancer is a non-small-cell lung carcinoma. In a more preferred embodiment, the non-small cell lung carcinoma is selected from adenocarcinoma and epidermoid or squamous cell carcinoma.

In one embodiment of the invention, the sample analysed is selected from whole blood, plasma, serum, urine, sputum, sweat, bronchoalveolar lavage, or biopsy of primary or metastatic tumor tissue. In a still more preferred embodiment, the biological sample is a biopsy of the primary tumour of the subject. For the purposes of this invention, whole blood is defined as that which contains all its components, i.e., blood plasma and all formed elements (red blood cells, white blood cells and platelets). Plasma is defined as the liquid component of blood, without the cellular fraction. Serum is defined as the fluid obtained after coagulation of the blood and elimination of the clot. It differs from plasma by the absence of coagulation factors. Urine is a yellow, liquid secretion that is secreted by the kidneys as a result of the purification and filtration of blood; it accumulates in the bladder and is eliminated via the urethra. Sputum is the secretion from the nose, throat or bronchi that is ejected from the mouth in an expectoration. Sweat is the transparent fluid that the sweat glands in the skins of mammals expel through the pores. Bronchoalveolar lavage (BAL) is defined as the instillation and subsequent aspiration of fluid in one or more lung segments or subsegments. It is estimated that with the performance of the BAL, a sample of about one million alveoli (1% of the pulmonary surface) is taken, obtaining approximately 1 ml of real pulmonary secretions in the total of the fluid recovered. The biopsy is a piece of tissue or a part of organic liquid that is extracted from a living being, for diagnostic or prognostic purposes. A primary tumour tissue biopsy is a biopsy of the tumour in the place where the cancer originates, in this case the lung. A biopsy of metastatic tumour tissue refers to a lymph node biopsy obtained by a needle, or the puncture-aspiration of a tissue sample from a lymph node, or a tumour biopsy in a part of the body other than that where a cancer originally formed.

The sample can be used fresh (directly obtained from the subject) or cryopreserved or fixed in formalin or preserved in paraffin.

In one embodiment of the invention, the detection of the biomarkers may be performed by means of any method that reflects their presence, such as the detection of the biomarker in its protein form, in the case of pEGFR, FGFR1 and FGFR4, or the detection of the messenger RNA encoding said protein (or fragments thereof). Methods for the detection of this type of molecules are widely known in the state of the art. By way of an example, but not thereby limiting the scope of the present invention, the detection of the biomarkers may be carried out by means of any of the following methods: HPLC (high performance liquid chromatography), LC/MS (liquid chromatography coupled to mass spectrometry, ELISA, DAS ELISA (sandwich ELISA with double antibody), protein immunoprecipitation, immunoelectrophoresis, Western Plot, protein immunostaining, Northern Blot, reverse transcription PCR (RT-PCR), quantitative PCR (q-PCR), RIA (radioimmunoassay), in situ hybridization or nuclease protection assay, immunocytochemical or immunohistochemical techniques or any "big data" technique (massive analysis of data based on biochips or microarrays), such as genomic DNA microarrays, protein microarrays, messenger RNA microarrays, cDNA microarrays, peptide microarrays, tissue microarrays, cellular or transfection microarrays, antibody microarrays, lysate or serum microarrays, reverse phase protein microarrays, peptide microarrays or genotyping microarrays, among others. In a more preferred embodiment, the detection of the messenger RNA of the biomarkers is carried out by reverse transcription PCR (RT-PCR) or quantitative PCR (q-PCR). In one embodiment of the invention, it is considered that a biomarker is highly expressed in a sample and is usable for the prediction of the response of the subject to the treatment, if the level of the biomarkers detected in the sample is at least two times higher than the level of the same marker in a reference sample. In a more preferred embodiment, the expression of the biomarker must be at least 5 times higher than that of the reference sample. In a still more preferred embodiment, the expression of the biomarker must be at least 10 times higher than that of the reference sample.

In one embodiment of the invention, the subject suffering from lung cancer is a human being.

In another embodiment of the invention, the FGFR inhibitor employed in the treatment of lung cancer is selected from the group comprising, but without thereby limiting the scope of the invention: BGJ398, AZD4547, Debio-1347, Dovitinib, BLU9931, FIIN-2, JNJ-42756493, LY2874455, Ponatinib, BIBF1120, PD173074, PD166866, BLU554, S49076, NSC12, PHA-739358, TSU-68, BMS-540215, TKI-258, MK-2461, BMS-582664, AG 1296, SSR128129E, LY2874455 and SU5402.

The present invention also discloses the combination of the N-cadherin biomarker and at least one second biomarker selected from FGFR1 and/or FGFR4 for use in predicting the response of a subject suffering from lung cancer to treatment with FGFR inhibitors. In one particular embodiment, the level of expression of the biomarkers is selected from the level of mRNA and/or the level of N-cadherin and FGFR1 and/or FGFR4 protein.

In a preferred embodiment of the above use, the lung cancer is selected from adenocarcinoma and epidermoid or squamous cell carcinoma.

In one embodiment of the above use, the FGFR inhibitors are selected from the group comprising, but without thereby limiting the scope of the invention: BGJ398, AZD4547, Debio-1347, Dovitinib, BLU9931, FIIN-2, JNJ-42756493, LY2874455, Ponatinib, BIBF1120, PD173074, PD166866, BLU554, S49076, NSC12, PHA-739358, TSU-68, BMS-540215, TKI-258, MK-2461, BMS-582664, AG 1296, SSR128129E, LY2874455 and SU5402.

The present invention also discloses a method for predicting whether a subject suffering from lung cancer will respond to a treatment with FGFR inhibitors, comprising the use of the N-cadherin biomarker and also the use of at least one of the FGFR1 and/or FGFR4 biomarkers.

In a more preferred embodiment of the above prediction method, the levels of expression of the N-cadherin biomarker and of at least one other biomarker selected from FGFR1 and/or FGFR4 indicate that the subject will be responsive to the treatment.

In a preferred embodiment, the present invention relates to a kit for prognosing and/or predicting the response of a subject suffering from lung cancer to a treatment with FGFR inhibitors comprising:
 (a) means for detecting in a biological sample obtained from the subject the expression of the biomarker N-cadherin on the one hand, and of the expression of at least one of the biomarkers FGFR-1 and/or FGFR-4 on the other,
 (b) means for comparing the level of expression of the biomarkers determined in (a) with a reference sample,
 (c) instructions for a medical professional to administer the treatment with FGFR inhibitors solely to those subjects showing high expression of N-cadherin and also high expression of FGFR1 and/or FGFR4.

In a preferred embodiment of the kit, the means for detecting the expression of the biomarkers are selected from the group comprising antibodies for the detection of the proteins, or specific probes for detecting the messenger RNA of N-cadherin and FGFR1 and/or FGFR4, as well as reagents for carrying out said detection, such as, for instance, probes and primers that specifically recognize said messenger RNA. In one embodiment, the probes for the detection of the messenger RNA of the CDH2, FGFR1 and/or FGFR4 genes are selected from any sequence that hybridizes specifically with the RNA of these genes. By way of an example, assays of the specific TaqMan type, such as those described in Table 1 (Thermo Fisher) may be used. In a preferred embodiment, the kit comprises primers for the PCR amplification of at least part of the messenger RNA sequence encoding the N-cadherin protein, as well as primers for the PCR amplification of at least part of the messenger RNA sequences encoding the FGFR1 and/or FGFR4 proteins. The sequences of the biomarkers of the invention (messenger RNA and protein) are known in the state of the art and any average expert could design primers, probes and antibodies for their detection.

In another embodiment of the invention, regarding the kit, the antibodies used for the detection of the N-cadherin, FGFR1 and FGFR4 proteins are selected from any monoclonal or polyclonal antibody that specifically recognizes these proteins. By way of an example, the antibodies that recognize the biomarkers are those described in Table 2 of the present specification. In a preferred embodiment, the kit comprises monoclonal or polyclonal antibodies that specifically recognize the N-cadherin protein and also monoclonal or polyclonal antibodies that specifically recognize the FGFR1 and/or FGFR4 proteins. Said antibodies may or may not be marked with radioactive isotopes, enzymes, fluorophores, chemiluminescent reagents, enzyme substrates or cofactors, enzymatic inhibitors, particles, dyes, etc.

In an embodiment of the invention, regarding the kit, the means for comparing the level of expression of the specific biomarkers with a reference sample are used for the quantification of the levels of expression of the biomarkers detected previously in the biological sample and in the reference sample. The levels of expression may be quantified by any conventional method in the state of the art. By way of illustration, but not limitation of the invention, the levels of the biomarkers may be quantified, for example, by specific quantification programs linked to the aforementioned detection systems.

In an embodiment of the invention regarding the kit, the instructions for a medical professional to administer the treatment with FGFR inhibitors relate to a document or computer program which, starting from a table of values and/or data processing, indicates, on the basis thereof, if said treatment should be administered to a particular patient whose biological sample, analysed with said kit, has provided the aforementioned values and/or data.

In another embodiment, the present invention relates to a device for diagnosing and/or predicting the response of a subject suffering from lung cancer to a treatment with FGFR inhibitors, comprising the elements required for the analysis of:
 a) the level of expression of N-cadherin, and
 b) the level of expression of FGFR1 and/or FGFR4
 in a biological sample obtained from the subject suffering from lung cancer.

In a preferred embodiment, the kit or device of the invention may contain oligonucleotides designed from a known sequence or an mRNA and/or capable of hybridising with the sequence of the CDH2 gene and also the FGFR1 and/or FGFR4 genes for subsequent PCR amplification.

Preferably, the kit or device of the invention comprises at least:
 a) an anti-N-cadherin antibody and
 b) an anti-FGFR1 antibody and/or an anti-FGFR4 antibody In a preferred embodiment of said kit or device, the antibody recognizes the human protein and may be humanized or non-humanized, produced in mice, rabbits or in any other species, or synthetic. In another more preferred embodiment, the antibody is monoclonal. In another more preferred embodiment, the antibody is marked with a fluorochrome. More preferably, the fluorochrome is selected from the list comprising Fluorescein (FITC), Tetramethylrhodamine and derivatives, Phycoerythrin (PE), PerCP, Cy5, Texas, allophycocyanin or any combination thereof.

More preferably, the kit and device of the present invention comprise means necessary to compare the expression level detected with a reference sample.

The kit may also include, without any type of limitation, buffers, agents to prevent contamination, protein degradation inhibitors, etc. On the other hand, the kit may include all the supports and containers required for its start-up and optimization. Preferably, the kit also comprises the instructions for carrying out any of the methods described above.

In another embodiment, the present invention describes a method for the treatment of a subject suffering from lung cancer, comprising:
 (a) determining the presence of the N-cadherin biomarker in a biological sample obtained from said subject,
 (b) determining the presence of at least one of the FGFR1 and/or FGFR4 biomarkers in the same sample,
 (c) administering a therapeutically effective amount of the FGFR inhibitor if the subject has high expression of the biomarker N-cadherin and also has high expression of at least one of the biomarkers FGFR1 and/or FGFR4 when comparing them with a reference sample,
  wherein the determination of the presence of the biomarkers in steps (a) and (b) may be performed simultaneously or sequentially.

In another embodiment, the present invention relates to an in vitro method for diagnosing and/or predicting the response of a subject suffering from lung cancer to a treatment with FGFR inhibitors, comprising determining in a sample from the subject the expression of the biomarker N-cadherin and also determining the expression of at least one of the FGFR1 and/or FGFR4 biomarkers, comparing said expression with a reference sample, wherein the high expression of N-cadherin and also the high expression of FGFR1 and/or FGFR4 indicate that the subject suffering from lung cancer will respond to treatment.

In another embodiment, the present invention relates to the use of the biomarkers N-cadherin, FGFR1 and FGFR4 to predict whether a subject suffering from lung cancer will respond to treatment with FGFR inhibitors.

Another aspect of the invention relates to a computer-readable storage medium comprising program instructions capable of causing a computer to carry out the steps of any of the methods of the invention.

Another aspect of the invention relates to a transmissible signal comprising program instructions capable of causing a computer to perform the steps of any of the methods of the invention.

Unless defined otherwise, all the technical and scientific terms used herein have the same meaning as those customarily understood by a person skilled in the field of the invention. Methods and materials similar or equivalent to those described herein may be used in the practice of the present invention. Throughout the description and claims, the word "comprises" and its variants are not of a limiting nature and therefore do not intend to exclude other technical characteristics, additives, components or steps. The term "comprises" also includes the term "consists of".

This invention demonstrates for the first time that the pro-oncogenic function of the FGFR1 and FGFR4 genes in lung cancer depends on the expression of N-cadherin protein. In the absence thereof, both genes generally present a tumour-suppressive role. A high expression of FGFR1 in models of xenografts derived from lung cancer patients reveals that the efficacy of a selective FGFR inhibitor is only evident in patients with high expression of N-cadherin. In all the above embodiments of the invention or group of inter-related inventions, it should be interpreted that "high expression of N-cadherin", "high expression of FGFR1" and "high expression of FGFR4" refer to said expression being, at least, 2 times higher than the expression of the same biomarkers in a reference sample.

EXAMPLES

Materials and Methods
Analysis of Gene Expression
RNA Extraction

For the extraction of the RNA from the cell lines, the Trizol reagent (Life Technologies) was used, following the manufacturers instructions. Subsequently, the RNA was precipitated with isopropanol, washed with 75% ethanol and resuspended in DEPC water (water treated with diethylpyrocarbonate).

For the extraction of total RNA from tissue fixed with formalin and preserved in paraffin, the sheets of tumour tissue were dewaxed with Xylol. Total RNA was extracted using the RecoverAll extraction kit (Life Technologies), following the manufacturers instructions for the extraction of RNA from biological tissue.

Once the RNA was extracted, its concentration was quantified using the NanoDrop equipment (ThermoScientific) and stored at −80° C. for later use.

RNA Retrotranscription

The RNA samples were retrotranscribed using the "TaqMan Reverse Transcription" retrotranscription kit (Life Technologies), following the manufacturers instructions. In each reaction, 1000 ng of RNA was used in 10 μL, with 10 μL of master mix, in a final volume of 20 μL. The reactions were subjected to the thermocycling protocol for 10 minutes at 25° C., 120 minutes at 37° C. and 5 minutes at 85° C.

Pre-Amplification of the cDNA

The RNA extracted from the waxed tissue was pre-amplified using the "TaqMan Preamp Master Mix" kit (Applied Biosystems), following the manufacturers instructions. The final volume of the amplification reaction was 10 μL and 100 ng of total cDNA was added per reaction. We used the 14-cycle pre-amplification protocol described in the manufacturers instructions (10 minutes at 95° C., 14 cycles of: 15 seconds at 95° C. and 4 minutes at 60° C.). After pre-amplification, the samples were diluted 1:20 prior to carrying out the quantitative PCR.

Real-Time Quantitative PCR

Each real-time PCR reaction was performed in triplicate, according to the protocol indicated by the manufacturer for the Taqman probes (ThermoFisher) and the TaqMan master mix for qPCR (ThermoFisher). The final volume of each reaction was 10 μL, containing 5 μL of the master mix, 2.5 μL of the TaqMan probe of the gene under study and 2.5 μL of the cDNA sample. The concentration of the cDNA samples was 25 ng/μL in the case of non-pre-amplified samples. In previously pre-amplified samples, 2.5 μL of the 1:20 dilution of the pre-amplification reaction was used. In addition, a negative control without a cDNA sample was performed for each probe, to rule out contaminations in the water, in the master mix or in the probe. A thermocycling protocol of 40 cycles was followed (10 minutes at 95° C., 40 cycles of: 15 seconds at 95° C. and 1 minute at 60° C.).

The relative quantification of mRNA expression is determined from the Ct values obtained in the reaction, defining Ct as the number of the cycle in which an amplification signal of the target gene above a predetermined threshold is detected, which makes it possible to discern between a real amplification signal and noise. For each sample, the average of three technical replicates for each gene was calculated, and this mean Ct value was standardised with the Ct of the endogenous load control gene (glyceraldehyde-3-phosphate dehydrogenase, GAPDH, for cell line extracts and Beta-2-microglubin, B2M, for tumour extracts), obtaining the ΔCt value. The expression levels were represented in the $2^{-\Delta Ct}$ form, which is more intuitive because higher $2^{-\Delta Ct}$ values indicate higher expression of the gene.

In the case of the determination of mRNA expression in extracts from cell lines, the mean and standard deviation of the $2^{-\Delta Ct}$ values from three independent biological replicates were calculated. The assays used in preamplification and in the determination of mRNA expression are described in Table 1.

TABLE 1

Assays used for the determination of the mRNA expression of the gene of interest.

| Target gene | Reference | Supplier |
|---|---|---|
| FGFR1 | Hs00917379_m1 | Life technologies |
| FGFR4 | Hs01106908_m1 | Life technologies |
| N-cadherin | Hs00983056_m1 | Life technologies |
| E-cadherin | Hs01023894_m1 | Life technologies |
| B2M | Hs99999907_m1 | Life technologies |
| GAPDH | Hs99999905_m1 | Life technologies |

Protein Analysis

To determine the expression of proteins in the samples, the total proteins were first extracted. The cells of the cell lines were washed twice with PBS, and lysis buffer (RIPA (Sigma) was added, supplemented with a cocktail of protease inhibitors (complete Mini EDTA-free, Roche) and a cocktail of phosphatase inhibitors (PhosSTOP EASYpack, Roche) at the concentration recommended by the manufacturer. The cell lysates were collected by scraping on ice and were added to a tube. The cell remnants were eliminated by centrifuging at 15,000×g for 10 minutes at 4° C. and the supernatant (protein extract) was stored in aliquots at −80° C. The quantification of protein extracts was performed using the modified Bradford method (BioRad), according to the manufacturers instructions, using known concentrations of serum albumin (BSA) as a control.

The total proteins of the tumours from xenografts were obtained by adding the lysis buffer to the previously pulverized tissue fragment in a mortar pre-cooled with liquid nitrogen, to avoid thawing the fragment; it was then incubated on ice for 2 hours, stirring every 10 minutes, and the volume was collected in 2 mL tubes that were centrifuged at 15,000×g for 10 minutes at 4° C. to eliminate the remnants of undissolved tissue, and the supernatant was stored at −80° C. The extraction buffer and the quantification method used were the same as in the case of protein extraction from cell lines.

Western Blot 5X loading buffer (62.5 mM Tris-HCl pH 6.8, 10% glycerol, SDS 1%, 2-mercaptoethanol 5%, bromophenol blue 0.0025% (Sigma)) was added to the samples and these were denatured for 5 minutes at 95° C. They were then loaded in the electrophoresis gel to perform the western blot, or stored at −20° C.

Protein immunodetection was performed according to a standard protocol on PDVF membranes (GE Healthcare). The proteins were separated on SDS polyacrylamide gels using a 1X Tris HCl 0.13 M electrophoresis buffer, 0.95 M glycine, 0.5% SDS, and were transferred to PDVF membranes, using a Trans-Blot Turbo kit (BioRad). The transfer was performed at 400 mA for 3 hours in transfer buffer (0.025 M TrisHCl, 0.2 M glycine, 20% methanol). The membranes were blocked for 1 hour under stirring with the blocking buffer (TBS, 0.1% Tween20 and 1% BSA). Subsequently, the membranes were incubated with the appropriate dilution of primary antibody for 16 hours at 4° C. After this incubation, the membranes were washed with washing buffer (TBS 0.1% Tween-20) and incubated with a 1:5,000 dilution of the appropriate peroxidase-conjugated secondary antibody, for one hour at ambient temperature. The detection was performed using a chemiluminescent reaction (Clarity ECL, Biorad) and visualization using luminescence detection equipment (ChemiDoc, BioRad).

The antibodies used in the assays described herein are listed in Table 2.

To quantify the bands detected in the western blot assays, the software included in the chemiluminescence detection equipment (ImageLab, BioRad) was used. The volume of the band of the protein of interest was quantified and was standardised with the volume of the band corresponding to the gene of constitutive expression, which served as a load control (alpha tubulin, also called tubulin).

The reference value of a biomarker in a reference sample is calculated from the value of the quantification of its expression in three cell lines that do not express, or have an expression level that has no effect on the cell. The values of this quantification are standardised as stated above and the arithmetic mean of the standardised expression of the biomarker in the three cell lines is calculated. In the case of the FGFR1 and FGFR4 biomarkers, the expression of the reference sample was calculated from the cell lines H2009, H358 and H1650. In the case of N-cadherin, the reference sample was calculated from the expression of the biomarker in cell lines A459, H460 and H2009.

TABLE 2

Antibodies used to determine protein expression of proteins of interest

| Target protein | Antibody type | Molecular weight | Ref. | Supplier | Western blot dilut. | Immunofl. dilut. |
|---|---|---|---|---|---|---|
| FGFR1 | Rabbit mon. | 150 kDa | 9740 | CST | 1:1000 | 1:100 |
| FGFR4 | Rabbit mon. | 100 kDa | 8562 | CST | 1:1000 | 1:100 |
| pFGFR1 (Tyr653/654) | Rabbit pol. | 150 kDa | 06-1433 | Millipore | 1:2000 | — |
| pFGFR4-Tyr642 | Rabbit pol. | 100 kDa | MBS856043 | MyBiosource | 1:2000 | — |
| AKT | Rabbit pol. | 60 kDa | 9272 | CST | 1:1000 | — |
| pAKT (Ser473) | Rabbit pol. | 60 kDa | 9271 | CST | 1:1000 | — |
| p42/p44 (ERK1/2) | Rabbit pol. | 42/44 kDa | 9102 | CST | 1:1000 | — |
| p42/p44 (ERK1/2) (Thr202/Tyr204) | Rabbit pol. | 42/44 kDa | 9101 | CST | 1:1000 | — |
| STAT3 | Mouse mon. | 80 kDa | 9139 | CST | 1:1000 | — |
| pSTAT3-Tyr705 | Rabbit pol. | 80 kDa | 9145 | CST | 1:1000 | — |
| N-cadherin | Rabbit mon. | 135 kDa | 13116 | CST | 1:1000 | — |
| N-cadherin | | 135 kDa | | ThermoFisher | — | 1:100 |
| E-cadherin | Rabbit mon. | 125 kDa | 3195 | CST | 1:1000 | — |
| α-Tubulin | Mouse mon. | 55 kDa | T9206 | Sigma | 1:5000 | — |
| Anti-rabbit secondary (HRP) | Goat pol. | | 7074 | CST | 1:5000 | — |
| Anti-mouse secondary (HRP) | Horse pol. | | 7076 | CST | 1:5000 | — |
| Anti-rabbit sec. (Alexa Fluor 488) | Goat pol. | | R37116 | ThermoFisher | — | 1:250 |
| Anti-mouse sec. (Alexa Fluor 555) | Donkey pol. | | A-31570 | ThermoFisher | — | 1:250 |

Mon = monoclonal antibody. Pol = polyclonal antibody. Mol weight = molecular weight. Ref = reference. Dilut = dilution. Immunofl = immunofluorescence. HRP = horseradish peroxidase.

Cell Biology

The cell line panel used contains two immortalised lung cell lines, four epidermoid lung carcinoma lines and thirteen adenocarcinoma lines, the characteristics whereof are shown in Table 3.

TABLE 3

Lung cell lines

| Cell line | Histological Type | Driver mutation described | Ref. | Culture medium |
|---|---|---|---|---|
| A549 | ADC | KRAS p.G12S | Helfrich 2006 | DMEM supplemented with sodium pyruvate, HEPES and non-essential amino acids |
| H460 | ADC | KRAS p.Q61H | Helfrich 2006 | RPMI 1640 |
| H2009 | ADC | KRAS p.G12A | COSMIC | RPMI 1640 |
| H358 | ADC | KRAS p.G12C | Helfrich 2006 | RPMI 1640 |
| H1650 | ADC | EGFR E746-E750 del | White 2009 | RPMI 1640 |
| H1975 | ADC | EGFR L858R/T790M | COSMIC | RPMI 1640 |
| HCC827 | ADC | EGFR E746-E750 of | Helfrich 2006 | RPMI 1640 |
| H3122 | ADC | EML4-ALK v1 translocation | COSMIC | RPMI 1640 |

TABLE 3-continued

Lung cell lines

| Cell line | Histological Type | Driver mutation described | Ref. | Culture medium |
|---|---|---|---|---|
| H2228 | ADC | EML4-ALK v3 translocation | COSMIC | RPMI 1640 |
| H1781 | ADC | | | |
| H1437 | ADC | | | |
| Calu-3 | ADC | TN | Helfrich 2006 | DMEM |
| Calu-1 | SCC | KRAS p.G12C | COSMIC | McCoy's 5a |
| HTB59 | SCC | KRAS p-G12V | COSMIC | McCoy's 5a |
| H520 | SCC | TN | COSMIC, Helfrich 2006 | RPMI 1640 |
| H226 | SCC | TN | COSMIC, Helfrich 2006 | RPMI 1640 |
| NL20 | I | TN | COSMIC | F12 supplemented following directions from ATCC |
| NuLi-1 | I | TN | COSMIC | LHC9 |

ADC = Adenocarcinoma, SCC = Squamous cell carcinoma, TN = Triple negative (nomenclature referring to cell lines without disruptions in KRAS, EGFR or ALK), I = Immortalized.

Cell Line Culture

The cell lines, with the exception of A549, were cultured following the directions from the ATCC, supplementing all the media with 40 u/mL of penicillin (Sigma), 40 µg/mL of streptomycin (Sigma) and 1 µg/mL of amphotericin B (Sigma) and with glutamine (Sigma) in the case of the media that did not include stable glutamine in their composition. A549 was cultured in DMEM medium supplemented with HEPES 0.01M (Sigma), sodium pyruvate 1 mM (Sigma), and non-essential amino acids 1X (Sigma), in addition to the aforementioned supplements. The cells were cultured on 10 cm plates and subcultured at 1:4 every 2-3 days by means of trypsin treatment. The manipulation of the cell lines was carried out in a laminar flow booth of the II-Bio-II-A type (biosafety level 2) and their culture was carried out in incubators (ThermoScientific, Series 8000 Water-Jacketed $CO_2$ Incubators) at 95% relative humidity and 5% $CO_2$.

Assays in which the cell lines were stimulated with foetal bovine serum (FBS) were seeded and upon reaching 60-70% confluence, were incubated for 5 hours with medium without FBS. Then, on the one hand, protein extracts corresponding to the baseline state were obtained, and, on the other hand, the stimulation was carried out with 10% FBS. The cells were stimulated for 15 minutes and then the protein was extracted (explained above).

Cell Transfection

The cell lines were transfected with the plasmids described in Table 4. To this end, TransIT-X2 transfection reagent (Mirus) was used, following the manufacturers instructions. 24 hours before transfection, the cells were seeded on 6-well plates, in search of approximately 40% confluence in each well for the day of transfection. Before transfection, the cell medium was changed by adding 2.5 mL of medium. Next, the transfection particles were added to the DNA and the cells were incubated therewith for 72 hours. After this time, the cells were transferred to 10-cm plates and, once adhered to the plate (after about 24 hours), fresh medium was added with the selected antibiotic at the appropriate concentration. As a negative control of the transfection, a plate was used with the untransfected cell line also exposed to the selection medium. During the process of selection of the transfected cells (3 or 4 weeks), the antibiotic culture medium was renewed 3 times per week. After this period, it was verified that in the negative control no cells survived. The generated colonies were trypsinized and reseeded on a new plate, establishing a pool of the different transfected clones, with which a stable transfected cell line was constituted. In the line generated, the overexpression or silencing performed according to the examples described below was confirmed, and cryopreservation was performed. During the cultivation of the lines generated, these were maintained in the presence of selection antibiotic at half the concentration of that used during the selection. In each transfection, the appropriate antibiotic was used according to the plasmid transfected at the appropriate concentration according to the cell line (Table 5): puromycin (Calbiochem), blasticidin (Sigma) or G418 (Santa Cruz). In the case of transfections with plasmids with a reporter gene (GFP), the cells were amplified and subsequently those transfected were separated by means of a cell separator by flow cytometry using the BD LSRFortessa (BD) equipment.

In the case of transfections of interference RNAs ("short hairpin shRNAs", shRNAs), two stable cell lines were generated with silencing of the expression of the gene of interest, using in each a different shRNA, in order to ensure that the the effects observed were not derived from the unspecific silencing of the expression of a different gene. The transfection was carried out using the plasmids pRS (puromycin) or pB-RS (blastomycin), in accordance with Table 4.

In the case of co-transfections of more than one plasmid in the same cell line, the transfections were performed independently and subsequently. The selection antibiotics of the transfected plasmids were maintained in the medium at the maintenance concentration in order to maintain a selective pressure, combining two or three antibiotics. The only time that the selection antibiotics were not present was during the incubation period of the cells with the transfection reagent (72 hours), since these could interfere with the transfection, reducing its efficacy.

TABLE 4

Plasmids used in the tests

| Name | Vector | Selection method | Ref. | Supplier | Use |
|---|---|---|---|---|---|
| pCMV6 | pCMV6 | G418 | PS100001 | Origene | Control overexpression of FGFR1 and FGFR4 |
| pCMV6-FGFR1 | pCMV6 | G418 | RC202080 | Origin | Overexpression of FGFR1 |
| pCMV6-FGFR4 | pCMV6 | G418 | RG204230 | Origene | Overexpression of FGFR4 |
| pRS scramble shRNA | pRS | Puromycin | TR20003 | Origene | Control of FGFR1 and FGFR4 silencing |
| pRS-shRNA-FGR1 | pRS | Puromycin | TR320354 | Origene | Silencing by FGFR1 shRNA |
| pRS-shRNA-FGFR4 | pRS | Puromycin | TR320356 | Origene | Silencing by FGFR4 shRNA |
| PL-SIN-PGK-EGFP | PL-SIN-PGK | GFP | #21316 | Addgene | Control of N-cadherin overexpression |
| pCCL-c-MNDU3c-PGK-EGFP-N-cadherin | pCCL-c-MNDU3C-PG | GFP | #38153 | Addgene | N-cadherin overexpression |
| pB-RS | pB-RS | Blasticidin | TR30024 | Origene | Control of N-cadherin and E-cadherin silencing |
| pB-RS shRNA N-cadherin | pB-RS | Blasticidin | HC138304 | Origene | N-cadherin silencing |
| pB-RS shRNA E-cadherin | pB-RS | Blasticidin | HC138277 | Origene | E-cadherin silencing |

The control vectors correspond to the empty vectors.

TABLE 5

Concentrations of antibiotics used.

| Cell line | G418 | Puromycin | Blasticidin |
|---|---|---|---|
| A549 | | 2 ug/mL | |
| H460 | 2 mg/mL | | |
| H2009 | 1 mg/mL | | 3 ug/mL |
| H1650 | 1 mg/mL | | |
| H1975 | 1 mg/mL | | |
| HCC827 | 1 mg/mL | | |
| H3122 | 2 mg/mL | | 3 ug/mL |
| Calu-3 | | 2 ug/mL | |
| Calu-1 | 1 mg/mL | | |
| H520 | | 2 ug/mL | 2 ug/mL |
| H226 | 1 mg/mL | | |
| NL20 | 1 mg/mL | 1 ug/mL | 2 ug/mL |

Tumorigenicity Assays

The tumorigenicity assays were repeated a minimum of three times in order to confirm the results. In addition, as part of each repetition of the experiment, each condition was seeded in triplicate.

a) Growth Curve 3,500 cells were seeded per well in 12-well plates. At 24 hours (day 0) the cells of the first point of the curve were fixed, and every 24-48 hours a new point of the curve was fixed and the medium of the rest was changed. The fixed plates were preserved with the cells in PBS at 4° C. until all the points of the curve were fixed. The plates were then stained with crystal violet for 20 minutes, washed and allowed to dry. Once dry, 20% acetic acid was added to each well to dilute the crystal violet, and the absorbance at 595 nm was measured on a VICTOR optical reading device (PerkinElmer). All absorbances were standardised in relation to the absorbance of day 0 of each experimental condition. Finally, this standardised value (growth relative to day 0 on the Y-axis) was plotted against time (days, X-axis).

b) Clonability Assay

A number of cells of between 1,000 and 5,000 cells were seeded, according to the cell line, on 10-cm plates. The medium was renewed once per week for 2 or 3 weeks, depending on the cell line. After this time, the cells were fixed with a solution of glutaraldehyde in 0.5% PBS for 20-30 minutes and stained with a 1% solution of crystal violet in water. After washing and drying the plates, the number of colonies was quantified.

c) Anchor-Free Growth (Soft Agar Assay)

100,000 cells/well were resuspended in medium with 0.35% agarose, which was seeded on a base of medium with 0.7% agarose previously solidified in 6-well plates. After 24 hours, 3 mL of complete medium was added to each well, which was renewed twice a week. After one or two months, depending on the line under assay, photos were taken of the colonies by means of a microscope (#IX2-SLP, Olympus) with an integrated camera (#U-CMAD3, Olympus). In these photos, the number of colonies was quantified and their size was determined. The result is represented in a graph showing the relative number of colonies (with respect to time 0) of the cells that overexpress or inhibit the expression of a gene compared with the control cells, transfected with the empty vector. It was determined whether the difference in the relative number of colonies with respect to the control is statistically significant (* p-values less than 0.05,  p-values less than 0.01, and * p-values less than 0.001).

Co-Immunolocalization

The cells were seeded on sterile coverslips and fixed with a 4% paraformaldehyde solution in PBS for 15 minutes. After two washes with PBS, the cells are waterproofed with a 0.1% solution of Triton X-100 in PBS for 5 minutes. They are then incubated for one hour in blocking solution (PBS, 0.1% Triton X-100, 1% SAB) at ambient temperature. Subsequently, they are incubated at the appropriate dilution in primary antibody blocking solution, for 3 hours at ambient temperature. After three washes with 0.1% Triton X-100 PBS of 5 minutes duration and under stirring, the cells were incubated with the secondary antibody at the appropriate dilution, in blocking solution, for 1 hour at ambient temperature. In a confocal microscope (SP5-WLL), photos are taken of at least 20 cells per experimental condition in different replicas of the experiment to analyse the co-localization of the proteins under study.

Co-Immunoprecipitation of Membrane Proteins

Total proteins were extracted as described above, but using a 50 mM HEPES extraction buffer, 150 mM NaCl and 1% n-octylglucoside, supplemented with a cocktail of protease inhibitors (cOmplete Mini EDTA-free, Roche) and phosphatases (PhosSTOP EASYpack, Roche). The total protein concentration of the extracts was quantified as previously indicated and aliquots of 2 mg were prepared. In these aliquots, protein pre-clearance was performed by incubation with 10 µL of EZ View Red Protein G Affinity Gel (Sigma) resin, which was used as an immunoprecipitation substrate for 2 hours at 4° C. under gentle stirring. The resin was then removed by centrifuging at 6000 g at 4° C. for 1 minute. In parallel to the pre-clearance, the resin was conjugated with the primary antibody against the protein to be immunoprecipitated (anti-N-cadherin, described in Table 2), incubating 10 µL of resin with 2 µg of antibody for each mg of protein in the sample in lysis buffer at 3% of bovine serum albumin (BSA), for 2 hours under gentle stirring at 4° C. As a negative control of the immunoprecipitation, an aliquot of the protein sample incubated with particles conjugated to a non-specific antibody of the same isotype as the antibody against the protein of interest was used, at the same concentration. Next, three washes of the resin conjugated with the antibody were performed with lysis buffer, centrifuging between washes for 1 minute at 6000 g at 4° C. to remove the used buffer and to add new buffer. Subsequently, the resin conjugated with the antibody was incubated with the sample for 16 hours under gentle stirring at 4° C. Then, 5 washes of the resin with the immunoprecipitate were carried out by resuspending it in lysis buffer and subsequently centrifuging for 1 minute at 6000 g at 4° C. The supernatant was discarded, 20-30 µL of lysis buffer was added together with 5X loading buffer, as indicated above. The samples were boiled for 5 minutes at 95° C. and centrifuged at 12,000 g for 3 minutes. The supernatant was used to perform a western blot as described above, to detect by means of specific anti-N-cadherin, anti-FGFR1 and anti-FGFR4 antibodies, the presence of biomarkers in each stage of the immunoprecipitation. Thus, it may be detected whether there are biomarkers that co-immunoprecipitate with N-cadherin, indicating a binding in the cell membrane. As immunoprecipitation controls, two aliquots of the protein extract were preserved, one prior to and one subsequent to the immunoprecipitation.

Animal Experimentation Techniques

All the procedures performed with animals were approved by the Animal Protection Committee of the Autonomous Community of Madrid (PROEX134/16).

a) Xenografts with Cell Lines in Immunocompromised Mice

The cells of the cell line to be xenografted were counted and a final concentration of 2 million cells in 100 µL of PBS was prepared. Next, a solution of Matrigel (BD #356234) was added to the cell suspension at a ratio of 1:1, and 200 µL was injected subcutaneously into both flanks of immunocompromised nude mice of 5-6 weeks of age, under anaesthesia by isofluorane inhalation.

b) Xenografts of Tumors Derived from Patients (PDXs)

Tumours from patients with non-small cell lung cancer, covered with Matrigel (BD #356234) are implanted in the flank of immunocompromised nude mice of 5-6 weeks of age, under anaesthesia by isofluorane inhalation and under analgesia by buprenorphine. To perform the implant, a small cut is made in the flank of the mouse under anaesthesia and analgesia and the tumour fragment is inserted, about 100-150 mm$^3$ in volume.

c) Determination of the Tumour Growth of the Xenografts

The size of the tumours generated by the xenografts was measured weekly with a measuring gauge. The shortest and longest length of each tumour was measured and the tumour volume was calculated with the formula: $0.5 \times (\text{longest dimension}) \times (\text{shortest dimension})^2$.

The median of the standardised tumour volumes was plotted against time. This was calculated by standardising the tumour volume of each measurement to the first measurement made (7 days after implantation). The median error was calculated with the formula: standard deviation $/\sqrt{n}$, where n is the number of tumours in each group.

Once the tumours reached 1000 mm$^3$ in volume, the mice were sacrificed and the tumours removed. The tumour samples were sliced and quickly frozen in cryotubes, for preservation at −80° C. and subsequent extraction of RNA or protein.

d) PDX Treatments

Treatments were performed with the selective FGFR inhibitor AZD4547 to verify its effect on the growth of the tumours (PDXs). For this purpose, the model of interest was implanted in 4-6 mice per treatment group as stated above, and the growth of the tumours generated was monitored. When the tumours had reached a volume of between 100 and 150 mm$^3$, the mice were distributed in the different treatment groups, including in each group those whose tumour size had a similar median and standard deviation, and leaving a control group treated with the vehicle as a reference. Once the groups were established, the treatments were commenced, lasting between 3 and 5 weeks, depending on the growth rate of each model and on the drug or drugs employed.

The concentration of AZD4547 employed was 7.5 mg/kg/day, administered from Monday to Friday. The route of administration of the drug was oral. At the end of the treatment, the mice were sacrificed and the tumours processed and stored as stated above.

The growth of the tumours is shown in graphs of tumour growth against time, where each measurement of tumour volume is relativised with the initial measurement after commencing the treatment, and the median and mean error are shown for each treatment group. The variation in tumour volume is represented with bar graphs which show the increase (or decrease), expressed as a percentage, of the volume of each tumour with regard to the initial volume in each treatment group Statistical Analysis Statistical analyses were performed using the statistical software package SPSS (IBM), applying the statistical tests detailed below to obtain the p-values. Those below 0.05 were considered statistically significant and these values were plotted as * for p-values <0.05,  for p-values <0.01 and * for values <0.001.

a) Analysis of In Vitro and In Vivo Experiments

To analyse whether the differences found between the different conditions tested in the in vitro experiments are statistically significant, the nonparametric Mann-Whitney U test was performed, in the values corresponding to the independent biological replicas of the experiments.

In order to analyse whether the growth differences of the tumours of the different experimental conditions in the in vivo tests reached statistical significance, the same test was performed in the values corresponding to the standardised values of the tumour sizes.

b) Analysis of Clinical Cohorts

Regarding the clinical data, the Kaplan Meier method was used for the survival analysis, using the Log-Rank and the Cox models of proportional risks to adjust the explanatory variables and obtain the p-values. Overall survival was defined as the time period between diagnosis and the last clinical review or death and progression-free survival was defined as the period between the initial diagnosis and the diagnosis of recurrence.

Example 1. Effect of the Expression of the FGFR1 and FGFR4 Genes in Tumourigenesis in Squamous Cell Lung Carcinoma To verify the effect of FGFR1 and FGFR4 in lung cancer, the effect of the overexpression and silencing of these genes was analysed in different lung cancer cell lines.

First, the endogenous expression of FGFR1 and FGFR4 was analysed in the 18 different cell lines described in Table 3. 16 cell lines are of non-small-cell lung cancer from the two most representative histologies of this pathology, adenocarcinoma and squamous cell or epidermoid carcinoma. Cell lines were selected with the different molecular disruptions of greatest therapeutic relevance in lung cancer (mutation in KRAS, mutation in EGFR, EML4-ALK translocation or lines without any of the aforementioned disruptions, which we will call "triple negative"), and two immortalized lung cell lines.

The expression of FGFR1 and FGFR4 at protein level was determined. To this end, the total proteins were extracted from the cell lines, denatured and the presence of FGFR1 and FGFR4 was detected by western blot using the anti-FGFR1 and anti-FGFR4 monoclonal antibodies described in Table 2. Tubulin was used as load control.

As may be seen in FIG. 1, the protein expression of FGFR1 in the adenocarcinoma (ADC) cell lines is low, in comparison with the epidermoid (SCC) carcinoma lines. The protein expression of FGFR4 is less frequent and is not representative of any of the histological types under study.

Next, the bands detected in the western blot assay were quantified, as described in the materials and methods herein. As a reference sample to evaluate the expression of FGFR1 and FGFR4, the average of the expression of these receptors standardised with tubulin was used in the H2009, H358 and H1650 cell lines. In the case of N-cadherin, the reference sample was the average of the biomarker expression standardised with tubulin in cell lines A459, H460 and H2009.

TABLE 6

Quantification of the expression of the biomarkers in the reference samples

| | Cell line | Standardised expression with tubulin | Standard deviation | Reference value |
|---|---|---|---|---|
| FGFR1 | H2009 | 0.13 | 0.16 | 0.557 |
| | H358 | 0.22 | 0.11 | |
| | H1650 | 1.32 | 0.35 | |
| FGFR4 | H2009 | 0.23 | 0.21 | 0.163 |
| | H358 | 0.17 | 0.09 | |
| | H1650 | 0.09 | 0.05 | |
| N-cadherin | A549 | 3.37 | 1.45 | 1.25 |
| | H460 | 0.22 | 0.14 | |
| | H2009 | 0.16 | 0.11 | |

To determine the role of FGFR4 in the epidermoid carcinoma cell lines, the epidermoid carcinoma H226 (triple negative) and Calu-1 (mutated KRAS) cell lines were selected for the overexpression therein of the FGFR4 gene. The overexpression of the FGFR4 gene was carried out by transfecting the cell lines with the pCMV6-FGFR4 plasmid described in Table 4. Next, the cells were cultured and the tumourigenic characteristics of the samples were analysed by means of growth curves, soft agar assays and analysis of the expression of the pro-oncogenic signalling pathways.

FIG. 2 shows the relative growth of the H226 epidermoid lung carcinoma (above) and Calu-1 (below) cell lines over time. It may be observed how the samples overexpressing FGFR4 have a greater cell growth (FIG. 2A), clonability (FIG. 2B) and capability of generating anchor-free growth colonies (FIG. 2C) than the control lines (transfected with the empty vector (EV)). The overexpression of this gene induces its own overactivation, in addition to that of different pro-oncogenic signalling pathways, as revealed by the expression of the pSTAT3, pAKT and p-p42/p44 proteins (FIG. 2D). All the tests were performed at least in triplicate. Representative growth curves are shown. For the clonability and the anchor-free growth test, the mean and standard deviation of the replica colonies are shown, after standardisation with the control condition, which takes the value of 1. For the anchor-free growth test, the mean and standard deviation of the size of the colonies is also shown. The p-values were obtained by means of Student's T-test with a confidence interval of 95%; the p-values below 0.05 are represented as *, the p-values below 0.01 as , and the p-values below 0.001 as *.

In order to investigate in greater depth the pro-oncogenic effect of FGFR1 and FGFR4 on the tumourigenic properties of the epidermoid carcinoma cell lines, the expression of FGFR1 and FGFR4 was silenced independently in a line with high endogenic expression of both genes, the H520 line (FIG. 1). Silencing of the genes was performed as described in the Materials and methods presented herein, using the pRS shRNA scramble vector as control, and the pRS-shRNA-FGFR1 and pRS-shRNA-FGFR4 vectors for the silencing of the FGFR1 and FGFR4 genes respectively.

Figure 3A:
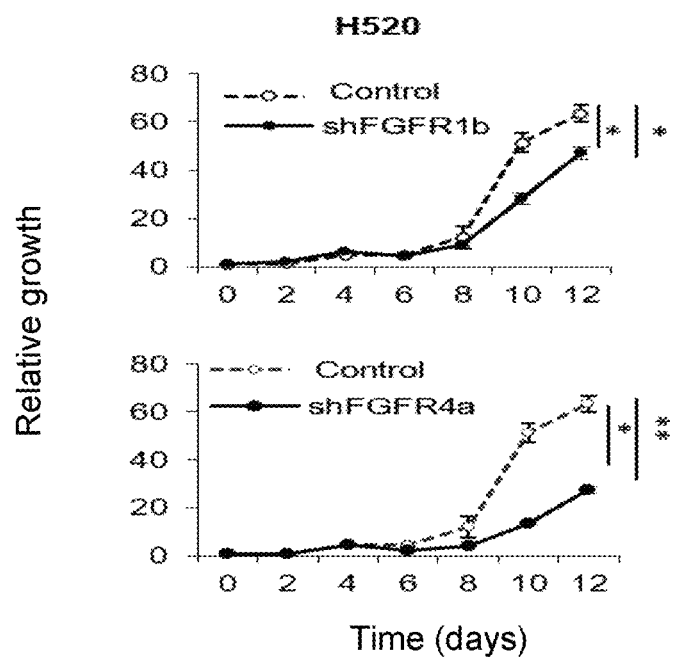
FIG. 3. Effect of FGFR1 or FGFR4 silencing in an epidermoid carcinoma line. Growth curves at 10% FBS (A), clonability (B) and anchor-free growth (C). Analysis of the activation of FGFR-related signalling pathways (D) in the presence or absence of FBS. Control=unspecific shRNA, as control, shFGFR1=shRNA FGFR1, shFGFR4=shRNA FGFR4, FBS=Foetal bovine serum. Samples (a) and (b) correspond to two independent shRNAs to silence the same gene. The p-values are represented by asterisks (*, p<0.05; , p<0.01; *, p<0.001).
Figure 3B:
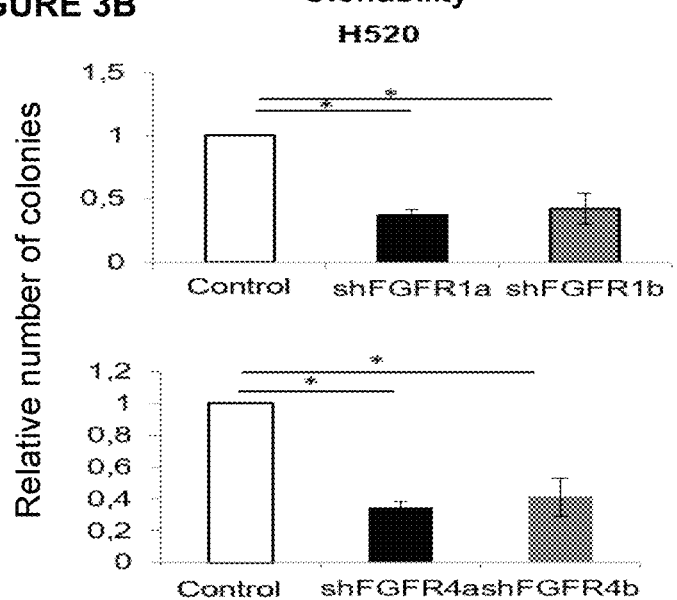
Figure 3C:
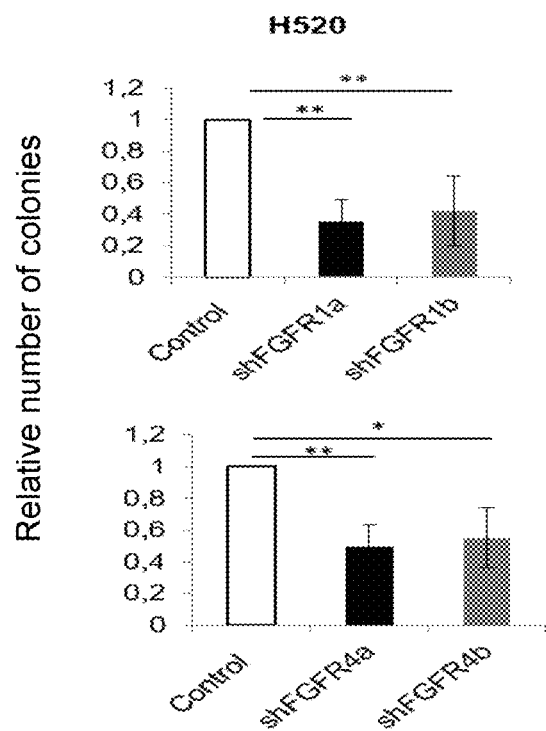
Figure 3D:
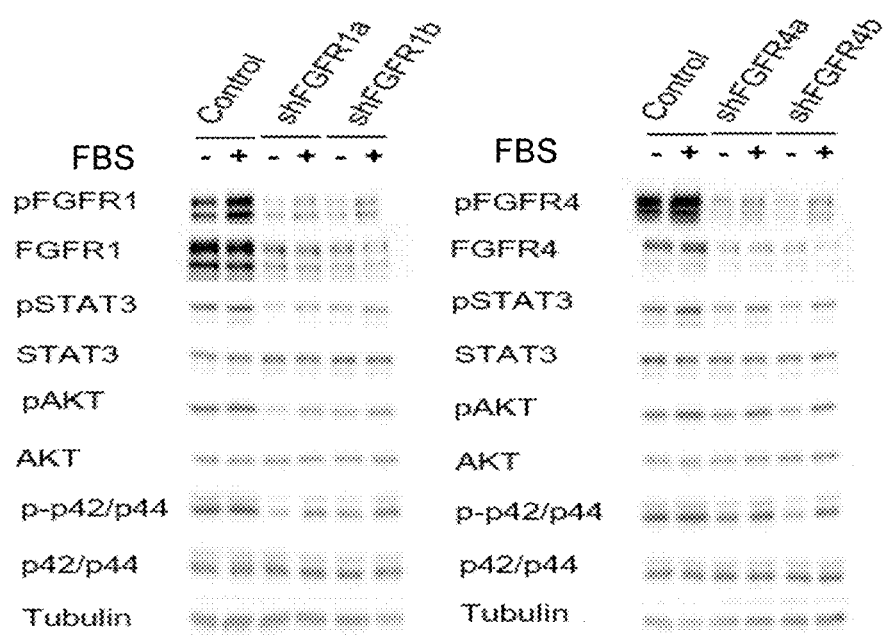

FIG. 3A shows the relative growth of the H520 line with the FGFR1 gene silenced (above) and with the FGFR4 gene silenced (below) over time, in medium with 10% FBS. It may be observed that the growth of the cell lines with one of the FGFRs silenced is less than that of the control cells. This effect is particularly apparent in the case of FGFR4 silencing. In the anchor-free growth (FIG. 3C) and clonability (FIG. 3B) assays, a lower tumourigenic capacity of the lines is observed with one of the FGFRs silenced, in comparison with the control line. With regard to the activation of the oncogenic signalling pathways under study, it was observed that the silencing of either of the two genes causes a reduction in the activation of the silenced FGFR receptor, likewise of the STAT3, AKT and p42/p44 pathways (FIG. 3D). Samples (a) and (b) of the experiments in FIG. 3 correspond to two independent shRNAs for the silencing of the same gene, in order to prevent the effect observed from being derived from the unspecific silencing of a different gene. All the tests were performed at least in triplicate. Representative growth curves are shown. For the clonability and the anchor-free growth test, the mean and standard deviation of the replica colonies are shown, after standardisation with the control condition, which takes the value of 1. For the anchor-free growth test, the mean and standard deviation of the size of the colonies is also shown. The p-values were obtained by means of Student's T-test with a confidence interval of 95%; the p-values below 0.05 are represented as *, the p-values below 0.01 as , and the p-values below 0.001 as *.

These data confirm the oncogenic role described for FGFR1 in epidermoid lung cancer and suggest a similar role for FGFR4 in this pathology; as yet, this is still to be proven.

The data presented indicate that the expression of FGFR4 and/or FGFR1 in squamous cell carcinoma cell lines gives rise to an increase in the tumourigenic characteristics of the samples, likewise the activation of the pro-oncogenic signalling pathways.

Example 2. Effect of the Expression of the FGFR1 and FGFR4 Genes on Tumourigenesis in Lung Adenocarcinoma In order to verify the effect of FGFR1 and FGFR4 on the oncogenic properties of lung adenocarcinoma cell lines, cell lines with different tumourigenic molecular disruptions were selected in order to verify whether their effect is dependent on the molecular context. To this end, cell lines with adenocarcinoma-relevant disruptions and low expression of both receptors were selected, in order to express them independently.

The procedure was the same as that described in Example 1. The H2009 (with mutation in KRAS) and H3122 (carrier of the EML4-ALK translocation) cell lines were selected and the receptors were independently overexpressed in each by transfecting the lines with the appropriate plasmid, in accordance with Table 4.

Figure 4A:
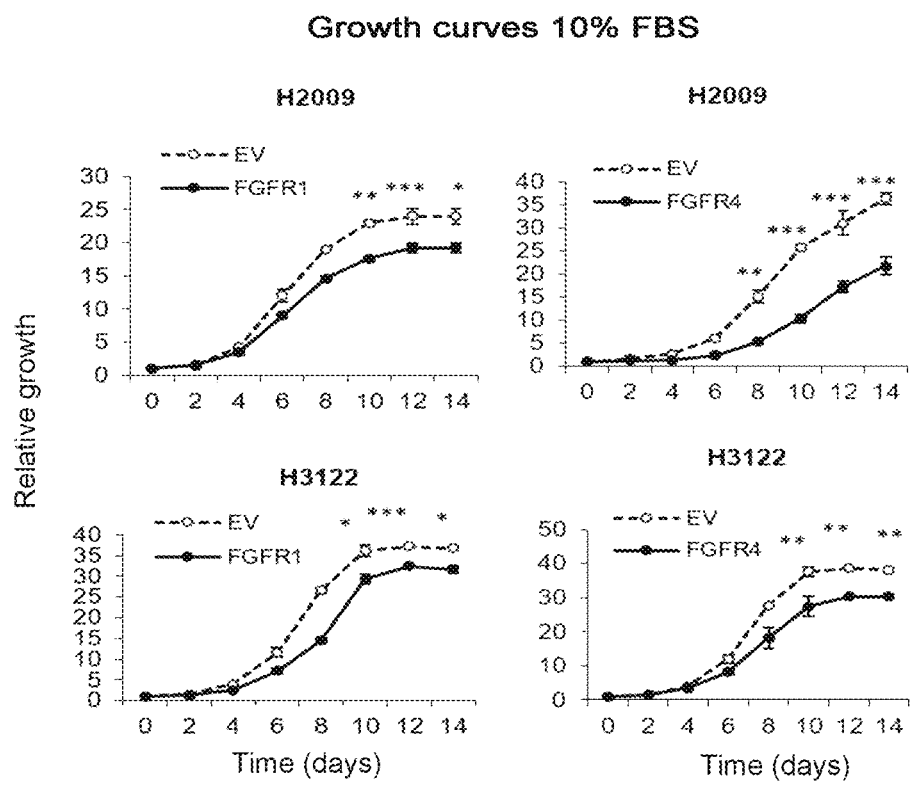
FIG. 4. Effect of FGFR1 and FGFR4 overexpression on ADC lines. Growth curves at 10% FBS (A), clonability (B) and anchor-free growth (C). Study of the activation of FGFR-related signalling pathways by western blot (D) in the presence or absence of FBS. EV=empty vector, FGFR1=overexpression of FGFR1, FGFR4=overexpression of FGFR4, FBS=foetal bovine serum. The p-values are represented by asterisks (*, p<0.05; , p<0.01; *, p<0.001).
Figure 4B:
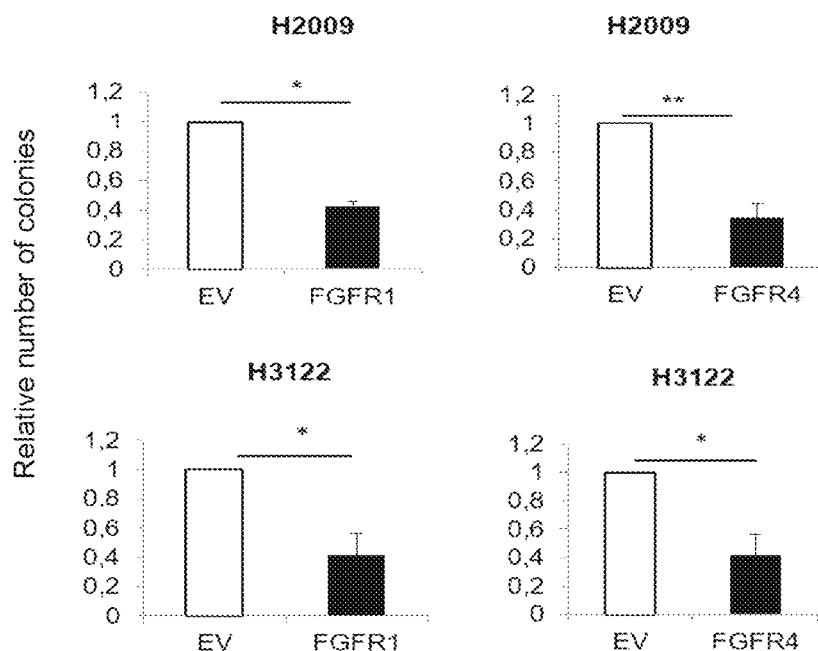

Surprisingly, and unlike what occurs in epidermoid lung cancer, the overexpression of each of the receptors caused a reduction in the tumourigenic characteristics of the two samples, as observed in the cell proliferation (FIG. 4A) and clonability (FIG. 4B) assays and the anchor-free growth assay (FIG. 4C) with regard to their respective control lines transfected with the empty vector (EV).

Next, the activation of several FGFR-related pro-oncogenic signalling pathways was measured (FIG. 4D). A lower activation of STAT3 and AKT was observed under the conditions of FGFR1 overexpression. All tests were performed in triplicate. Representative growth curves are shown. For the clonability and the anchor-free growth assay, the mean and standard deviation of the replicas are shown, after standardisation with the control condition, which takes the value of 1. For the anchor-free growth test, the mean and standard deviation of the size of the colonies is also shown. EV=empty vector, FGFR1=overexpression of FGFR1, FBS=foetal bovine serum. The p-values are represented by asterisks (*, $p<0.05$; , $p<0.01$; *, $p<0.001$).

It should be highlighted that the overexpression of FGFR1 or FGFR4 in these lines does not induce the overactivation of the overexpressed receptor, as is the case with the epidermoid lines (see FIG. 3D vs. FIG. 4D).

A549, one of the adenocarcinoma lines (with mutation in KRAS), expresses high levels of FGFR1 and FGFR4. To verify the effect of both genes on the tumourigenic characteristics of this line, both FGFRs were silenced individually by using interference RNA (shRNA). The nomenclature of shRNAs (a) and (b) correspond to two independent shRNAs for the silencing of the same gene, in order to prevent the observed effect being derived from the unspecific silencing of a different gene. All tests were performed in triplicate. Representative growth curves are shown. For the clonability and the anchor-free growth test, the mean and standard deviation of the replicas are shown, after standardising the control condition, which takes the value of 1. For the anchor-free growth assay, the mean and standard deviation of the size of the colonies is also shown. Control=unspecific shRNA, shFGFR1=FGFR1 silencing, shFGFR4=FGFR4 silencing, FBS=foetal bovine serum. The p-values are represented by asterisks (*, $p<0.05$; , $p<0.01$; *, $p<0.001$).

Figure 5A:
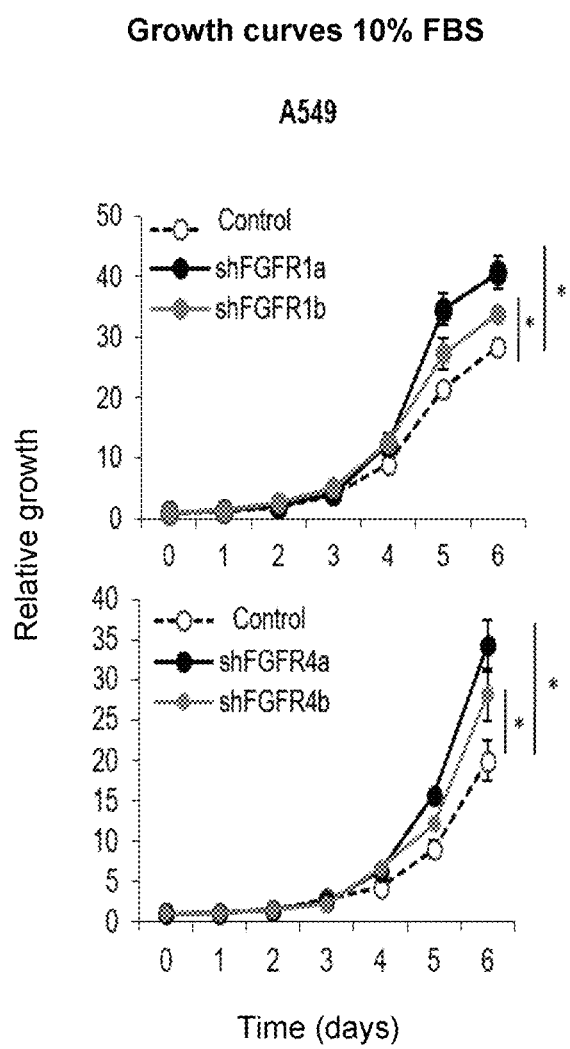
FIG. 5. Effect of FGFR1 or FGFR4 silencing on an EGFR-independent adenocarcinoma line. Growth curves at 10% FBS (A), clonability (B) and anchor-free growth (C). Measurement of the activation of FGFR-related signalling pathways (D). Control=unspecific shRNA, shFGFR1=FGFR1 silencing, shFGFR4=FGFR4 silencing, FBS=foetal bovine serum. Samples (a) and (b) correspond to two independent shRNAs to silence the same gene. The p-values are represented by asterisks (*, p<0.05; , p<0.01; *, p<0.001).
Figure 5B:
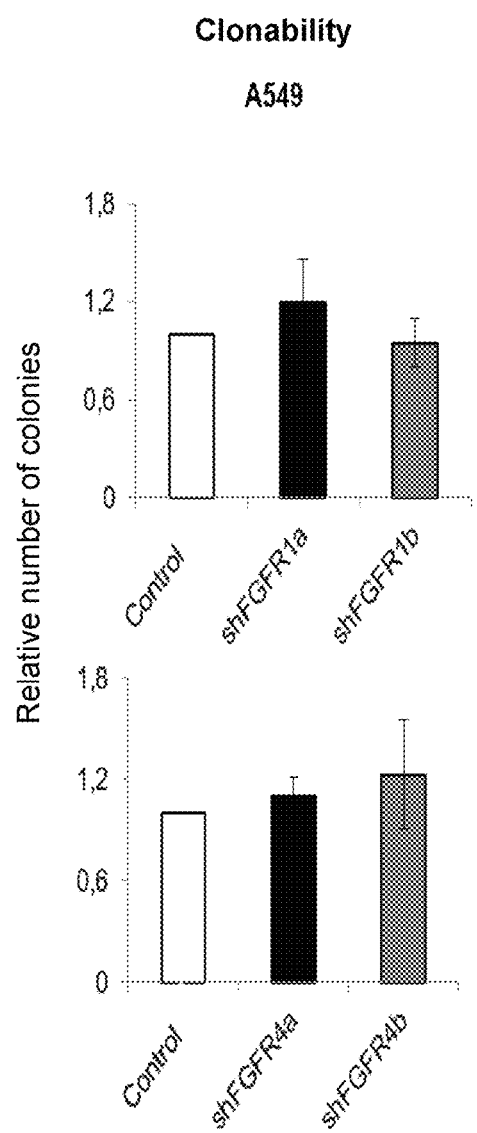
Figure 5C:
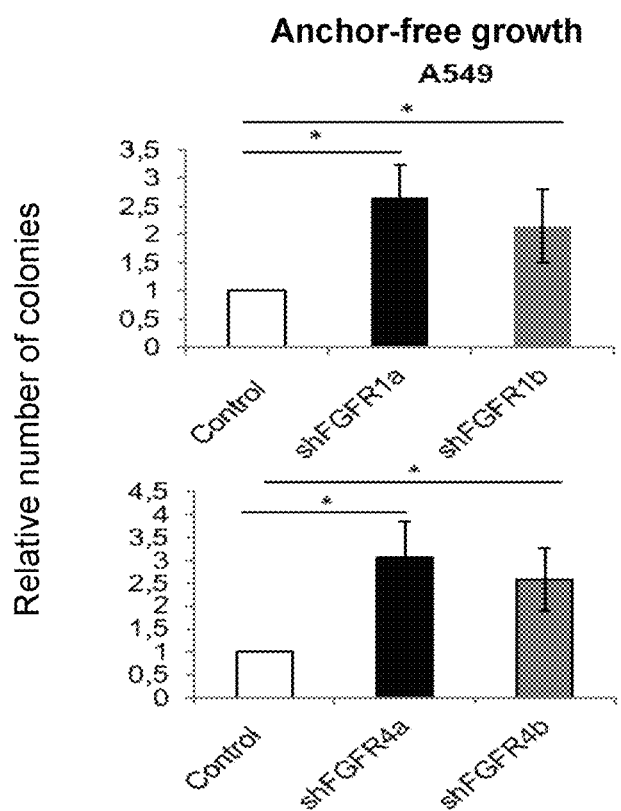
Figure 5D:
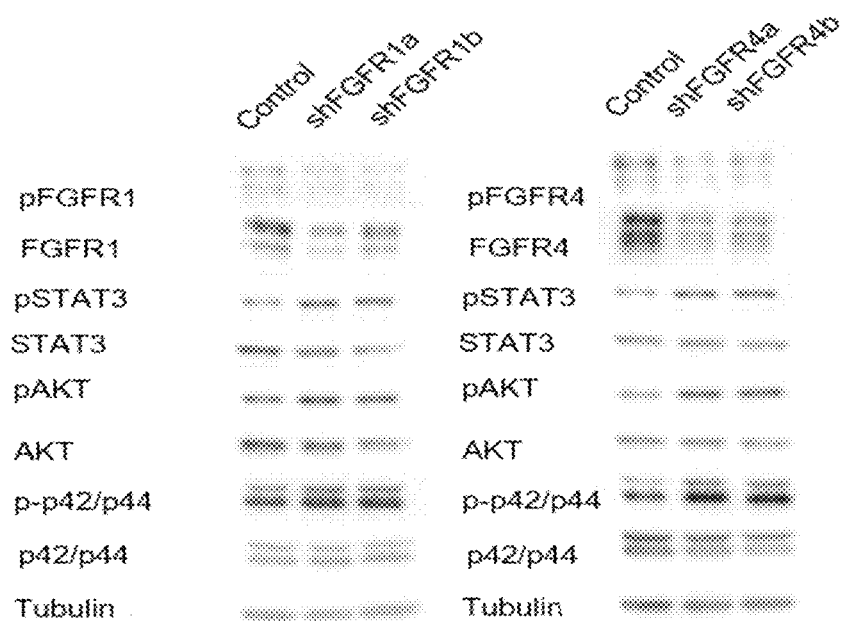

In concordance with the results obtained previously, silencing the expression of either of the two genes causes an increase in cell proliferation (FIG. 5A), an increase in the generation of colonies in the anchor-free growth assay and in the size of these colonies with regard to the control line (FIG. 5C). However, in the clonability assays no differences were observed in the number of colonies generated in either case (FIG. 5B). When the activation of STA3 and AKT was measured, greater activation of these pathways was observed under conditions of FGFR1 or FGFR4 silencing with regard to the control line, and the same occurs with p42/p44, although with a less marked increase in its activation (FIG. 3D).

All these results together suggest a tumour suppressor role of both FGFRs in lung adenocarcinoma and an oncogenic role in squamous cell carcinoma.

Example 3. Identification of N-Cadherin as Responsible for the Different Behaviour of FGFR1 and FGFR4 in Lung Adenocarcinoma and Squamous Cell Carcinoma In order to find an explanation for the differential effect of FGFR1 and FGFR4 on the non-small-cell lung cancer tumourigenesis identified in Examples 1 and 2, a search was undertaken for candidate genes which might be responsible for this behaviour.

To this end, it was verified whether the mesenchymal or epithelial characteristics of the cell lines could determine the role of the different FGFRs in lung cancer. To this end, an analysis was performed of the expression of N-cadherin (mesenchymal marker) and E-cadherin (epithelial marker) (Gheldof 2013) in the collection of lung cancer cell lines described in FIG. 1.

Figure 6:
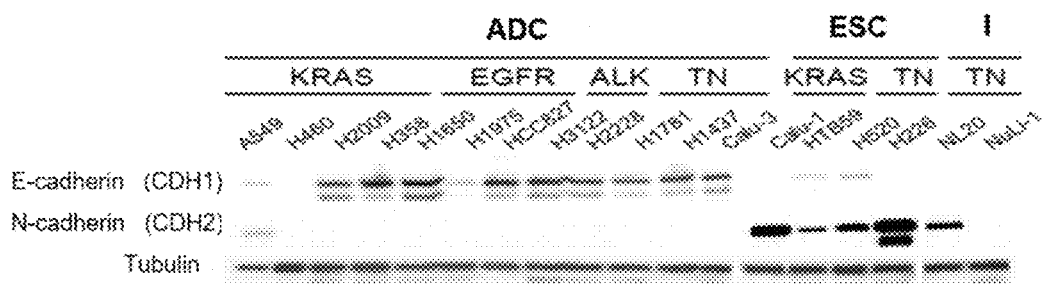
FIG. 6. Characterisation of E-cadherin and N-cadherin expression in lung cancer cell lines. ADC=Adenocarcinoma, SCC=Epidermoid, I=Immortalised, KRAS=Mutated KRAS, EGFR=Mutated EGFR, ALK=Carrier of ALK translocation, TN=Triple negative (absence of disruptions in KRAS, EGFR or ALK).

FIG. 6 shows how both proteins are expressed differentially in the two histological types analysed (adenocarcinoma (ADC) and squamous cell or epidermoid carcinoma (SCC)). E-cadherin is expressed in almost the entirety of the adenocarcinoma lines, but in none of the epidermoid carcinoma lines, while N-cadherin displays the opposite result.

To verify whether N-cadherin is responsible for the pro-tumourigenic effects of FGFR1 and FGFR4, N-cadherin was overexpressed in two adenocarcinoma lines (H2009 and H3122), transfecting them with the N-cadherin overexpression plasmid (Table 4) in combination or not with FGFR1 or FGFR4 overexpression plasmids.

Figure 7A:
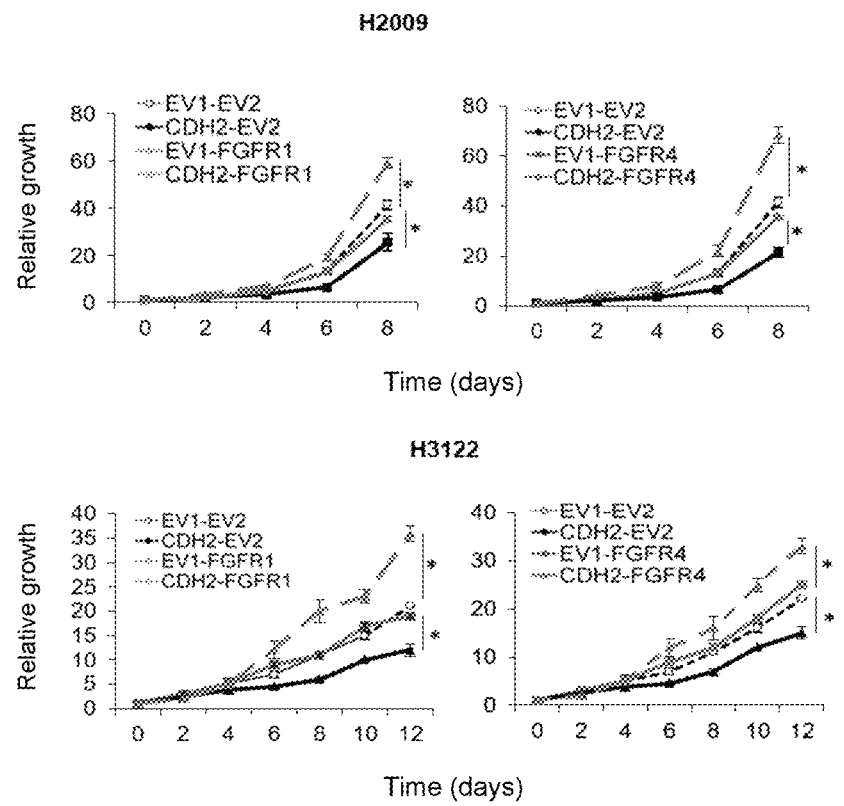
FIG. 7. Effect of the co-overexpression of N-cadherin with FGFR1 or FGFR4 in adenocarcinoma lines. Growth curves at 10% FBS (A), clonability (B) and anchor-free growth (C). Analysis of the activation of FGFR-related signalling pathways (D). EV1=empty vector 1, EV2=empty vector 2, CDH2=Overexpression of N-cadherin, FGFR1=Overexpression of FGFR1, FGFR4=Overexpression of FGFR4, FBS=Foetal bovine serum. The p-values are represented by asterisks (*, p<0.05; , p<0.01; *, p<0.001).
Figure 7B:
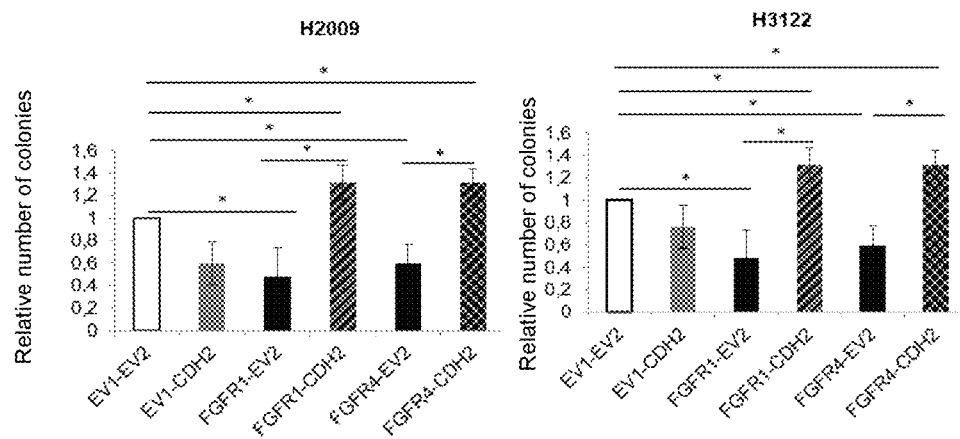
Figure 7C:
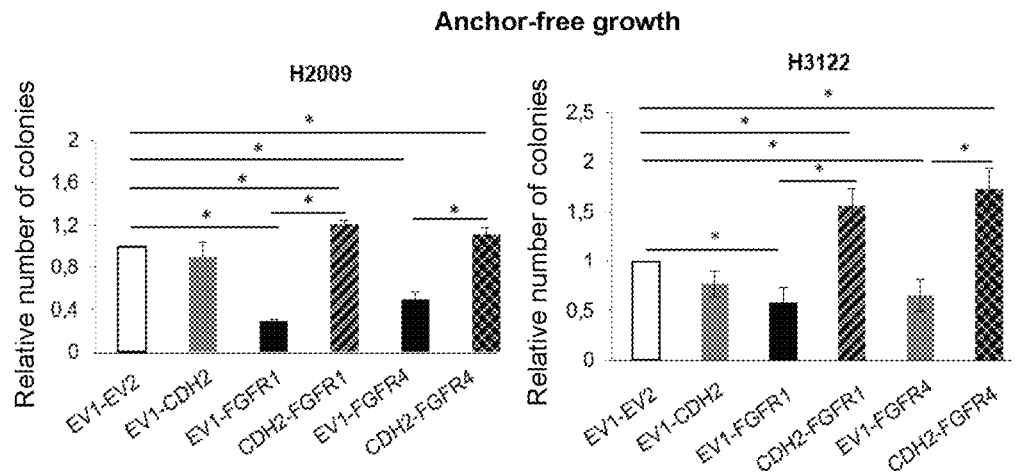
Figure 7D:
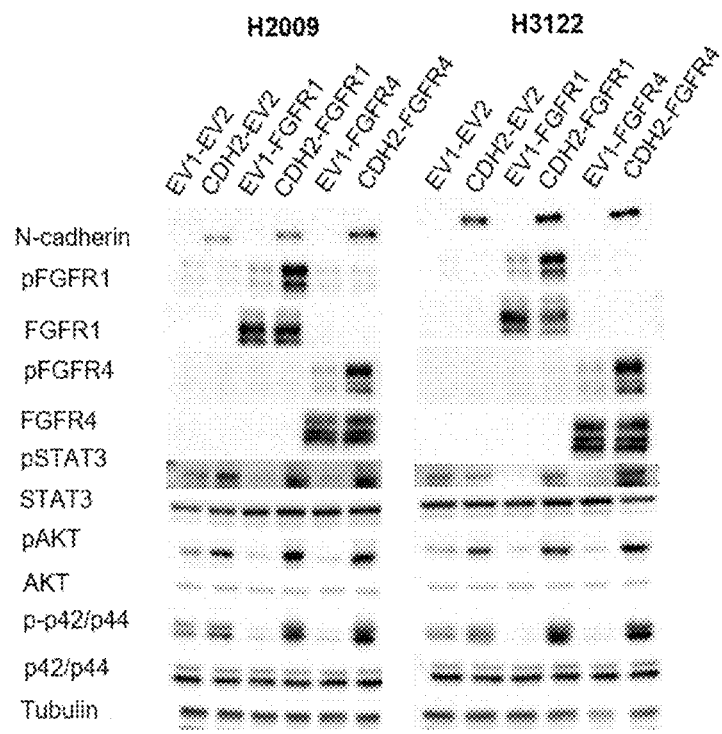

As revealed in Example 2, overexpression of these FGFRs has a tumour-suppressive effect. However, when N-cadherin and each of the receptors (CDH2-FGFR1 or CDH2-FGFR4) are overexpressed, both FGFRs not only cease to exert a tumour-suppressive effect but exert a pro-oncogenic effect, increasing the oncogenic characteristics of both lines, above the control lines and the cells expressing solely N-cadherin, as may be observed in FIGS. 7A-7C (Growth curves at 10% FBS (7A), clonability (7B) and anchor-free growth (7C)). All the tests were performed in triplicate. Representative growth curves are shown. For the clonability and the anchor-free growth test, the mean and standard deviation of the replicas are shown, after standardising the control condition, which takes the value of 1. For the anchor-free growth test, the mean and standard deviation of the size of the colonies is also shown. EV1=empty vector 1, EV2=empty vector 2, CDH2=Overexpression of N-cadherin, FGFR1=Overexpression of FGFR1, FGFR4=Overexpression of FGFR4, FBS=Foetal bovine serum. The p-values are represented by asterisks (*, $p<0.05$; , $p<0.01$; *, $p<0.001$). Furthermore, on studying the activation of the pro-oncogenic signalling pathways in these lines, a reduction in the activation of the pro-oncogenic signalling pathways with regard to the control is observed when either of the FGFRs is overexpressed in the absence of N-cadherin, and the opposite effect is observed when the FGFRs are co-overexpressed with N-cadherin (FIG. 7D).

From this experiment it may be deduced that the expression of N-cadherin is responsible for the oncogenic effect of FGFR1 and FGFR4, which would explain the differences in the behaviour of both genes between adenocarcinoma and epidermoid carcinoma.

Figure 8A:
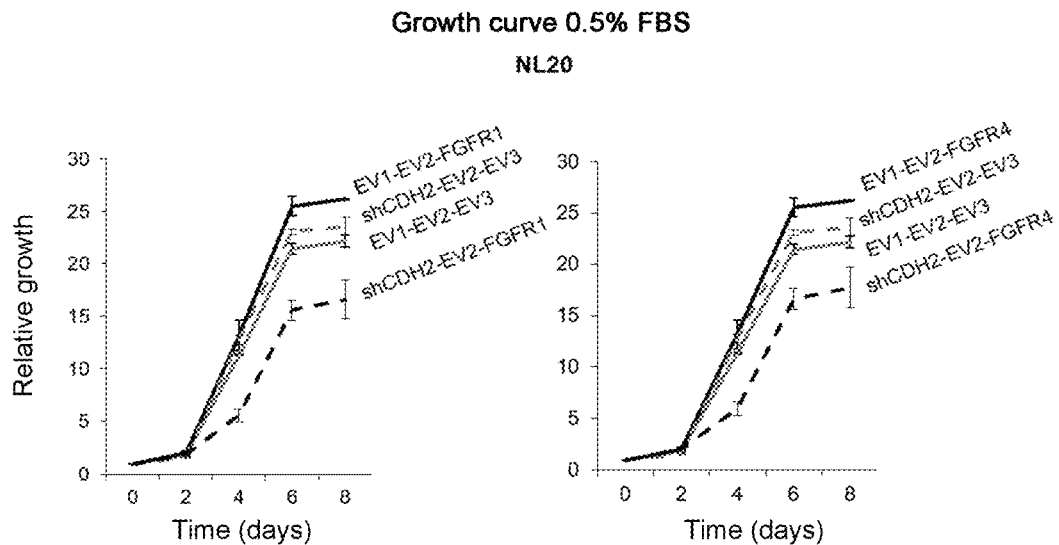
FIG. 8. Effect of N-cadherin silencing in a cell line overexpressing FGFR1 or FGFR4. Growth curves at 5% FBS (A), anchor-free growth assays (B), and determination of the activation of oncogenic signalling (C). (D) Tumoural growth of xenografts from the panel of stable lines generated from the immortalised NL20 lung cell line with different combinations of expression of N-cadherin, FGFR1 or FGFR4. The p-values were obtained by means of Student's T-test with a confidence interval of 95%, and are represented by asterisks (*, p<0.05; , p<0.01; *, p<0.001). EV1=Control empty vector 1, EV2=Control empty vector 2. FGFR1=Overexpression of FGFR1, FGFR4=Overexpression of FGFR4, shCDH2=N-cadherin silencing.
Figure 8B:
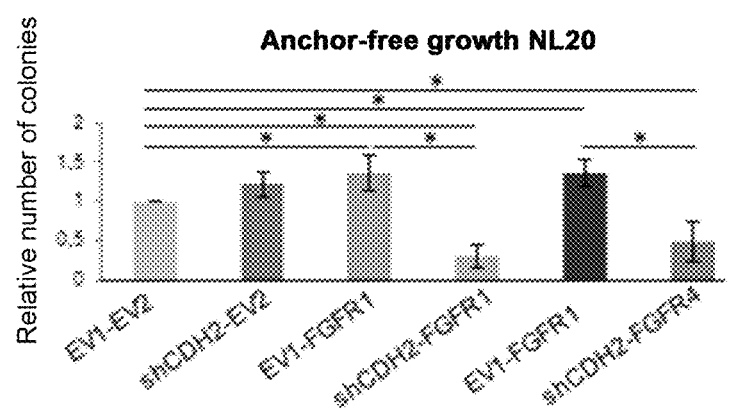
Figure 8C:
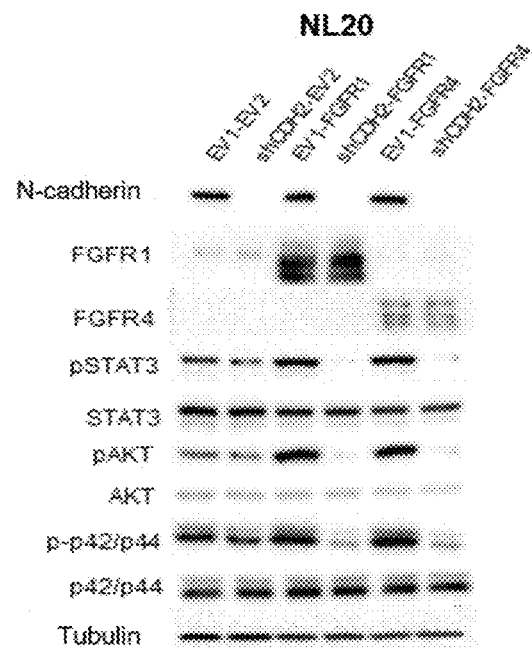

Next, the opposite experiment was performed in an immortalised lung cell line with high endogenous expression of N-cadherin (NL20), but without endogenous expression of FGFR1 or FGFR4 (FIG. 1). In this experiment, N-cadherin was silenced, as described above, and was combined with the overexpression of each FGFR (shCDH2-FGFR1 or shCDH2-FGFR4). FIGS. 8A and 8B show the result of the tumourigenicity assays on the growth curves and the assay in soft agar, respectively. The results indicate that the expression of FGFR1 or FGFR4 has a tumour-suppressive effect in the absence of, or in the presence of low levels of, N-cadherin (shCDH2-EV1-FGFR1 and shCDH2-EV1-FGFR4), and a pro-tumourigenic effect in the presence of a high expression of N-cadherin (EV1-EV2-FGFR1 and EV1-EV2-FGFR4).

FIG. 8 shows the study of the activation of the oncogenic signalling pathways. The obtained results were concordant, revealing an increase in tumourigenicity and in the activation of the pathways under study when either of the FGFRs is overexpressed in the presence of endogenous N-cadherin, and the opposite effect when the FGFRs are overexpressed in the presence of low levels of N-cadherin.

From this experiment it may be deduced that the expression of N-cadherin is responsible for the tumourigenic effect of FGFR1 and FGFR4 in non-small-cell lung cancer (NSSLC).

Furthermore, to verify the effects observed, they were reproduced in vivo; xenografts of the aforementioned cell lines were performed in immunocompromised nude mice and the growth of the tumours generated from the xenografts was determined.

Figure 8D:
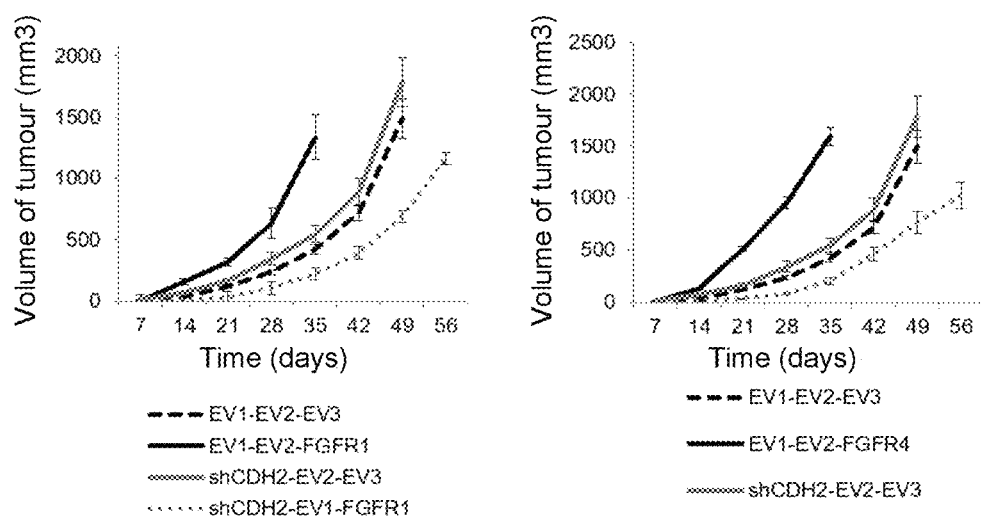

FIG. 8D shows that the growth of the tumours generated by the different lines correlates with the results obtained in vitro, observing that the tumours co-expressing N-cadherin and FGFR1 or FGFR4 have a significantly greater growth than those expressing N-cadherin alone, or which do not express any of these genes, while the tumours expressing FGFR1 or FGFR4 alone display a slower tumour growth, as proven in the examples above.

All these data confirm that it is the co-expression of N-cadherin with either FGFR1 or FGFR4 which is responsible for the tumourigenic effect of these FGFRs in non-small-cell lung cancer.

Finally, to study whether the tumourigenic effect of the combination of N-cadherin and FGFR1 or FGFR4 may be due to a physical interaction between the proteins, co-immunofluorescence experiments were performed to verify whether the proteins co-localise on the cell membrane.

Figure 9A:
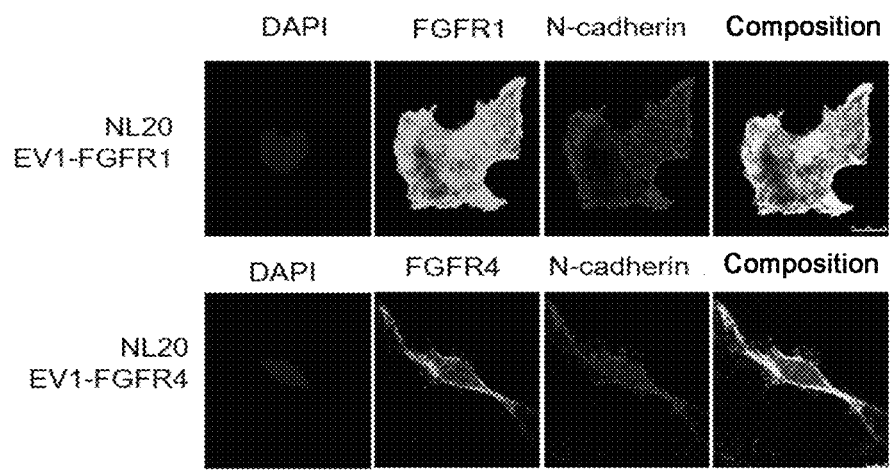
FIG. 9. Interaction of N-cadherin with FGFR1 or FGFR4. (A) Co-immunolocalisation assay of N-cadherin and FGFR1 or FGFR4 in the NL20 cell line with exogenous overexpression of the receptors. (B) Co-immunoprecipitation of N-cadherin with FGFR1 and FGFR4 in the H520 cell line.

For this purpose the NL20 cell line was used; this has high endogenous expression of N-cadherin with exogenous overexpression of FGFR1 or FGFR4. FIG. 9A shows that there is partial co-localisation of N-cadherin with FGFR1 and FGFR4 in some regions of the cell membrane. These results suggest that the interaction between the proteins may be physical. To test this hypothesis, co-immunoprecipitation experiments were performed. A cell line with high endogenous expression of the three proteins (H520) was selected. The immunoprecipitation of N-cadherin was performed, and the presence of FGFR1 or FGFR4 in the immunoprecipitate was determined, as described in the materials and methods herein.

Figure 9B:
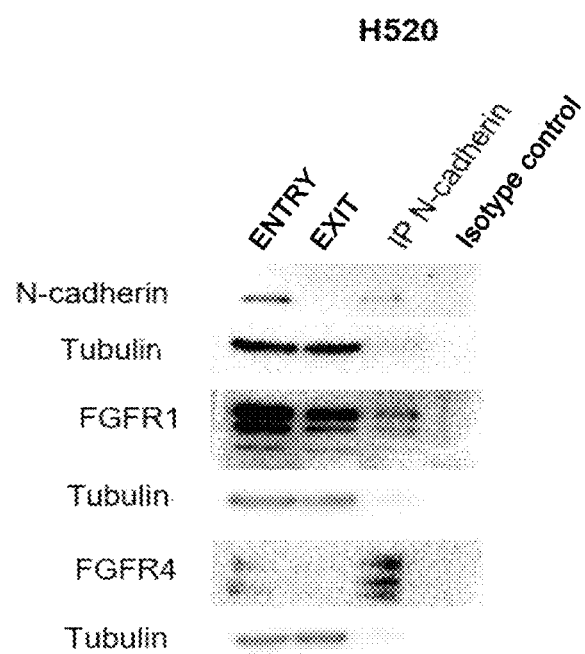

FIG. 9B shows that both FGFR1 and FGFR4 co-immunoprecipitate with N-cadherin, supporting the existence of a physical interaction between both types of receptors.

Example 4. Function of N-Cadherin in the Prognostic Role of FGFR1 and FGFR4 in Patients with Non-Small-Cell Lung Cancer To verify the importance of N-cadherin in the prognostic role of FGFR1 and FGFR4 in patients with non-small-cell lung cancer and to verify the above results, two study cohorts were employed: one discovery cohort and one validation cohort.

A discovery cohort of 109 patients diagnosed with early-stage (I-III) non-small-cell lung cancer (NSCLC) treated with radical surgery at the "Virgen del Rocío" University Hospital (Seville) was employed (NSCLC$_{N=109}$). Table 7 shows the characteristics of the cohort. The research project was evaluated and approved by the hospital ethics committee (2012PI/241). The patients signed the mandatory informed consent of the hospital biobank. The entire project followed the universal ethical principles contained in the declaration of Helsinki.

The samples of tumour tissue, set in paraffin, of all the cases were analysed subsequent to the performance of the anatomopathological diagnosis. The mRNA was extracted from these samples as described above, although it is also possible to detect and quantify the expression of the genes of interest by means of direct immunohistochemistry in the biopsies. The overall survival (OS) and progression-free survival (PFS) were analysed; that is, the time elapsing during and subsequent to the treatment during which the cancer neither grows nor spreads further, against time (months). The p-values were calculated by means of Log Rank analysis.

Figure 10A:
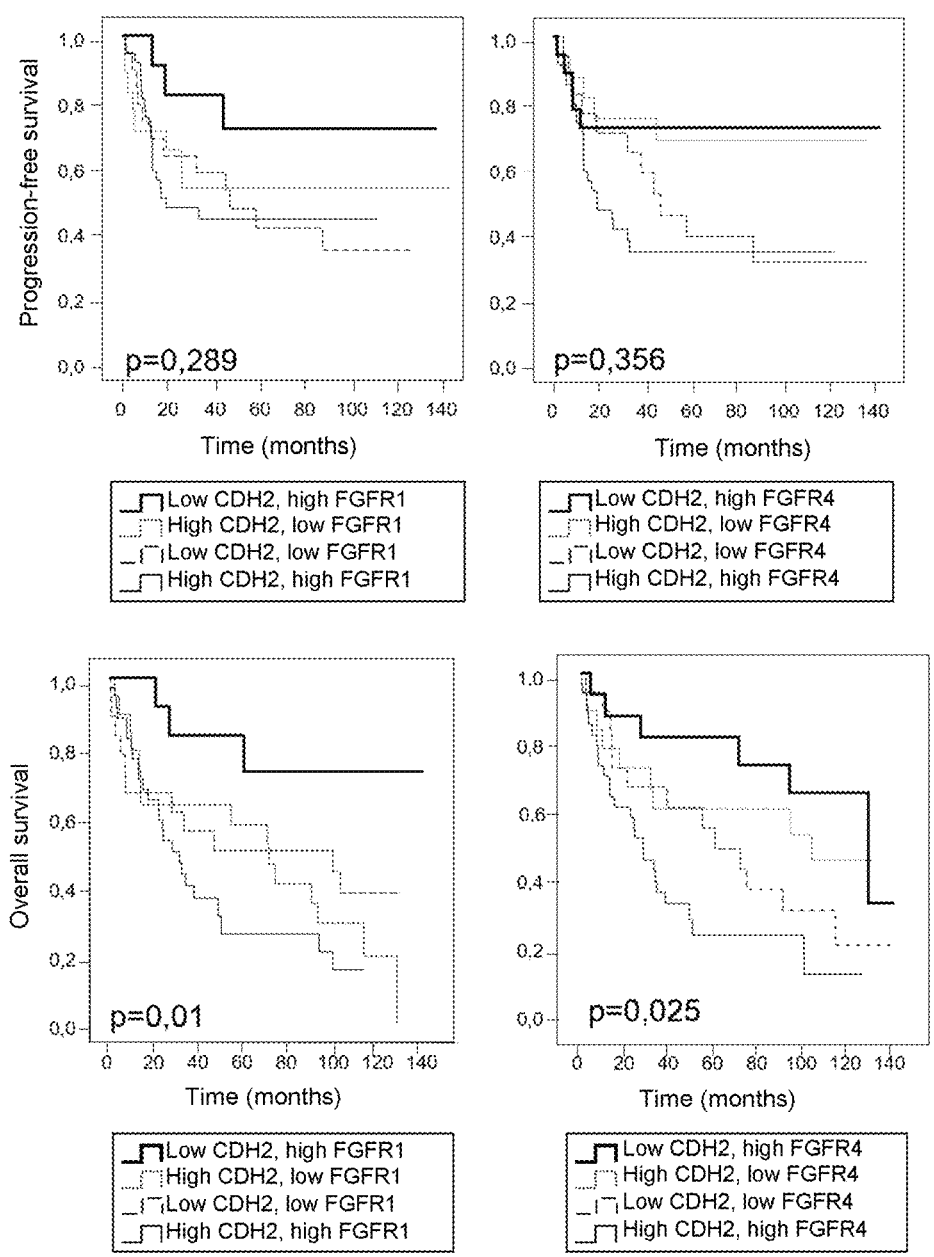
FIG. 10. Association of the mRNA expression of N-cadherin and of FGFR1 or FGFR4 with survival in patients with non-small-cell lung cancer (N=109). The criterion for discerning between low and high expression is the value of the median expression for each gene measured in $2^{-\Delta CT}$. (A) Progression-free survival and overall survival of the patient cohort with regard to their gene expression. (B) Association of N-cadherin mRNA expression with progression-free survival and overall survival in the subgroup of NSCLC patients with high FGFR1 or FGFR4 expression (N=89). NSCLC=Non-small cell lung cancer.

FIG. 10A shows the Kaplan-Meier curves of survival in accordance with the gene expression of the study cohort. It was observed that the group with high expression of N-cadherin and FGFR1 yielded the worst progression-free survival (PFS) and overall survival (OS) data, while the group with high expression of FGFR1 and low expression of N-cadherin yielded the best data for both types of survival. It is noteworthy that of the group with low expression of N-cadherin and high expression of FGFR1, over 70% of the patients are still alive, unlike the 30-40% of the other groups. Analogously, the samples with low N-cadherin and high expression of FGFR4 have better survival (both PFS and OS) than the samples with high expression of both genes.

TABLE 7

Characteristics of our non-small-cell lung cancer cohort.

| | |
|---|---|
| Number of patients | 109 |
| Gender | |
| Male | 100 (92%) |
| Female | 9 (8%) |
| Mean age (years) | 65.0 (54.0-78.0) |
| Tobacco use | |
| Smoker | 56 (51.3%) |
| Ex-smoker | 48 (44.1%) |

TABLE 7-continued

Characteristics of our non-small-cell lung cancer cohort.

| | | |
|---|---|---|
| Number of patients | 109 | |
| Non-smoker | 5 | (4.6%) |
| Epidermoid carcinoma | 58 | (53.2%) |
| Stage I-II | 43 | (74.1%) |
| Stage III | 15 | (25.9%) |
| Adenocarcinoma | 36 | (33%) |
| Stage I-II | 30 | (83.3%) |
| Stage III | 6 | (16.6%) |
| Other histologies | 15 | (13.7%) |

Figure 10B:
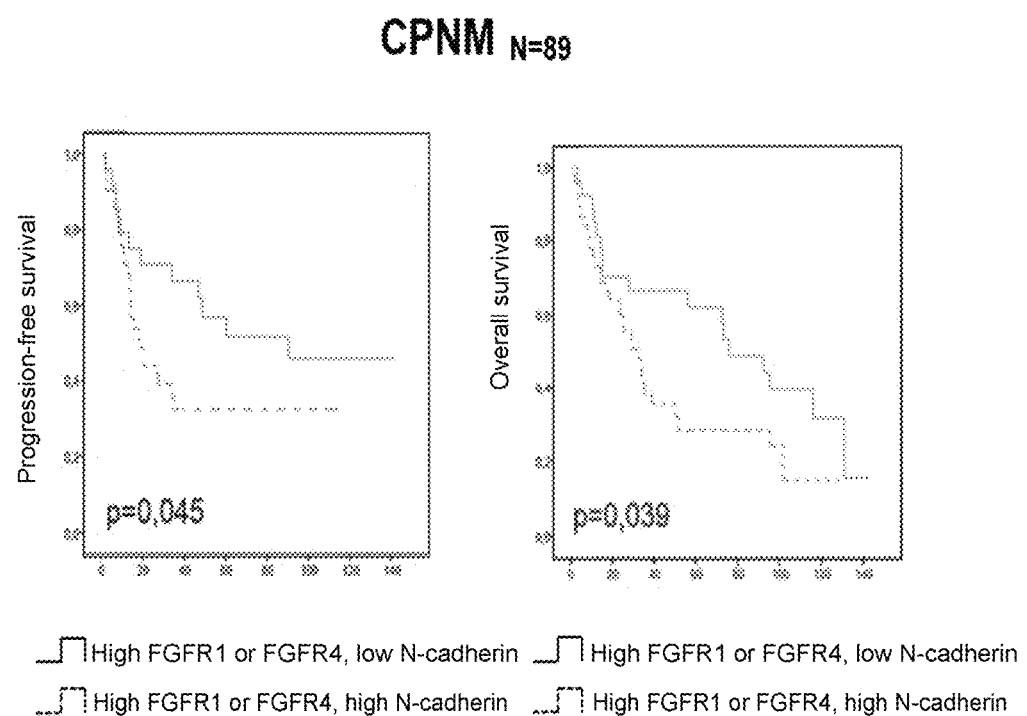

FIG. 10B shows the survival curves of patients with high expression of FGFR1 and/or FGFR4 with regard to their expression of N-cadherin. As expected, the patients with high expression of one or both of the FGFRs and low expression of N-cadherin displayed better progression-free and overall survival than the subgroup with high expression of both genes (hazard ratio 2.06 [1.01-4.23], p=0.045 and hazard ratio 1.89 [1.02-3.49] p=0.039, respectively). These survival curves clearly show the potential of N-cadherin as a modulator of the role of FGFR1 and FGFR4 in lung cancer oncogenesis.

To validate the prognostic role of N-cadherin and FGFR1 or FGFR4, the same analyses were performed in two clinical databases publicly available at The Cancer Genome Atlas (TCGA), one of adenocarcinoma patients (N=522) and the other of epidermoid carcinoma patients (N=504) (Table 8) (http://cancergenome.nih.gov/).

TABLE 8

Characteristics of the TCGA adenocarcinoma and epidermoid carcinoma cohorts.

| | Histology | |
|---|---|---|
| | Adenocarcinoma | Epidermoid carcinoma |
| Number of patients | 522 | 504 |
| Gender | | |
| Male | 219 (37.9%) | 314 (42.4%) |
| Female | 253 (43.8%) | 108 (21.2%) |
| Unknown | 106 (18.3%) | 83 (16.4%) |
| Mean age (years) | 66.9 (59.6-73.4) | 68.6 (62.3-73.8) |
| Tobacco use | | |
| Smoker | 111 (19.2%) | 113 (22.2%) |
| Ex-smoker | 276 (47.8%) | 284 (56.3%) |
| Non-smoker | 71 (12.3%) | 17 (3.4%) |
| Unknown | 120 (20.7%) | 91 (18.1%) |
| Stage | | |
| I | 252 (43.6%) | 212 (41.4%) |
| II | 115 (24.4%) | 124 (24.3%) |
| III | 79 (13.7%) | 77 (15.2%) |
| IV | 25 (4.3%) | 6 (1.2%) |
| Unknown | 107 (18.5%) | 86 (17.1%) |

The categorical variables are represented as number of patients (percentage of the total) and the quantitative variables as a mean [interquartile range].

In these cohorts, the patients were divided with regard to the expression of FGFR1 and N-cadherin mRNA or FGFR4 and N-cadherin mRNA and their survival was analysed. The cut-off point between high and low expression in the case of the adenocarcinoma patient cohort was defined as the median in the case of FGFR1 and FGFR4, and as the first quartile in the case of FGFR4. In the case of the epidermoid carcinoma cohort, the cut-off point was the median of expression for each of the genes.

Figure 11A:
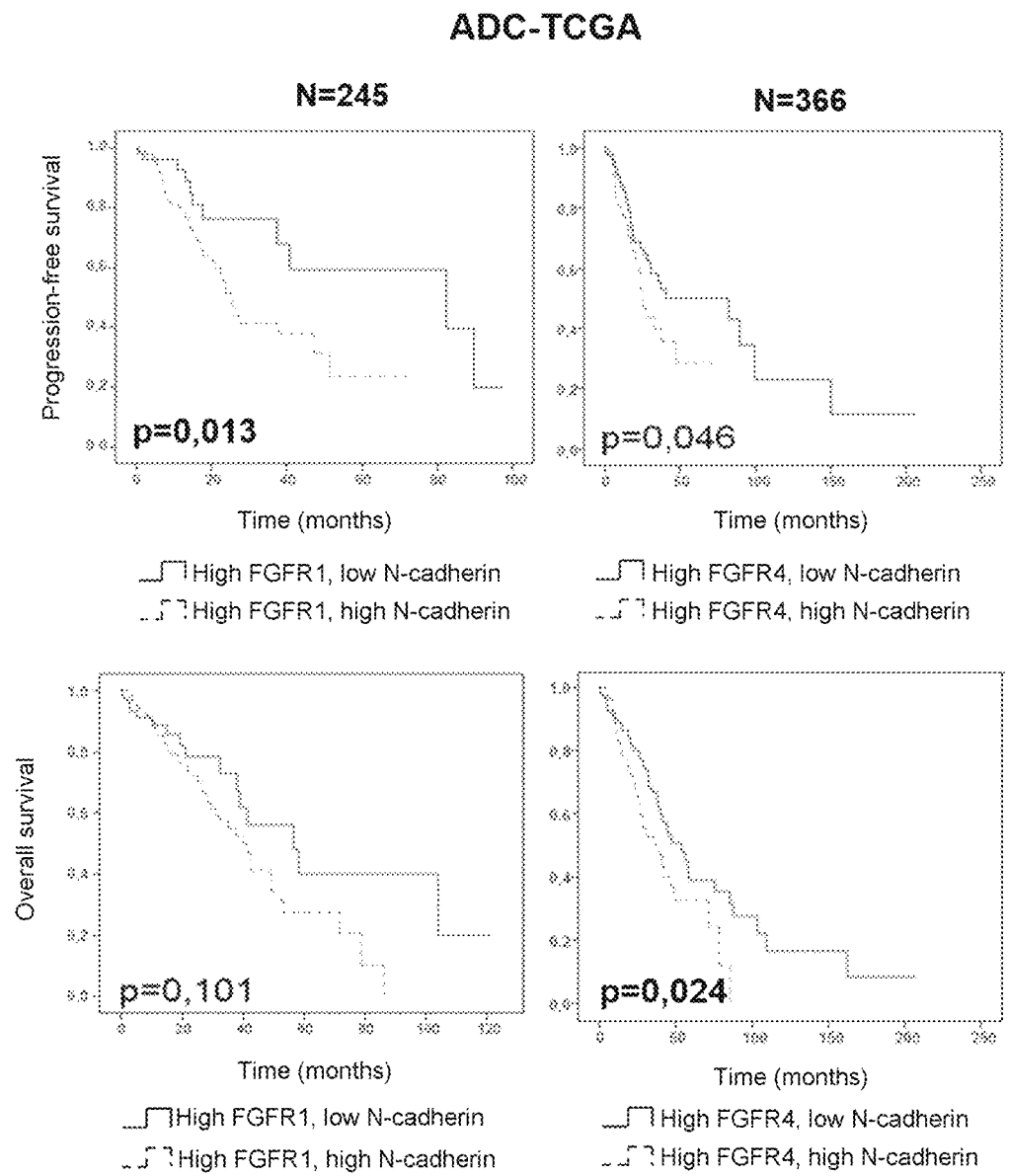
FIG. 11. Association of the mRNA expression of N-cadherin and of FGFR1 and/or FGFR4 with survival in patients with adenocarcinoma. (A) Progression-free survival and overall survival of a cohort of adenocarcinoma patients with regard to their gene expression. On the left, the survival curves of the patients with high FGFR1 and high or low N-cadherin are shown (N=245), and on the right, the survival curves of the patients with high FGFR4 and high or low N-cadherin are shown (N=366) (B) Association of the mRNA expression of N-cadherin with survival in the subset of ADC-TCGA patients with high expression of FGFR1 or FGFR4, or of both. ADC-TCGA=Adenocarcinoma cohort of The Cancer Genome Atlas.

FIG. 11A shows the results of the adenocarcinoma reference cohort. It may be observed, as in the previous results, that patients with high expression of FGFR1 and low expression of N-cadherin have a better survival prognosis compared with the samples with high expression of N-cadherin and high expression of FGFR1 (hazard ratio of 2.38 [1.15-4.94], p=0.016 for progression-free survival and of 1.63 [0.90-2.95], p=0.101 for overall survival). With regard to FGFR4, similar results were obtained, with a hazard ratio of 1.61 [1.01-2.59], p=0.046 for progression-free survival and of 1.79 [1.06-2.51], p=0.024 for overall survival.

Figure 11B:
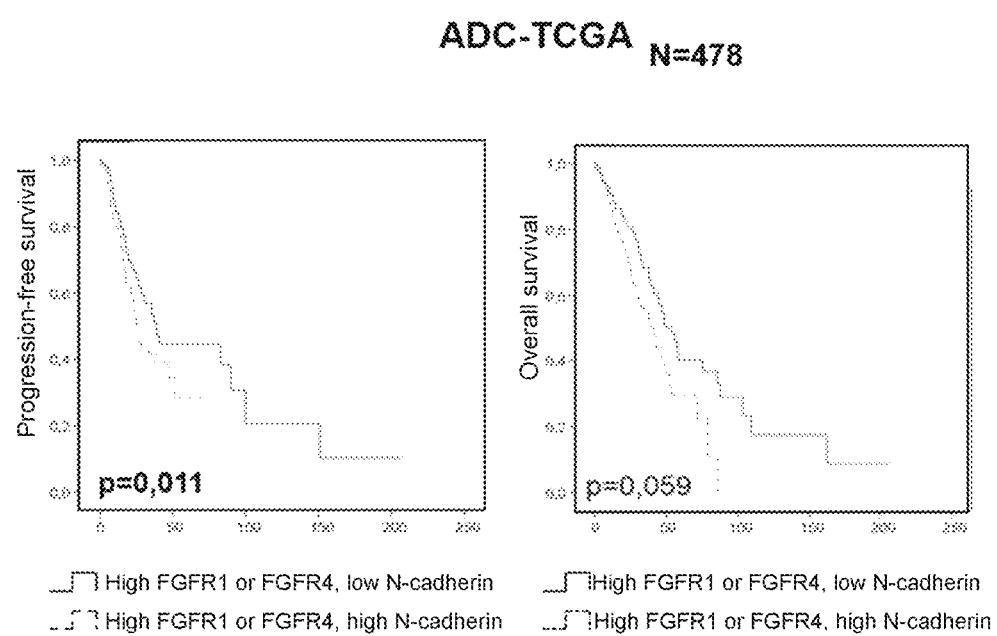

In addition, the patients with high expression of one or both FGFRs in the cohort were selected, and this subgroup of patients was divided according to the level of expression of N-cadherin. FIG. 11B shows a clear trend where, in this patient subgroup, the high levels of expression of N-cadherin are associated with worse survival (hazard ratio of 1.46 [0.98-2.17], p=0.059 for progression-free survival, and of 1.63 [1.11-2.38], p=0.011 for overall survival, thus reproducing the results obtained in the discovery cohort.

Figure 12A:
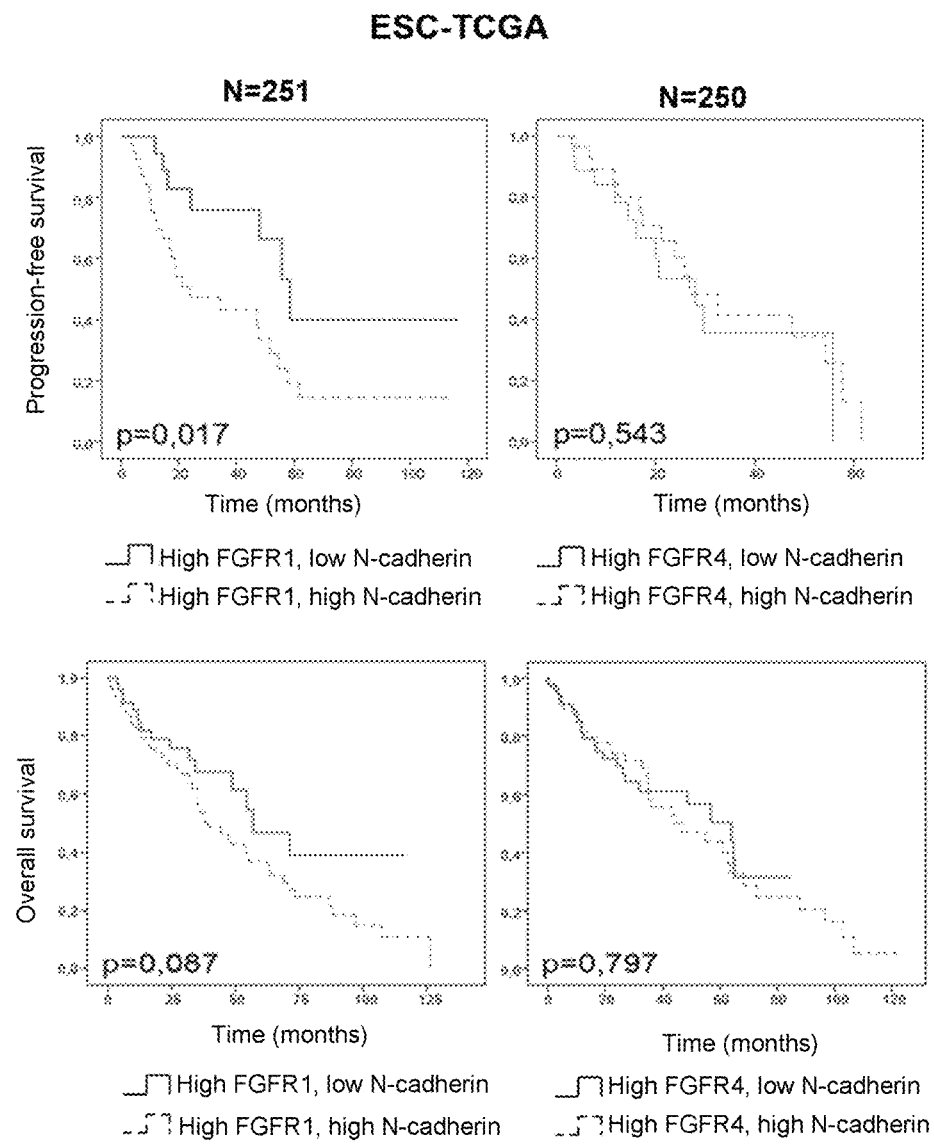
FIG. 12. Association of the mRNA expression of FGFR1, FGFR4 and N-cadherin with survival in a cohort of patients with TCGA epidermoid carcinoma (N=504). (A) Progression-free survival and overall survival of the patient cohort with regard to their gene expression. On the left, the survival curves of the patients with high FGFR1 and high or low N-cadherin are shown (N=251), and on the right, the survival curves of the patients with high FGFR4 and high or low N-cadherin are shown (N=250) (B) Association of the mRNA expression of N-cadherin with survival in the subset of SCC-TCGA patients with high expression of FGFR1, FGFR4, or of both (N=373). SCC-TCGA=Epidermoid carcinoma cohort of The Cancer Genome Atlas.
Figure 12B:
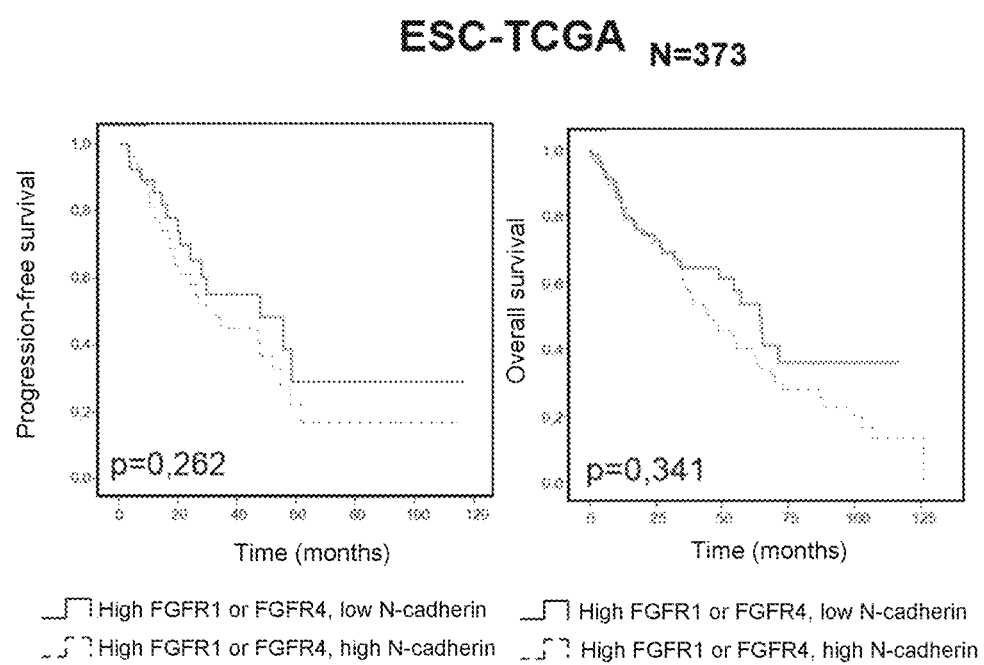

In the epidermoid carcinoma cohort the data were very similar for FGFR1, observing that among those patients with high expression of FGFR1, those with high expression of N-cadherin present a worse prognosis (hazard ratio of 1.88 [1.25-2.79], p=0.017 for progression-free survival, and of 1.34 [0.89-1.99], p=0.087 for overall survival). However, in the case of FGFR4 no differences were apparent with regard to prognosis in this cohort (FIG. 12A), nor when both receptors were taken into account (FIG. 12B). These data support the role of N-cadherin as a modulator of the anti- or pro-oncogenic role of FGFR1 and FGFR4.

From these results it may be concluded that the expression of FGFR1, FGFR4 and N-cadherin is related to prognosis in lung cancer. This, on the one hand, proves the role of N-cadherin as responsible for the pro-oncogenic effect of FGFR1 and FGFR4, and also proves the validity of the use of these genes as biomarkers in the prognosis of the disease.

Example 5. Relationship Between the Expression of N-Cadherin, FGFR1 and FGFR4 and the use of FGFR Inhibitors in Lung Cancer Treatment The above results demonstrate the role of N-cadherin as responsible for the pro-oncogenic effect of FGFR1 and FGFR4. FGFR-inhibiting agents are currently being used in clinical trials as therapeutic treatment for lung cancer. However, it is known that this type of treatment, in clinical trials, is not effective in all patients, causing side-effects in patients without alleviating the disease, and delays in the administration of a better treatment. To date, the reason for the lack of efficacy of this type of drug is unknown.

Starting with the results disclosed in the above examples, it was decided to verify whether the differences in expression of N-cadherin and FGFR1 and/or FGFR4 and their relationship with the pro-tumourigenic effects in lung cancer cell lines are also related to the activity of the selective FGFR inhibitors described for the treatment of lung cancer.

a) N-Cadherin as a Predictive Factor in in-Vitro Anti-FGFR Therapy

To verify whether N-cadherin expression is decisive in the determination of the efficacy of FGFR inhibition in lung cancer treatment, the efficacy of two selective FGFR inhibitors, in terms of growth inhibition, was tested. For this purpose, cell lines with high endogenous expression of FGFR1 and/or FGFR4 and low expression of N-cadherin (A549 and H460), or with high endogenous expression of FGFR1 and/or FGFR4 and high expression of N-cadherin (H520 and H226) were selected. In these lines, an analysis was performed on the effect on cell proliferation of two selective FGFR inhibitors: BGJ398 and AZD4547 (SELL-ECKCHEM, Refs. S2183 and S2801 respectively) with regard to time.

Figure 13A:
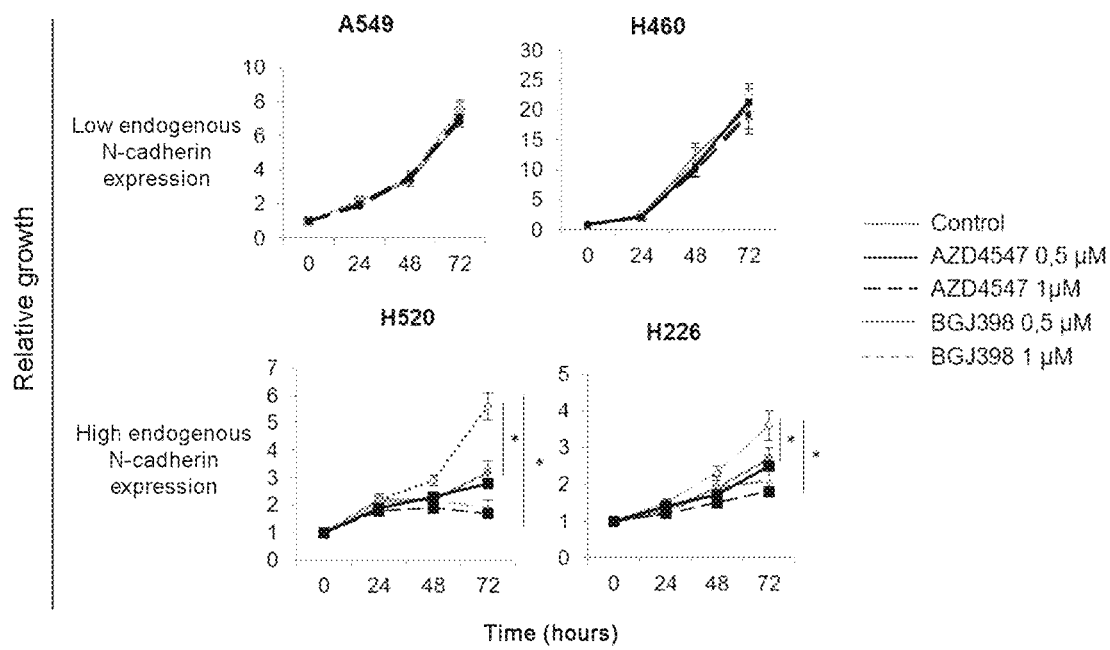
FIG. 13. Effect of the in vitro treatment with FGFR-selective inhibitors in lines with high expression of FGFR1 and/or FGFR4 and differential levels of N-cadherin. A) Effect of the treatment with FGFR inhibitors (BGJ398 and AZD4547) on the growth of adenocarcinoma and epidermoid carcinoma cell lines with endogenous expression of FGFR1 (H460), FGFR1 and FGFR4 (A549), FGFR1 and N-cadherin (H226) and FGFR1, FGFR4 and N-cadherin (H520). (B) Effect of the treatment with FGFR inhibitors (BGJ398 and AZD4547) on the growth of adenocarcinoma cell lines with exogenous expression of FGFR1 or FGFR4 (upper line), or exogenous expression of N-cadherin and FGFR1 or FGFR4 (lower line).

FIG. 13A shows the result of the cell proliferation (relative growth with regard to time) of the cell lines, untreated or treated with BGJ398 0.5 µM, BGJ398 1 µM, AZD4547 0.5 µM or AZD4547 1 µM. It may be observed that both inhibitors reduce the growth solely in the lines with high expression of N-cadherin, but do not exert a significant effect on those lines with low or no expression of N-cadherin at the concentrations tested. These results support the predictive role of N-cadherin with regard to FGFR-inhibiting therapies.

Figure 13B:
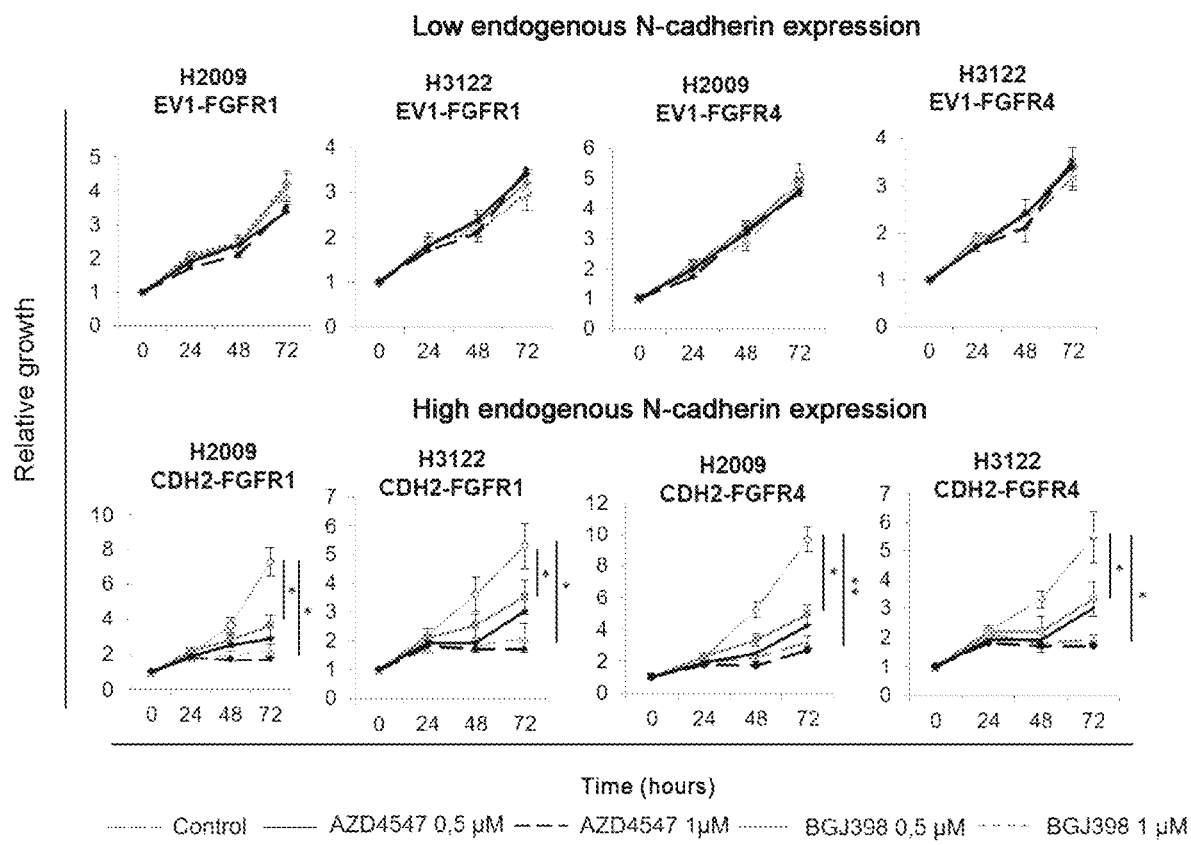

FIG. 13B shows the effect of two selective FGFR inhibitors on the proliferation of cell lines with exogenous expression of FGFR1 or FGFR4 in combination, or not, with exogenous expression of N-cadherin (CDH2). It may be observed that the inhibitors have no effect on the growth of the cell lines with no expression of exogenous N-cadherin, but do so when this is expressed (lower row).

b) N-Cadherin as a Predictive Factor in in-Vivo Anti-FGFR Therapy

To verify whether this predictive role has relevance in vivo, the efficacy of the inhibitor which displayed the greatest efficacy in the in vitro experiments (AZD4547) was tested in different patient-derived tumours xenografted in immunocompromised mice (Patient-derived xenografts (PDXs), see materials and methods).

Figure 14A:
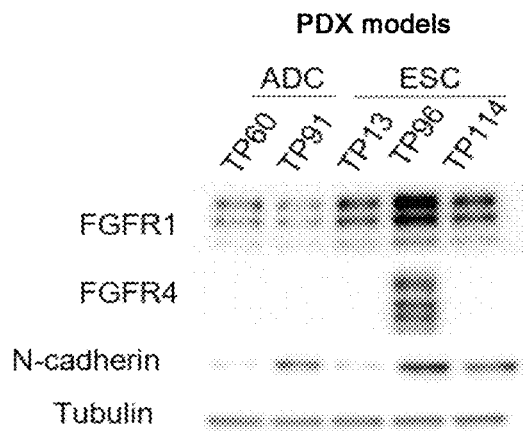
FIG. 14. Effect of in vivo treatment with an FGFR-selective inhibitor in lung PDXs with high FGFR1 and FGFR4 expression. (A) Western blot of FGFR1, FGFR4 and N-cadherin expression in the PDXs under study. (B) Effect of treatment with AZD4547 in patient-derived tumour models (PDXs) with low N-cadherin expression. (C) Effect of treatment with AZD4547 in patient-derived tumour models (PDXs) with high N-cadherin expression. (D) Graph showing the variation in volume of the tumours with regard to the commencement of the treatment, expressed in percentages. Determination by western blot of the effect of the treatment in FGFR-related signalling pathways. The p-values were obtained by means of Student's T-test with a confidence interval of 95%, and are represented by asterisks (*, $p<0.05$; , $p<0.01$; *, $p<0.001$). ADC=adenocarcinoma, SCC=epidermoid carcinoma.

Two adenocarcinoma models with similar expression of FGFR1 were selected, one with high expression of N-cadherin (TP91) and the other with low expression of this protein (TP60). Two epidermoid carcinoma models with comparable expression of FGFR1 were also selected, these having high and low expression of N-cadherin (TP114 and TP13, respectively). Likewise, an epidermoid carcinoma model with high expression of FGFR1, FGFR4 and N-cadherin (TP96) was also selected (FIG. 14A).

Figure 14B:
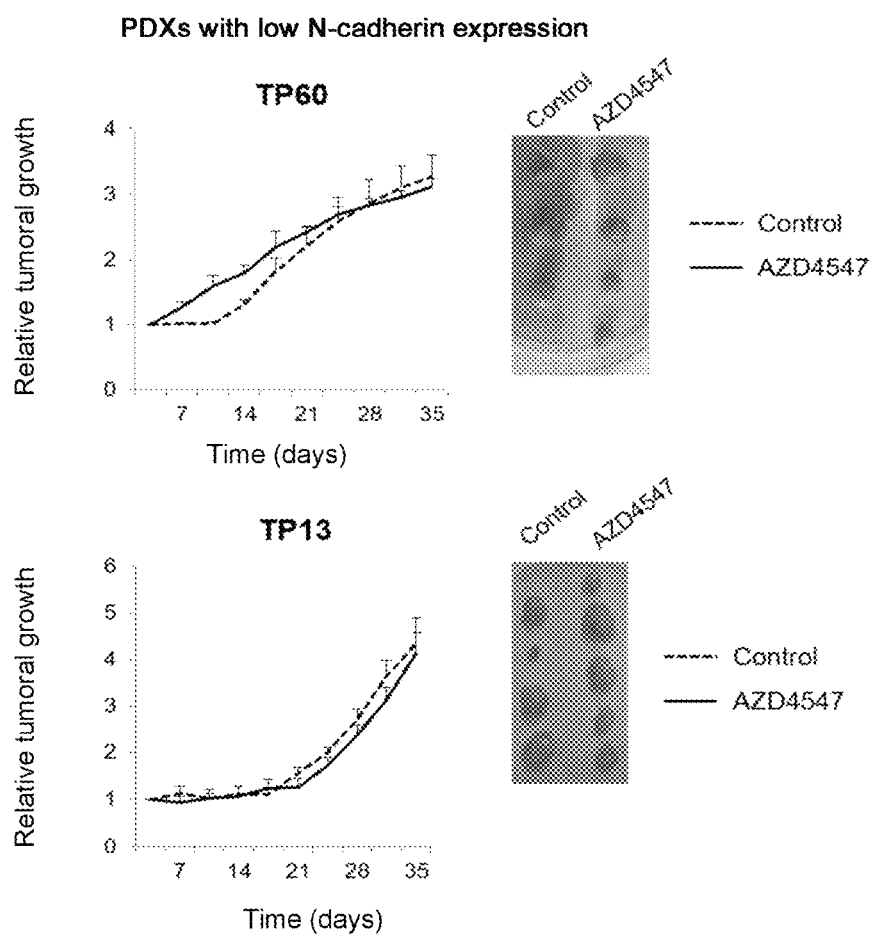
Figure 14C:
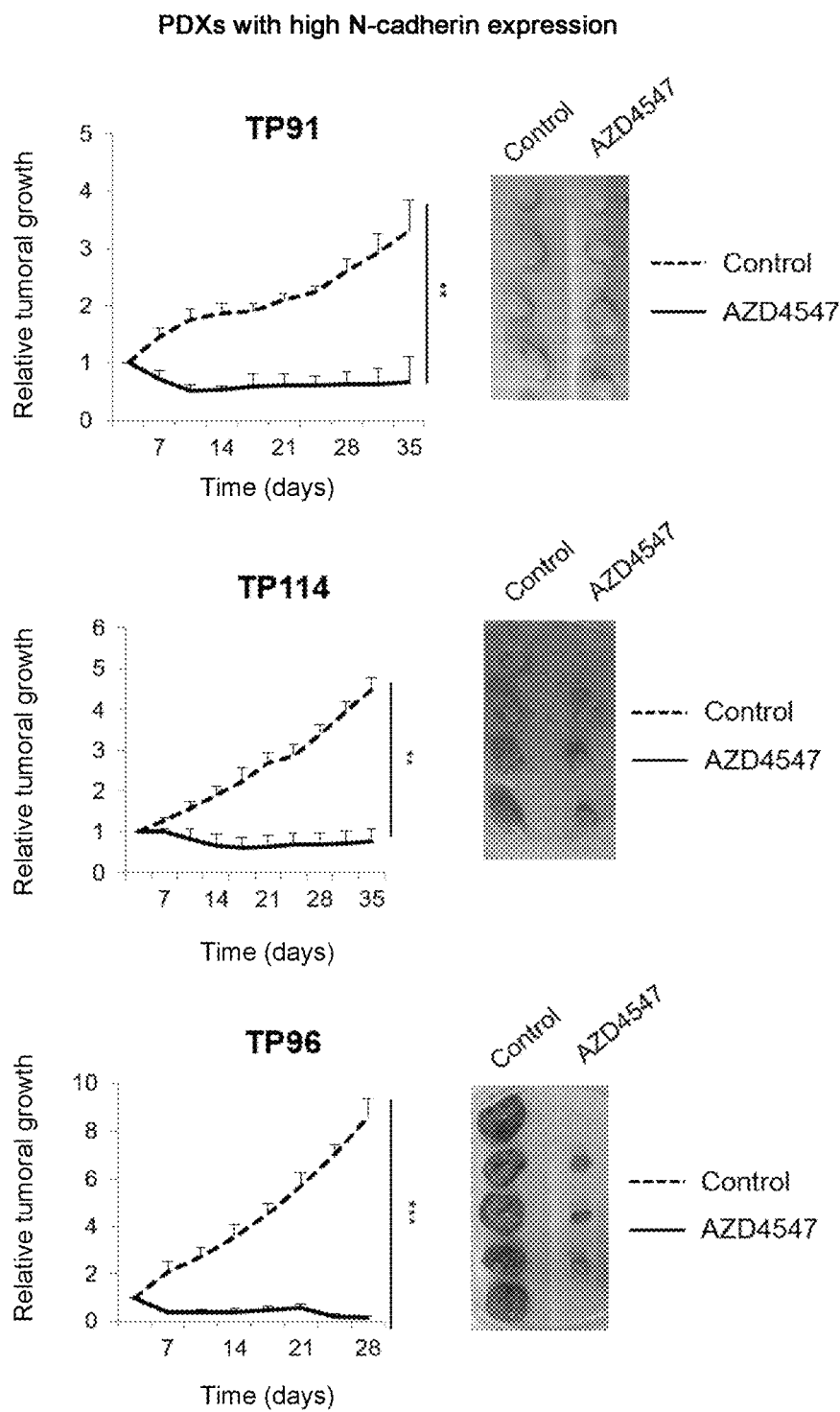

FIG. 14B shows how the treatment with AZD4547 had no effect on the tumour growth of the models with low N-cadherin expression (TP60 and TP13), regardless of their histology. However, in the tumour models with high expression of N-cadherin (TP91, TP114 and TP96, FIG. 14C) the treatment with this selective FGFR inhibitor caused a considerable reduction in growth, with an average reduction in volume of 14.4%, 25.5% and 1.4% with regard to the control condition, respectively.

Figure 14D:
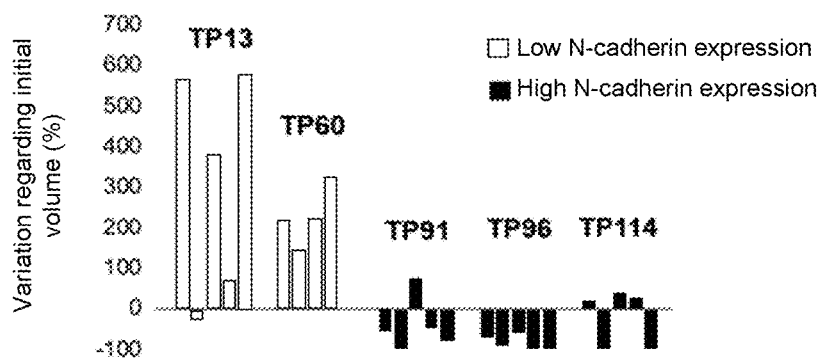

It may be highlighted that treatment with AZD4547 caused a complete tumour regression in ⅕, ⅖ and ⅖ of the tumours treated, respectively in each model. Furthermore, in the TP96 model, partial response to the treatment was achieved, this being defined as an average reduction in tumour volume of 50% or greater with regard to the volume at the commencement of the treatment (FIG. 14D)

Figure 14E:
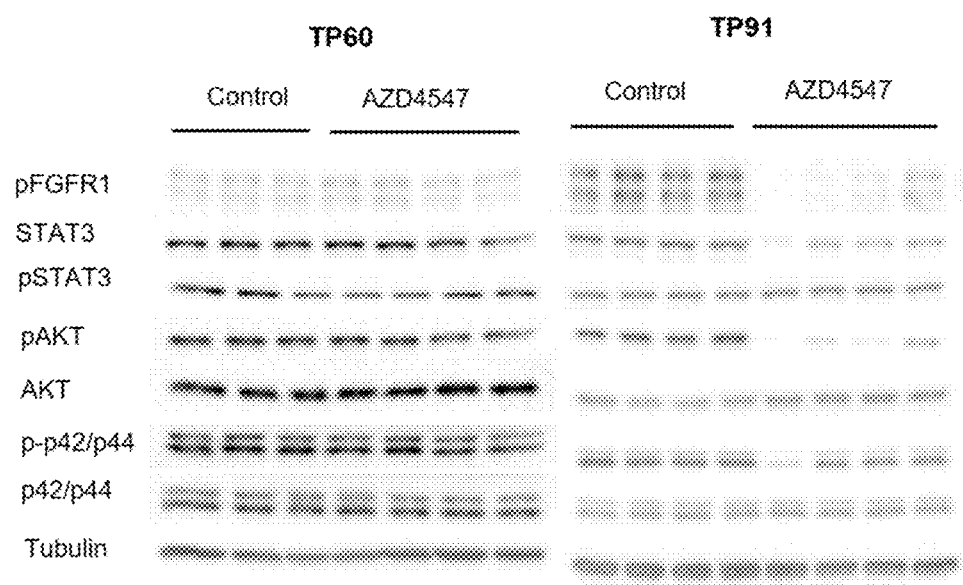

On analysing the effect of the inhibitor on the FGFR-related signalling pathways in two of the models treated (TP60 and TP91), we observed that the treatment does not alter the activation of the pathways studied in the model with low N-cadherin expression (TP60), while in the model with high expression of N-cadherin, TP91, AZD4547 caused a reduction in the levels of pSTAT3, pAKT and a modest reduction in p-p42/p44 activation (FIG. 14E). All these results support the predictive role of N-cadherin in FGFR-directed therapy, regardless of the histology.

These results reveal that the expression of these biomarker genes (N-cadherin in combination with FGFR1 and/or FGFR4) in a lung cancer sample from a patient is indicative of the efficacy of an anti-FGFR drug. By means of a simple analysis of the expression of the biomarkers N-cadherin and FGFR1 and/or FGFR4 it is possible to determine whether an anti-FGFR drug will be effective in the treatment of a subject. The results reveal that the efficacy of the treatment depends on the expression of N-cadherin in combination with the expression of FGFR1 and/or FGFR4. Analysis of the expression of N-cadherin to predict the response to a treatment with FGFR inhibitors has not been disclosed in the state of the art; it would therefore not be obvious to a person skilled in the art to determine the expression of these specific biomarkers in order to establish whether a subject will be resistant or sensitive to treatment with FGFR-inhibiting drugs.

All the data presented herein support the highly predictive role of the biomarker N-cadherin in anti-FGFR therapy for the treatment of tumours with high expression of FGFR1 and/or FGFR4.

BIBLIOGRAPHY

Altschul S F et al. Basic local alignment search tool. *J Mol Biol* (1990); 215(3): 403-10.

Blanco R et al. A gene-alteration profile of human lung cancer cell lines. *Human mutation* (2009); 30:1199-206.

Dutt A et al. Inhibitor-sensitive FGFR1 amplification in human non-small cell lung cancer. *PLoS one* 2011, 6(6): e20351.

Gheldof A and Berx G. Cadherins and epithelial-to-mesenchymal transition. *Prog Mol Biol Transl Sci* (2013); 116:317-36.

Helfrich B A et al. Antitumor activity of the epidermal growth factor receptor (EGFR) tyrosine kinase inhibitor gefitinib (ZD1839, Iressa) in non-small cell lung cancer cell lines correlates with gene copy number and EGFR mutations but not EGFR protein levels. *Clinical cancer research: an official journal of the American Association for Cancer Research* 2006; 12:7117-25.

Huang H P et al. The prognostic significance of fibroblast growth factor receptor 4 in non-small-cell lung cancer. OncoTargets and therapy (2015); 8:1157-64.

Jiang T et al. FGFR1 amplification in lung squamous cell carcinoma: a systematic review with meta-analysis. *Lung Cancer* 2015: 87(1):1-7.

Lim S H et al. Efficacy and safety of dovitinib in pre-treated patients with advanced squamous non-small cell lung cancer with FGFR1 amplification: A single-arm, phase 2 study. Cancer (2016); 122(19): 3024-31.

Nguyen T and Mège R M. N-cadherin and Fibroblast Growth Factor Receptors crosstalk in the control of developmental and cancer cell migrations. *Eur J Cell Biol* (2016); 95(11):415-26.

Qian X et al. N-cadherin/FGFR promotes metastasis through epithelial-to-mesenchymal transition and stem/progenitor cell-like properties. *Oncogene* (2014); 33(26):3411-21.

Quintanal-Villalonga A et al. Tyrosine Kinase Receptor Landscape in Lung Cancer: Therapeutical Implications. *Disease markers* 2016 1-14.

Hänze J et al. Epithelial mesenchymal transition status is associated with anti-cancer responses toward receptor tyrosine-kinase inhibition by dovitinib in human bladder cancer cells. *BMC Cancer* (2013); 11(13):589.

Wesche et al. Fibroblast growth factors and their receptors in cancer. *Biochem J* (2011); 437:199-213.

The invention claimed is:

1. A method of treatment of a subject suffering lung cancer, wherein the subject is a human being, comprising:
   (a) predicting the response of the subject to a treatment with at least one FGFR inhibitor, comprising:
      (a.1) detecting in a biological sample obtained from the subject the level of expression of the biomarker N-cadherin in combination with the level of expression of at least one of the biomarkers FGFR1 and/or FGFR4, wherein the biological sample is a biopsy of primary or metastatic tumor tissue of the subject,
      (a.2) comparing the levels of expression of the biomarkers determined in (a.1) with reference samples, wherein a high level of expression of the biomarker N-cadherin and also a high level of expression of at least one of the biomarkers FGFR1 and/or FGFR4, relative to their respective reference samples, indicates that the subject will respond to the treatment, and
   (b) administering to the subject identified in (a.2) as a subject with a high level of expression of the biomarker N-cadherin and also a high level of expression of at least one of the biomarkers FGFR1 and/or FGFR4, relative to their respective reference samples, a therapeutically effective amount of at least one FGFR inhibitor to treat lung cancer in the subject.

2. The method according to claim 1, wherein the determination of the level of expression of the biomarkers is performed by measuring the amount of N-cadherin protein and the amount of FGFR1 and/or FGFR4 protein in the sample, or by measuring the amount of mRNA of the N-cadherin gene and the amount of mRNA of the FGFR1 and/or FGFR4 genes in the sample.

3. The method according to claim 1, wherein the lung cancer is non-small cell lung cancer (NSCLC).

4. The method according to claim 3, wherein the non-small cell lung cancer is adenocarcinoma or epidermoid cell carcinoma.

5. The method according to claim 1, wherein the detection of the amount of the biomarkers is performed by means of at least one of the methods selected from the group consisting of HPLC (high performance liquid chromatography), LC/MS (liquid chromatography coupled to mass spectrometry), ELISA, DAS ELISA, protein immunoprecipitation, immunoelectrophoresis, Western Blot, protein immunostaining, Northern Blot, reverse transcription PCR (RT-PCR), quantitative PCR (q-PCR), RIA (radioimmunoassay), in situ hybridisation, nuclease protection assay, massive sequencing, immunocytochemical or immunohistochemical techniques, genomic DNA microarrays, protein microarrays, messenger RNA microarrays, cDNA microarrays, peptide microarrays, tissue microarrays, cell or transfection microarrays, antibody microarrays, lysate or serum microarrays, reverse phase protein microarrays, peptide microarrays, and genotyping microarrays.

6. The method according to claim 1, wherein high levels of expression of the biomarkers detected correspond to a level at least two times higher than the level of expression of the same biomarker in the reference sample.

7. The method according to claim 1, wherein the at least one FGFR inhibitor is selected from the group consisting of BGJ398, AZD4547, Debio-1347, Dovitinib, BLU9931, FIIN-2, JNJ-42756493, LY2874455, Ponatinib, BIBF1120, PD173074, PD166866, BLU554, S49076, NSC12, PHA-739358, TSU-68, BMS-540215, TKI-258, MK-2461, BMS-582664, AG 1296, SSR128129E, LY2874455 and SU5402.

* * * * *

SEQUENCE LISTING

<160> NUMBER OF SEQ ID NOS: 6

<210> SEQ ID NO 1
<211> LENGTH: 3873
<212> TYPE: DNA
<213> ORGANISM: Homo sapiens

<400> SEQUENCE: 1

| | | | | | |
|---|---|---|---|---|---|
| ctgctgccgc | tgctggcggc | cctgcttcag | gcgtctgtag | aggcttctgg | tgaaatcgca | 60 |
| ttatgcaaga | ctggatttcc | tgaagatgtt | tacagtgcag | tcttatcgaa | ggatgtgcat | 120 |
| gaaggacagc | ctcttctcaa | tgtgaagttt | agcaactgca | atggaaaaag | aaaagtacaa | 180 |
| tatgagagca | gtgagcctgc | agattttaag | gtggatgaag | atggcatggt | gtatgccgtg | 240 |
| agaagctttc | cactctcttc | tgagcatgcc | aagttcctga | tatatgccca | agacaaagag | 300 |
| acccaggaaa | agtggcaagt | ggcagtaaaa | ttgagcctga | agccaacctt | aactgaggag | 360 |
| tcagtgaagg | agtcagcaga | agttgaagaa | atagtgttcc | caagacaatt | cagtaagcac | 420 |
| agtggccacc | tacaaaggca | gaagagagac | tgggtcatcc | ctccaatcaa | cttgccagaa | 480 |
| aactccaggg | gaccttttcc | tcaagagctt | gtcaggatca | ggtctgatag | agataaaaac | 540 |
| ctttcactgc | ggtacagtgt | aactgggcca | ggagctgacc | agcctccaac | tggtatcttc | 600 |
| attatcaacc | ccatctcggg | tcagctgtcg | gtgacaaagc | ccctggatcg | cgagcagata | 660 |
| gcccggtttc | atttgagggc | acatgcagta | gatattaatg | gaaatcaagt | ggagaacccc | 720 |
| attgacattg | tcatcaatgt | tattgacatg | aatgacaaca | gacctgagtt | cttacaccag | 780 |
| gtttggaatg | gacagttcc | tgagggatca | agcctggaa | catatgtgat | gaccgtaaca | 840 |
| gcaattgatg | ctgacgatcc | caatgccctc | aatgggatgt | tgaggtacag | aatcgtgtct | 900 |
| caggctccaa | gcacccttc | acccaacatg | tttacaatca | acaatgagac | tggtgacatc | 960 |
| atcacagtgg | cagctggact | tgatcgagaa | aaagtgcaac | agtatacgtt | aataattcaa | 1020 |
| gctacagaca | tggaaggcaa | tcccacatat | ggcctttcaa | acacagccac | ggccgtcatc | 1080 |
| acagtgacag | atgtcaatga | caatcctcca | gagtttactg | ccatgacgtt | ttatggtgaa | 1140 |
| gttcctgaga | cagggtaga | catcatagta | gctaatctaa | ctgtgaccga | taaggatcaa | 1200 |
| ccccatacac | cagcctggaa | cgcagtgtac | agaatcagtg | gcggagatcc | tactggacgg | 1260 |
| ttcgccatcc | agaccgaccc | aaacagcaac | gacgggttag | tcaccgtggt | caaaccaatc | 1320 |
| gactttgaaa | caaataggat | gtttgtcctt | actgttgctg | cagaaaatca | agtgccatta | 1380 |
| gccaagggaa | ttcagcaccc | gcctcagtca | actgcaaccg | tgtctgttac | agttattgac | 1440 |
| gtaaatgaaa | acccttattt | tgcccccaat | cctaagatca | ttcgccaaga | agaagggctt | 1500 |
| catgccggta | ccatgttgac | aacattcact | gctcaggacc | cagatcgata | tatgcagcaa | 1560 |
| aatattagat | acactaaatt | atctgatcct | gccaattggc | taaaaataga | tcctgtgaat | 1620 |
| ggacaaataa | ctacaattgc | tgttttggac | cgagaatcac | caaatgtgaa | aaacaatata | 1680 |
| tataatgcta | ctttccttgc | ttctgacaat | ggaattcctc | ctatgagtgg | aacaggaacg | 1740 |
| ctgcagatct | atttacttga | tattaatgac | aatgcccctc | aagtgttacc | tcaagaggca | 1800 |
| gagacttgcg | aaactccaga | ccccaattca | attaatatta | cagcacttga | ttatgacatt | 1860 |
| gatccaaatg | ctgaccatt | tgcttttgat | cttcctttat | ctccagtgac | tattaagaga | 1920 |
| aattggacca | tcactcggct | taatggtgat | tttgctcagc | ttaatttaaa | gataaaattt | 1980 |
| cttgaagctg | gtatctatga | agttcccatc | ataatcacag | attcgggtaa | tcctcccaaa | 2040 |
| tcaaatattt | ccatcctgcg | cgtgaaggtt | tgccagtgtg | actccaacgg | ggactgcaca | 2100 |

```
gatgtggaca ggattgtggg tgcggggctt ggcaccggtg ccatcattgc catcctgctc     2160
tgcatcatca tcctgcttat ccttgtgctg atgtttgtgg tatggatgaa acgccgggat     2220
aaagaacgcc aggccaaaca acttttaatt gatccagaag atgatgtaag agataatatt     2280
ttaaaatatg atgaagaagg tggaggagaa gaagaccagg actatgactt gagccagctg     2340
cagcagcctg acactgtgga gcctgatgcc atcaagcctg tgggaatccg acgaatggat     2400
gaaagaccca tccacgccga gccccagtat ccggtccgat ctgcagcccc acaccctgga     2460
gacattgggg acttcattaa tgagggcctt aaagcggctg acaatgaccc cacagctcca     2520
ccatatgact ccctgttagt gtttgactat gaaggcagtg gctccactgc tgggtccttg     2580
agctccctta attcctcaag tagtggtggt gagcaggact atgattacct gaacgactgg     2640
gggccacggt tcaagaaact tgctgacatg tatggtggag gtgatgactg aacttcaggg     2700
tgaacttggt ttttggacaa gtacaaacaa tttcaactga tattcccaaa aagcattcag     2760
aagctaggct ttaactttgt agtctactag cacagtgctt gctggaggct ttggcatagg     2820
ctgcaaacca atttgggctc agagggaata tcagtgatcc atactgtttg gaaaaacact     2880
gagctcagtt acacttgaat tttacagtac agaagcactg gattttatg tgcctttttg      2940 tacctttttc agattggaat tagttttctg tttaaggctt taatggtact gatttctgaa     3000
acgataagta aaagacaaaa tattttgtgg tgggagcagt aagttaaacc atgatatgct     3060
tcaacacgct tttgttacat tgcatttgct tttattaaaa tacaaaatta aacaaacaaa     3120
aaaactcatg gagcgatttt attatcttgg gggatgagac catgagattg gaaaatgtac     3180
attacttcta gttttagact ttagtttgtt ttttttttt tcactaaaat cttaaaactt       3240
actcagctgg ttgcaaataa agggagtttt catatcacca atttgtagca aaattgaatt     3300
ttttcataaa ctagaatgtt agacacattt tggtcttaat ccatgtacac ttttttattt     3360
ctgtattttt ccacttcact gtaaaaatag tatgtgtaca taatgtttta ttggcatagt     3420
ctatggagaa gtgcagaaac ttcagaacat gtgtatgtat tatttggact atggattcag     3480
gttttttgca tgtttatatc tttcgttatg gataaagtat ttacaaaaca gtgacatttg     3540
attcaattgt tgagctgtag ttagaatact caattttttaa tttttttaat ttttttattt    3600
tttattttct ttttggtttg gggagggaga aaagttctta gcacaaatgt tttacataat     3660
ttgtaccaaa aaaaaaaaaa aaggaaagga agaaaggggg tggcctgaca ctggtggcac     3720
tactaagtgt gtgttttttt aaaaaaaaaa tggaaaaaaa aaagctttta aactggagag     3780
acttctgaca acagctttgc ctctgtattg tgtaccagaa tataaatgat acacctctga     3840
ccccagcgtt ctgaataaaa tgctaatttt gga                                   3873
```

<210> SEQ ID NO 2
<211> LENGTH: 2466
<212> TYPE: DNA
<213> ORGANISM: Homo sapiens

<400> SEQUENCE: 2

```
atgtggagct ggaagtgcct cctcttctgg gctgtgctgg tcacagccac actctgcacc       60
gctaggccgt ccccgacctt gcctgaacaa gcccagcccct ggggagcccc tgtggaagtg    120
gagtccttcc tggtccaccc cggtgacctg ctgcagcttc gctgtcggct gcgggacgat      180
gtgcagagca tcaactggct gcgggacggg gtgcagctgg cggaaagcaa ccgcacccgc     240
atcacagggg aggaggtgga ggtgcaggac tccgtgcccg cagactccgg cctctatgct     300
```

-continued

```
tgcgtaacca gcagcccctc gggcagtgac accacctact tctccgtcaa tgtttcagat    360
gctctcccct cctcggagga tgatgatgat gatgatgact cctcttcaga ggagaaagaa    420
acagataaca ccaaaccaaa ccgtatgccc gtagctccat attggacatc cccagaaaag    480
atggaaaaga aattgcatgc agtgccggct gccaagacag tgaagttcaa atgcccttcc    540
agtgggaccc caaaccccac actgcgctgg ttgaaaaatg gcaaagaatt caaacctgac    600
cacagaattg gaggctacaa ggtccgttat gccacctgga gcatcataat ggactctgtg    660
gtgccctctg acaagggcaa ctacacctgc attgtggaga atgagtacgg cagcatcaac    720
cacacatacc agctggatgt cgtggagcgg tcccctcacc ggcccatcct gcaagcaggg    780
ttgcccgcca acaaaacagt ggccctgggt agcaacgtgg agttcatgtg taaggtgtac    840
agtgacccgc agccgcacat ccagtggcta aagcacatcg aggtgaatgg gagcaagatt    900
ggcccagaca acctgcctta tgtccagatc ttgaagactg ctggagttaa taccaccgac    960
aaagagatgg aggtgcttca cttaagaaat gtctcctttg aggacgcagg ggagtatacg   1020
tgcttggcgg gtaactctat cggactctcc catcactctg catggttgac cgttctggaa   1080
gccctggaag agaggccggc agtgatgacc tcgcccctgt acctggagat catcatctat   1140
tgcacagggg ccttcctcat ctcctgcatg gtggggtcgg tcatcgtcta caagatgaag   1200
agtggtacca agaagagtga cttccacagc cagatggctg tgcacaagct ggccaagagc   1260
atccctctgc gcagacaggt aacagtgtct gctgactcca gtgcatccat gaactctggg   1320
gttcttctgg ttcggccatc acggctctcc tccagtggga ctcccatgct agcaggggtc   1380
tctgagtatg agcttcccga agaccctcgc tgggagctgc ctcgggacag actggtctta   1440
ggcaaacccc tgggagaggg ctgctttggg caggtggtgt ggcagaggc tatcgggctg   1500 gacaaggaca aacccaaccg tgtgaccaaa gtggctgtga agatgttgaa gtcggacgca   1560
acagagaaag acttgtcaga cctgatctca gaaatggaga tgatgaagat gatcgggaag   1620
cataagaata tcatcaacct gctgggggcc tgcacgcagg atggtccctt gtatgtcatc   1680
gtggagtatg cctccaaggg caacctgcgg gagtacctgc aggcccggag gcccccaggg   1740
ctggaatact gctacaaccc cagccacaac ccagaggagc agctctcctc caaggacctg   1800
gtgtcctgcg cctaccaggt ggcccgaggc atggagtatc tggcctccaa gaagtgcata   1860
caccgagacc tggcagccag gaatgtcctg gtgacagagg acaatgtgat gaagatagca   1920
gactttggcc tcgcacggga cattcaccac atcgactact ataaaaagac aaccaacggc   1980
cgactgcctg tgaagtggat ggcacccgag gcattatttg accggatcta cacccaccag   2040
agtgatgtgt ggtctttcgg ggtgctcctg tgggagatct tcactctggg cggctcccca   2100
taccccggtg tgcctgtgga ggaacttttc aagctgctga aggagggtca ccgcatggac   2160
aagcccagta actgcaccaa cgagctgtac atgatgatgc gggactgctg gcatgcagtg   2220
ccctcacaga gacccacctt caagcagctg gtggaagacc tggaccgcat cgtggccttg   2280
acctccaacc aggagtacct ggacctgtcc atgcccctgg accagtactc ccccagctt   2340 cccgacaccc ggagctctac gtgctcctca ggggaggatt ccgtcttctc tcatgagccg   2400
ctgcccgagg agccctgcct gccccgacac ccagcccagc ttgccaatgg cggactcaaa   2460
cgccgc                                                             2466
```

<210> SEQ ID NO 3
<211> LENGTH: 2406
<212> TYPE: DNA
<213> ORGANISM: Homo sapiens

<400> SEQUENCE: 3

```
atgcggctgc tgctggccct gttggggtc  ctgctgagtg tgcctgggcc tccagtcttg    60
tccctggagg cctctgagga agtggagctt gagccctgcc tggctcccag cctggagcag   120
caagagcagg agctgacagt agcccttggg cagcctgtgc gtctgtgctg tgggcgggct   180
gagcgtggtg gccactggta caaggagggc agtcgcctgg cacctgctgg ccgtgtacgg   240
ggctggaggg gccgcctaga gattgccagc ttcctacctg aggatgctgg ccgctacctc   300
tgcctggcac gaggctccat gatcgtcctg cagaatctca ccttgattac aggtgactcc   360
ttgacctcca gcaacgatga tgaggacccc aagtcccata gggacccctc gaataggcac   420
agttacccc  agcaagcacc ctactggaca caccccagc  gcatggagaa gaaactgcat   480
gcagtacctg cggggaacac cgtcaagttc cgctgtccag ctgcaggcaa ccccacgccc   540
accatccgct ggcttaagga tggacaggcc tttcatgggg agaaccgcat tggaggcatt   600
cggctgcgcc atcagcactg gagtctcgtg atggagagcg tggtgccctc ggaccgcggc   660
acatacacct gcctggtaga gaacgctgtg ggcagcatcc gctataacta cctgctagat   720
gtgctggagc ggtccccgca ccggcccatc ctgcaggccg ggctcccggc caacaccaca   780
gccgtggtgg gcagcgacgt ggagctgctg tgcaaggtgt acagcgatgc ccagccccac   840
atccagtggc tgaagcacat cgtcatcaac ggcagcagct tcggagccga cggtttcccc   900
tatgtgcaag tcctaaagac tgcagacatc aatagctcag aggtggaggt cctgtacctg   960
cggaacgtgt cagccgagga cgcaggcgag tacacctgcc tcgcaggcaa ttccatcggc  1020
ctctcctacc agtctgcctg gctcacggtg ctgccagagg aggaccccac atggaccgca  1080
gcagcgcccg aggccaggta tacgacatc  atcctgtacg cgtcgggctc cctggccttg  1140
gctgtgctcc tgctgctggc cgggctgtat cgagggcagg cgctccacgg ccggcaccc   1200
cgcccgcccg ccactgtgca gaagctctcc cgcttccctc tggcccgaca gttctccctg  1260
gagtcaggct cttccggcaa gtcaagctca tccctggtac gaggcgtgcg tctctcctcc  1320
agcggccccg ccttgctcgc cggcctcgtg agtctagatc tacctctcga cccactatgg  1380
gagttccccc gggacaggct ggtgcttggg aagcccctag gcgagggctg ctttggccag  1440
gtagtacgtg cagaggcctt tggcatggac cctgcccggc ctgaccaagc cagcactgtg  1500
gccgtcaaga tgctcaaaga caacgcctct gacaaggacc tggccgacct ggtctcggag  1560
atggaggtga tgaagctgat cggccgacac aagaacatca tcaacctgct tggtgtctgc  1620
acccaggaag ggcccctgta cgtgatcgtg gagtgcgccg ccaagggaaa cctgcgggag  1680
ttcctgcggg cccggcgccc cccaggcccc gacctcagcc ccgacggtcc tcggagcagt  1740
gaggggccgc tctccttccc agtcctggtc tcctgcgcct accaggtggc ccgaggcatg  1800
cagtatctgg agtcccggaa gtgtatccac cgggacctgg ctgcccgcaa tgtgctggtg  1860
actgaggaca tgtgatgaa  gattgctgac tttgggctgg cccgcggcgt ccaccacatt  1920
gactactata agaaaaccag caacggccgc ctgcctgtga gtggatggc  gcccgaggcc  1980
ttgtttgacc gggtgtacac acaccagagt gacgtgtggt cttttgggat cctgctatgg  2040
gagatcttca ccctcggggg ctccccgtat cctggcatcc cggtggagga gctgttctcg  2100
ctgctgcggg agggacatcg gatggaccga ccccacact  gccccccaga gctgtacggg  2160
ctgatgcgtg agtgctggca cgcagcgccc tcccagagg  ctaccttcaa gcagctggtg  2220
gaggcgctgg acaaggtcct gctggccgtc tctgaggagt acctcgacct ccgcctgacc  2280
```

```
ttcggaccct attcccccte tggtggggac gccagcagca cctgctcctc cagcgattct   2340
gtcttcagcc acgaccccct gccattggga tccagctcct tccccttcgg gtctggggtg   2400
cagaca                                                               2406
```

<210> SEQ ID NO 4
<211> LENGTH: 906
<212> TYPE: PRT
<213> ORGANISM: Homo sapiens

<400> SEQUENCE: 4

```
Met Cys Arg Ile Ala Gly Ala Leu Arg Thr Leu Leu Pro Leu Leu Ala
1               5                   10                  15

Ala Leu Leu Gln Ala Ser Val Glu Ala Ser Gly Glu Ile Ala Leu Cys
            20                  25                  30

Lys Thr Gly Phe Pro Glu Asp Val Tyr Ser Ala Val Leu Ser Lys Asp
        35                  40                  45

Val His Glu Gly Gln Pro Leu Leu Asn Val Lys Phe Ser Asn Cys Asn
    50                  55                  60

Gly Lys Arg Lys Val Gln Tyr Glu Ser Ser Glu Pro Ala Asp Phe Lys
65                  70                  75                  80

Val Asp Glu Asp Gly Met Val Tyr Ala Val Arg Ser Phe Pro Leu Ser
                85                  90                  95

Ser Glu His Ala Lys Phe Leu Ile Tyr Ala Gln Asp Lys Glu Thr Gln
            100                 105                 110

Glu Lys Trp Gln Val Ala Val Lys Leu Ser Leu Lys Pro Thr Leu Thr
        115                 120                 125

Glu Glu Ser Val Lys Glu Ser Ala Glu Val Glu Glu Ile Val Phe Pro
    130                 135                 140

Arg Gln Phe Ser Lys His Ser Gly His Leu Gln Arg Gln Lys Arg Asp
145                 150                 155                 160

Trp Val Ile Pro Pro Ile Asn Leu Pro Glu Asn Ser Arg Gly Pro Phe
                165                 170                 175

Pro Gln Glu Leu Val Arg Ile Arg Ser Asp Arg Asp Lys Asn Leu Ser
            180                 185                 190

Leu Arg Tyr Ser Val Thr Gly Pro Gly Ala Asp Gln Pro Pro Thr Gly
        195                 200                 205

Ile Phe Ile Ile Asn Pro Ile Ser Gly Gln Leu Ser Val Thr Lys Pro
    210                 215                 220

Leu Asp Arg Glu Gln Ile Ala Arg Phe His Leu Arg Ala His Ala Val
225                 230                 235                 240

Asp Ile Asn Gly Asn Gln Val Glu Asn Pro Ile Asp Ile Val Ile Asn
                245                 250                 255

Val Ile Asp Met Asn Asp Asn Arg Pro Glu Phe Leu His Gln Val Trp
            260                 265                 270

Asn Gly Thr Val Pro Glu Gly Ser Lys Pro Gly Thr Tyr Val Met Thr
        275                 280                 285

Val Thr Ala Ile Asp Ala Asp Asp Pro Asn Ala Leu Asn Gly Met Leu
    290                 295                 300

Arg Tyr Arg Ile Val Ser Gln Ala Pro Ser Thr Pro Ser Pro Asn Met
305                 310                 315                 320

Phe Thr Ile Asn Asn Glu Thr Gly Asp Ile Ile Thr Val Ala Ala Gly
                325                 330                 335

Leu Asp Arg Glu Lys Val Gln Gln Tyr Thr Leu Ile Ile Gln Ala Thr
            340                 345                 350
```

```
Asp Met Glu Gly Asn Pro Thr Tyr Gly Leu Ser Asn Thr Ala Thr Ala
        355                 360                 365

Val Ile Thr Val Thr Asp Val Asn Asp Asn Pro Pro Glu Phe Thr Ala
370             370                 375                 380

Met Thr Phe Tyr Gly Glu Val Pro Glu Asn Arg Val Asp Ile Ile Val
385                 390                 395                 400

Ala Asn Leu Thr Val Thr Asp Lys Asp Gln Pro His Thr Pro Ala Trp
                405                 410                 415

Asn Ala Val Tyr Arg Ile Ser Gly Gly Asp Pro Thr Gly Arg Phe Ala
                420                 425                 430

Ile Gln Thr Asp Pro Asn Ser Asn Asp Gly Leu Val Thr Val Val Lys
            435                 440                 445

Pro Ile Asp Phe Glu Thr Asn Arg Met Phe Val Leu Thr Val Ala Ala
        450                 455                 460

Glu Asn Gln Val Pro Leu Ala Lys Gly Ile Gln His Pro Pro Gln Ser
465                 470                 475                 480

Thr Ala Thr Val Ser Val Thr Val Ile Asp Val Asn Glu Asn Pro Tyr
                485                 490                 495

Phe Ala Pro Asn Pro Lys Ile Ile Arg Gln Glu Glu Gly Leu His Ala
            500                 505                 510

Gly Thr Met Leu Thr Thr Phe Thr Ala Gln Asp Pro Asp Arg Tyr Met
        515                 520                 525

Gln Gln Asn Ile Arg Tyr Thr Lys Leu Ser Asp Pro Ala Asn Trp Leu
        530                 535                 540

Lys Ile Asp Pro Val Asn Gly Gln Ile Thr Thr Ile Ala Val Leu Asp
545                 550                 555                 560

Arg Glu Ser Pro Asn Val Lys Asn Asn Ile Tyr Asn Ala Thr Phe Leu
                565                 570                 575

Ala Ser Asp Asn Gly Ile Pro Pro Met Ser Gly Thr Gly Thr Leu Gln
            580                 585                 590

Ile Tyr Leu Leu Asp Ile Asn Asp Asn Ala Pro Gln Val Leu Pro Gln
        595                 600                 605

Glu Ala Glu Thr Cys Glu Thr Pro Asp Pro Asn Ser Ile Asn Ile Thr
610                 615                 620

Ala Leu Asp Tyr Asp Ile Asp Pro Asn Ala Gly Pro Phe Ala Phe Asp
625                 630                 635                 640

Leu Pro Leu Ser Pro Val Thr Ile Lys Arg Asn Trp Thr Ile Thr Arg
                645                 650                 655

Leu Asn Gly Asp Phe Ala Gln Leu Asn Leu Lys Ile Lys Phe Leu Glu
            660                 665                 670

Ala Gly Ile Tyr Glu Val Pro Ile Ile Ile Thr Asp Ser Gly Asn Pro
        675                 680                 685

Pro Lys Ser Asn Ile Ser Ile Leu Arg Val Lys Val Cys Gln Cys Asp
        690                 695                 700

Ser Asn Gly Asp Cys Thr Asp Val Asp Arg Ile Val Gly Ala Gly Leu
705                 710                 715                 720

Gly Thr Gly Ala Ile Ile Ala Ile Leu Leu Cys Ile Ile Ile Leu Leu
                725                 730                 735

Ile Leu Val Leu Met Phe Val Val Trp Met Lys Arg Arg Asp Lys Glu
            740                 745                 750

Arg Gln Ala Lys Gln Leu Leu Ile Asp Pro Glu Asp Asp Val Arg Asp
        755                 760                 765
```

-continued

```
Asn Ile Leu Lys Tyr Asp Glu Glu Gly Gly Glu Asp Gln Asp
    770                 775                 780

Tyr Asp Leu Ser Gln Leu Gln Gln Pro Asp Thr Val Glu Pro Asp Ala
785                 790                 795                 800

Ile Lys Pro Val Gly Ile Arg Arg Met Asp Glu Arg Pro Ile His Ala
                805                 810                 815

Glu Pro Gln Tyr Pro Val Arg Ser Ala Ala Pro His Pro Gly Asp Ile
                820                 825                 830

Gly Asp Phe Ile Asn Glu Gly Leu Lys Ala Ala Asp Asn Asp Pro Thr
            835                 840                 845

Ala Pro Pro Tyr Asp Ser Leu Leu Val Phe Asp Tyr Glu Gly Ser Gly
850                 855                 860

Ser Thr Ala Gly Ser Leu Ser Ser Leu Asn Ser Ser Ser Ser Gly Gly
865                 870                 875                 880

Glu Gln Asp Tyr Asp Tyr Leu Asn Asp Trp Gly Pro Arg Phe Lys Lys
                885                 890                 895

Leu Ala Asp Met Tyr Gly Gly Gly Asp Asp
                900                 905

<210> SEQ ID NO 5
<211> LENGTH: 822
<212> TYPE: PRT
<213> ORGANISM: Homo sapiens

<400> SEQUENCE: 5

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
                20                  25                  30

Pro Trp Gly Ala Pro Val Glu Val Glu Ser Phe Leu Val His Pro Gly
            35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175

Lys Cys Pro Ser Ser Gly Thr Pro Asn Pro Thr Leu Arg Trp Leu Lys
            180                 185                 190

Asn Gly Lys Glu Phe Lys Pro Asp His Arg Ile Gly Gly Tyr Lys Val
        195                 200                 205

Arg Tyr Ala Thr Trp Ser Ile Ile Met Asp Ser Val Val Pro Ser Asp
    210                 215                 220

Lys Gly Asn Tyr Thr Cys Ile Val Glu Asn Glu Tyr Gly Ser Ile Asn
225                 230                 235                 240
```

-continued

His Thr Tyr Gln Leu Asp Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
    290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Glu Arg Pro Ala Val
        355                 360                 365

Met Thr Ser Pro Leu Tyr Leu Glu Ile Ile Ile Tyr Cys Thr Gly Ala
    370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
    450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
    530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590

Glu Gln Leu Ser Ser Lys Asp Leu Val Ser Cys Ala Tyr Gln Val Ala
        595                 600                 605

Arg Gly Met Glu Tyr Leu Ala Ser Lys Lys Cys Ile His Arg Asp Leu
    610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

```
Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
        675                 680                 685

Leu Leu Trp Glu Ile Phe Thr Leu Gly Gly Ser Pro Tyr Pro Gly Val
    690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
        755                 760                 765

Leu Ser Met Pro Leu Asp Gln Tyr Ser Pro Ser Phe Pro Asp Thr Arg
    770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
                805                 810                 815

Gly Gly Leu Lys Arg Arg
            820

<210> SEQ ID NO 6
<211> LENGTH: 802
<212> TYPE: PRT
<213> ORGANISM: Homo sapiens

<400> SEQUENCE: 6

Met Arg Leu Leu Leu Ala Leu Leu Gly Val Leu Leu Ser Val Pro Gly
1               5                   10                  15

Pro Pro Val Leu Ser Leu Glu Ala Ser Glu Glu Val Glu Leu Glu Pro
            20                  25                  30

Cys Leu Ala Pro Ser Leu Glu Gln Gln Glu Gln Glu Leu Thr Val Ala
        35                  40                  45

Leu Gly Gln Pro Val Arg Leu Cys Cys Gly Arg Ala Glu Arg Gly Gly
    50                  55                  60

His Trp Tyr Lys Glu Gly Ser Arg Leu Ala Pro Ala Gly Arg Val Arg
65                  70                  75                  80

Gly Trp Arg Gly Arg Leu Glu Ile Ala Ser Phe Leu Pro Glu Asp Ala
                85                  90                  95

Gly Arg Tyr Leu Cys Leu Ala Arg Gly Ser Met Ile Val Leu Gln Asn
            100                 105                 110

Leu Thr Leu Ile Thr Gly Asp Ser Leu Thr Ser Ser Asn Asp Asp Glu
        115                 120                 125

Asp Pro Lys Ser His Arg Asp Pro Ser Asn Arg His Ser Tyr Pro Gln
    130                 135                 140

Gln Ala Pro Tyr Trp Thr His Pro Gln Arg Met Glu Lys Lys Leu His
145                 150                 155                 160

Ala Val Pro Ala Gly Asn Thr Val Lys Phe Arg Cys Pro Ala Ala Gly
                165                 170                 175

Asn Pro Thr Pro Thr Ile Arg Trp Leu Lys Asp Gly Gln Ala Phe His
            180                 185                 190

Gly Glu Asn Arg Ile Gly Gly Ile Arg Leu Arg His Gln His Trp Ser
        195                 200                 205
```

```
Leu Val Met Glu Ser Val Val Pro Ser Asp Arg Gly Thr Tyr Thr Cys
    210                 215                 220

Leu Val Glu Asn Ala Val Gly Ser Ile Arg Tyr Asn Tyr Leu Leu Asp
225                 230                 235                 240

Val Leu Glu Arg Ser Pro His Arg Pro Ile Leu Gln Ala Gly Leu Pro
                245                 250                 255

Ala Asn Thr Thr Ala Val Val Gly Ser Asp Val Glu Leu Leu Cys Lys
                260                 265                 270

Val Tyr Ser Asp Ala Gln Pro His Ile Gln Trp Leu Lys His Ile Val
        275                 280                 285

Ile Asn Gly Ser Ser Phe Gly Ala Asp Gly Phe Pro Tyr Val Gln Val
    290                 295                 300

Leu Lys Thr Ala Asp Ile Asn Ser Ser Glu Val Glu Val Leu Tyr Leu
305                 310                 315                 320

Arg Asn Val Ser Ala Glu Asp Ala Gly Glu Tyr Thr Cys Leu Ala Gly
                325                 330                 335

Asn Ser Ile Gly Leu Ser Tyr Gln Ser Ala Trp Leu Thr Val Leu Pro
                340                 345                 350

Glu Glu Asp Pro Thr Trp Thr Ala Ala Ala Pro Glu Ala Arg Tyr Thr
                355                 360                 365

Asp Ile Ile Leu Tyr Ala Ser Gly Ser Leu Ala Leu Ala Val Leu Leu
370                 375                 380

Leu Leu Ala Gly Leu Tyr Arg Gly Gln Ala Leu His Gly Arg His Pro
385                 390                 395                 400

Arg Pro Pro Ala Thr Val Gln Lys Leu Ser Arg Phe Pro Leu Ala Arg
                405                 410                 415

Gln Phe Ser Leu Glu Ser Gly Ser Ser Gly Lys Ser Ser Ser Ser Leu
                420                 425                 430

Val Arg Gly Val Arg Leu Ser Ser Ser Gly Pro Ala Leu Leu Ala Gly
            435                 440                 445

Leu Val Ser Leu Asp Leu Pro Leu Asp Pro Leu Trp Glu Phe Pro Arg
450                 455                 460

Asp Arg Leu Val Leu Gly Lys Pro Leu Gly Glu Gly Cys Phe Gly Gln
465                 470                 475                 480

Val Val Arg Ala Glu Ala Phe Gly Met Asp Pro Ala Arg Pro Asp Gln
                485                 490                 495

Ala Ser Thr Val Ala Val Lys Met Leu Lys Asp Asn Ala Ser Asp Lys
                500                 505                 510

Asp Leu Ala Asp Leu Val Ser Glu Met Glu Val Met Lys Leu Ile Gly
            515                 520                 525

Arg His Lys Asn Ile Ile Asn Leu Leu Gly Val Cys Thr Gln Glu Gly
        530                 535                 540

Pro Leu Tyr Val Ile Val Glu Cys Ala Ala Lys Gly Asn Leu Arg Glu
545                 550                 555                 560

Phe Leu Arg Ala Arg Arg Pro Pro Gly Pro Asp Leu Ser Pro Asp Gly
                565                 570                 575

Pro Arg Ser Ser Glu Gly Pro Leu Ser Phe Pro Val Leu Val Ser Cys
                580                 585                 590

Ala Tyr Gln Val Ala Arg Gly Met Gln Tyr Leu Glu Ser Arg Lys Cys
                595                 600                 605

Ile His Arg Asp Leu Ala Ala Arg Asn Val Leu Val Thr Glu Asp Asn
610                 615                 620
```

```
Val Met Lys Ile Ala Asp Phe Gly Leu Ala Arg Gly Val His His Ile
625                 630                 635                 640

Asp Tyr Tyr Lys Lys Thr Ser Asn Gly Arg Leu Pro Val Lys Trp Met
                645                 650                 655

Ala Pro Glu Ala Leu Phe Asp Arg Val Tyr Thr His Gln Ser Asp Val
            660                 665                 670

Trp Ser Phe Gly Ile Leu Leu Trp Glu Ile Phe Thr Leu Gly Gly Ser
        675                 680                 685

Pro Tyr Pro Gly Ile Pro Val Glu Glu Leu Phe Ser Leu Leu Arg Glu
    690                 695                 700

Gly His Arg Met Asp Arg Pro Pro His Cys Pro Pro Glu Leu Tyr Gly
705                 710                 715                 720

Leu Met Arg Glu Cys Trp His Ala Ala Pro Ser Gln Arg Pro Thr Phe
                725                 730                 735

Lys Gln Leu Val Glu Ala Leu Asp Lys Val Leu Leu Ala Val Ser Glu
            740                 745                 750

Glu Tyr Leu Asp Leu Arg Leu Thr Phe Gly Pro Tyr Ser Pro Ser Gly
        755                 760                 765

Gly Asp Ala Ser Ser Thr Cys Ser Ser Ser Asp Ser Val Phe Ser His
    770                 775                 780

Asp Pro Leu Pro Leu Gly Ser Ser Ser Phe Pro Phe Gly Ser Gly Val
785                 790                 795                 800

Gln Thr
```